US012065399B2

(12) United States Patent
Biemans et al.

(10) Patent No.: US 12,065,399 B2
(45) Date of Patent: Aug. 20, 2024

(54) ARYLSULFONAMIDE DERIVATIVES

(71) Applicant: Hoffmann-La Roche Inc., Little Falls, NJ (US)

(72) Inventors: Barbara Biemans, Riehen (CH); Luca Gobbi, Buus (CH); Georg Jaeschke, Basel (CH); Henner Knust, Rheinfelden (DE); Lothar Lindemann, Basel (CH); Fionn O'Hara, Basel (CH); Jean-Marc Plancher, Hagenthal-le-Bas (FR)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 17/672,297

(22) Filed: Feb. 15, 2022

(65) Prior Publication Data
US 2022/0169599 A1    Jun. 2, 2022

Related U.S. Application Data

(63) Continuation of application No. PCT/EP2020/072693, filed on Aug. 13, 2020.

(30) Foreign Application Priority Data
Aug. 15, 2019   (EP) .................... 19191927

(51) Int. Cl.
*C07C 311/21* (2006.01)
*C07D 213/59* (2006.01)
*C07D 231/12* (2006.01)
*C07D 231/24* (2006.01)

(52) U.S. Cl.
CPC .......... *C07C 311/21* (2013.01); *C07D 213/59* (2013.01); *C07D 231/12* (2013.01); *C07D 231/24* (2013.01)

(58) Field of Classification Search
CPC .. C07D 213/59; C07D 213/71; C07D 231/12; C07D 231/24; C07D 263/56; C07C 311/21; A61K 31/145
See application file for complete search history.

(56) References Cited

FOREIGN PATENT DOCUMENTS

| EP | 2 599 775 A1 | 6/2013 |
| JP | 2013-507350 A | 3/2013 |
| WO | 2011/042797 A1 | 4/2011 |
| WO | 2012/015024 A1 | 2/2012 |

OTHER PUBLICATIONS

Bell, CAPLUS Abstract 25:24441 (1931).*
Bell, CAPLUS Abstract 26:3778 (1932).*
Pearce et al., Failure modes in anticancer drug discovery and development, Cancer Drug Design and Discovery Edited by Stephen Neidle, Chapter 18, pp. 424-435 (2008).*
Gura, Systems for identifying new drugs are often faulty, Science, Nov. 7, 1997, 278(5340): 1041-2.*
Johnson et al., Relationships between drug activity in NCI preclinical in vitro and in vivo models and early clinical trials, Br J Cancer. May 18, 2001, 84(10): 1424-31.*
Simone, Introduction, Omenn, Cancer Prevention, Part XIV. Oncology, Cecil Textbook of Medicine, 20th Edition, vol. 1, pp. 1004-1010 (1996).*
Merck Manual Professional Online Edition, Acute Leukemia, 6 pages, 2013.*
Battaglia, G. et al., "Pharmacological Activation of mGlu4 Metabotropic Glutamate Receptors Reduces Nigrostriatal Degeneration in Mice Treated with 1-Methyl-4-Phenyl-1,2,3,6-Tetrahydropyridine" J Neurosci 26(27):7222-7229 (Jul. 5, 2006).
Bell, J. et al., "Investigations in the Diphenyl Series. Part X. The Bromination of 4-p-Toluenesulphonamidodiphenyl" J Chem Soc:2338-2343 (Jan. 1, 1931).
Célanire, S. et al., "Recent Advances in the Drug Discovery of Metabotropic Glutamate Receptor 4 (mGluR4) Activators for the Treatment of CNS and non-CNS Disorders" Expert Opin Drug Dis 7(3):261-280 (Feb. 14, 2012).
Chaki, S. et al., "Targeting of Metabotropic Glutamate Receptors for the Development of Novel Antidepressants" Chronic Stress 3:1-13 (Apr. 3, 2019).
Chang, H.J. et al., "Metabotropic Glutamate Receptor 4 Expression in Colorectal Carcinoma and Its Prognostic Significance" Clin Cancer Res 11(9):3288-3295 (May 1, 2005).
Harpsøe, K. et al., "Selective Negative Allosteric Modulation of Metabotropic Glutamate Receptors—A Structural Perspective of Ligands and Mutants" Sci Rep 5(1):13869 (Sep. 11, 2015).
International Preliminary Report on Patentability for PCT/EP2020/072693, issued Feb. 8, 2022, pp. 1-8.
International Search Report for PCT/EP/2020/072693, mailed Oct. 12, 2020, pp. 1-5.
Marino, M.J. et al., "Allosteric Modulation of Group III Metabotropic Glutamate Receptor 4: A Potential Approach to Parkinson's Disease Treatment" Proc Natl Acad Sci USA 100(23):13668-16673 (Nov. 11, 2003).
Niswender, C.M. et al., "Discovery, Characterization, and Antiparkinsonian Effect of Novel Positive Allosteric Modulators of Metabotropic Glutamate Receptor 4" Mol Pharmacol 74(5):1345-1358 (Nov. 1, 2008).

(Continued)

*Primary Examiner* — Deepak R Rao

(57) ABSTRACT

The present invention provides new arylsulfonamide compounds having the general formula (I)

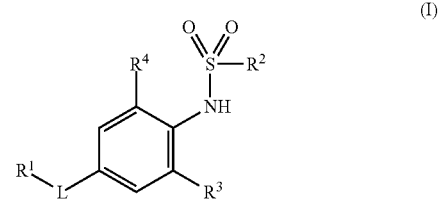

wherein L, $R^1$, $R^2$, $R^3$ and $R^4$ are as described herein, compositions including the compounds, processes of manufacturing the compounds and methods of using the compounds.

17 Claims, 1 Drawing Sheet

(56) References Cited

OTHER PUBLICATIONS

Pałucha, A. et al., "Group III mGlu Receptor Agonists Produce Anxiolytic- and Antidepressant-like Effects After Central Administration in Rats" Neuropharmacol 46(2):151-159 (Feb. 1, 2004).

Pissimissis, N. et al., "The Glutamatergic System Expression in Human PC-3 and LNCaP Prostate Cancer Cells" Anticancer Res 29(1):371-378 (Jan. 1, 2009).

Prediger, R.D.S. et al., "Anxiety in Parkinson's Disease: A Critical Review of Experimental and Clinical Studies" Neuropharmacol 62(1):115-124 (Jan. 1, 2012).

Rovira, X. et al., "OptoGluNAM4.1, a Photoswitchable Allosteric Antagonist for Real-Time Control of mGlu4 Receptor Activity" Cell Chem Biol 23(8):929-934 (Aug. 18, 2016).

Stachowicz, K. et al., "Anxiolytic-like Effect of Group III mGlu Receptor Antagonist is Serotonin-dependent" Neuropharmacol 52(2):306-312 (Oct. 3, 2006).

Stachowicz, K. et al., "Anxiolytic-like Effects of PHCCC, an Allosteric Modulator of mGlu4 Receptors, in Rats" Eur J Pharmacol 498(1-3):153-156 (Sep. 1, 2004).

Stansley, B.J. et al., "Neuropharmacological Insight from Allosteric Modulation of mGlu Receptors" TRRNDS Pharmacol Sci 40(4):240-251 (Feb. 26, 2019).

Utley, T. et al., "Synthesis and SAR of a Novel Metabotropic Glutamate Receptor 4 (mGlu4) Antagonist: Unexpected 'Molecular Switch' From a Closely Related mGlu4 Positive Allosteric Modulator" Bioorg Med Chem Lett 21(23):6955-6959 (Oct. 8, 2011).

Vernon, A.C. et al., "Additive Neuroprotection by Metabotropic Glutamate Receptor Subtype-selective Ligands in a Rat Parkinson's Model" Neuroreport 19(4):475-480 (Mar. 5, 2008).

Volpi, C. et al., "Allosteric Modulation of Metabotropic Glutamate Receptor 4 Activates IDO1-dependent, Immunoregulatory Signaling in Dendritic Cells" Neuropharmacol 102:59-71 (Oct. 30, 2015).

Yoo, B.C. et al., "Metabotropic Glutamate Receptor 4-Mediated 5-Fluorouracil Resistance in a Human Colon Cancer Cell Line" Clin Cancer Res 10(12 Pt 1):4176-4184 (Jun. 15, 2004).

* cited by examiner

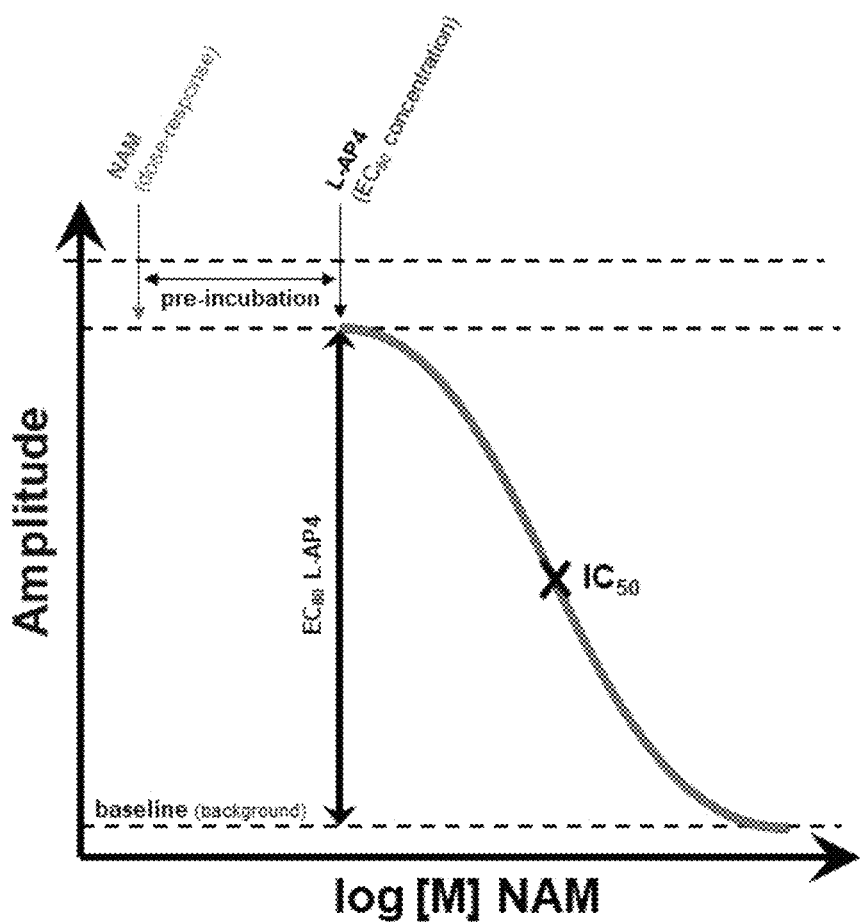

ARYLSULFONAMIDE DERIVATIVES

CROSS-REFERENCE TO RELATED APPLICATIONS

This application is a continuation of International Application PCT/EP2020/072693, filed on Aug. 13, 2020, which claims benefit of priority to European Application 19191927.3, filed on Aug. 15, 2019, each of which is incorporated herein by reference in its entirety.

BACKGROUND

The present invention relates to arylsulfonamide compounds useful as mGluR4 negative allosteric modulators, their manufacture, pharmaceutical compositions comprising said compounds and their use as medicaments for the therapeutic and/or prophylactic treatment of diseases associated with mGluR4, such as cancer, anxiety, emesis, obsessive compulsive disorder, autism, neuroprotection, Parkinson's Disease, depression and diabetes type 2.

Metabotropic glutamate receptor 4 (mGluR4) is a protein that in humans is encoded by the GRM4 gene. Together with GRM6, GRM7 and GRM8 it belongs to group III of the metabotropic glutamate receptor family, and is negatively coupled to adenylate cyclase via activation of the Gαi/o protein. It is expressed primarily on presynaptic terminals, functioning as an autoreceptor or heteroreceptor and its activation leads to decreases in transmitter release from presynaptic terminals. mGluR4 is currently receiving much attention based primarily upon its unique distribution and the recent evidence that activation and deactivation of this receptor plays key modulatory role in many CNS and non-CNS pathways (Celanire S, Campo B, Expert Opinion in Drug Discovery, 2012).

The similarity in the ligand binding domains of group III mGluRs creates a challenge for identifying selective orthosteric ligands of this receptor, although some progress has been made in this area. However, targeting allosteric modulators rather than orthosteric ligands provides a broader opportunity to identify molecules that are exclusively selective between mGluRs.

mGluR4 allosteric modulators are emerging as promising therapeutic agents for the treatment of motor (and non-motor) symptoms as well as a disease-modifying agent in Parkinson's disease through a non-dopaminergic approach.

Parkinson's disease (PD) is a progressive neurodegenerative disease that results in the loss of dopaminergic neurons in the substantia nigra (SN). One consequence of the depletion of dopamine in this disease is a series of movement disorders, including bradykinesia, akinesia, tremor, gait disorders and problems with balance. These motor disturbances form the hallmark of PD, although there are many other non-motor symptoms that are associated with the disease. Early in the course of the disease, PD symptoms are effectively treated by dopamine replacement or augmentation, with the use of dopamine D2 receptor agonists, levodopa or monoamine oxidase B inhibitors. However, as the disease progresses these agents become less effective in controlling motor symptoms. Additionally, their use is limited by the emergence of adverse effects including dopamine agonist-induced dyskinesias. Consequently, there remains a need for new approaches to the treatment of PD that improve the effectiveness of the control of motor symptoms.

The neuroprotective effects of selective mGluR4 modulators was also described in *Neuroreport*, 19(4), 475-8, 2008, *Proc. Natl. Acad. Sci, USA*, 100(23), 13668-73, 2003, *J. Neurosci.* 26(27), 7222-9, 2006, and *Mol. Pharmacol.* 74(5), 1345-58, 2008.

Moreover, mGluR4 was shown to be expressed in prostate cancer cell-line (*Anticancer Res.* 29(1), 371-7, 2009) or colorectal carcinoma (*Clin. Cancer Res.*, 11(9), 3288-95, 2005). mGluR4 modulators may therefore have also potential role for the treatment of cancers. In colorectal cancer, overexpression on mGluR4 is correlated with recurrence and poor disease-free survival (Chang et, al., *Clinic. Cancer Res.*, May 1, 2005 (11)(9), 3288-3295.) It was also shown that overexpression of mGluR4 mediates the 5-fluorouracil (5-FU) resistance phenotype, where development of 5-FU resistance has been a major obstacle in colorectal cancer chemotherapy. T (Yoo et al., *Clin. Cancer Res.* 2004, 10(12 Pt 1):4176-4184.) The mGluR4 antagonist MAP 4 acted synergically with 5-FU to enhance death in 5-FU resistant cells highly expressing mGluR4.

Anxiety disorders are among the most prevalent psychiatric disorders in the world, and are co-morbid with Parkinson's disease (Prediger R, et al. *Neuropharmacology* 2012, 62:115-24). Excessive glutamatergic neurotransmission is one important feature of anxiety pathophysiology. Based on presynaptic localization of mGluR4 in brain areas involved in anxiety and mood disorders, and dampening excessive brain excitability, the mGluR4 modulators may represent a new generation of anxiolytic therapeutics (*Eur. J. Pharmacol.*, 498(1-3), 153-6, 2004). The group III mGlu receptor antagonist (RS)-α-cyclopropyl-4-phosphonophenylglycine (CPPG) which acts on mGluR4, was shown to have an anxiolytic effect (Stachowicz et al., *Neuropharmacology* 52 (2007) 306-331).

mGluR4 modulators were also shown to exert anti-depressive actions (Palucha et al., *Neuropharmacology*, 46(2), 151-9, 2004).

Therefore, modulating the mGluR4 activity is a promising strategy for the treatment or prevention of diseases associated with mGluR4, such as cancer, anxiety, Parkinson's disease, emesis, obsessive compulsive disorder, anorexia, autism, neuroprotection, depression and type 2 diabetes. A number of recent publications have highlighted the need for selective mGlu4 negative allosteric modulators (NAMs) as pharmacological tools to help elucidate the biology and probe therapeutic implications of this receptor (Stansley et. al., *Trends in Pharmacological Sciences*, 2019, 40, 240-252; Harpsoe et. al., *Scientific Reports*, 2015, 5, 13869; Chaki et al., *Chronic Stress*, 2019, doi:10.1177/2470547019837712) The only two published mGlu4 NAMs—a small molecule (Utley et al., *Bioorganic & Medicinal Chemistry Letters*, 2011, 21, 6955-6959) and a photoswitchable tool compound (Rovira et al., *Cell Chemical Biology*, 2016, 23, 929-934) suffer from low potency (5-10 uM).

Due to the scarcity of mGluR4 NAMs, there is a need to provide such compounds, and it is an object of this disclosure to provide mGluR4 NAMs useful for the treatment or prevention or amelioration of mGluR4 mediated diseases and disorders, such as cancer, anxiety, emesis, obsessive compulsive disorder, anorexia, autism, neuroprotection, Parkinson's disease, depression and type 2 diabetes, with improved therapeutic properties, as well as formulations, treatments and therapies to treat such diseases and disorders.

SUMMARY OF THE DISCLOSURE

A first object of the present invention is a compound of formula (I)

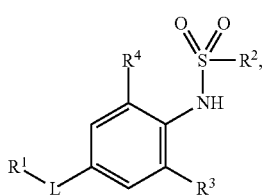

(I)

wherein
L is a bond or —C≡C—;
R¹ is phenyl optionally substituted with 1 or 2 substituents independently selected from halogen, hydroxy, lower alkyl, lower alkoxy or haloalkyl; or
pyridyl optionally substituted with halogen, lower alkyl, lower alkoxy or haloalkyl; or
pyrazolyl optionally substituted with halogen, hydroxy, lower alkyl, lower alkoxy or haloalkyl;
R² is phenyl optionally substituted with 1 to 3 substituents selected from halogen, hydroxy, lower alkyl, lower alkoxy, haloalkyl or alkoxyalkyl; or
a heteroaryl group optionally substituted with halogen, hydroxy, lower alkyl, lower alkoxy, haloalkyl or alkoxyalkyl, selected from

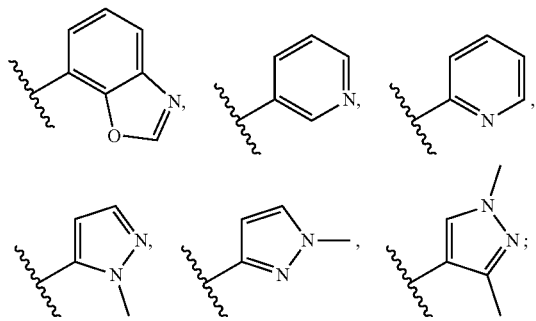

R³ and R⁴ are halogen, haloalkyl, lower alkyl or lower alkoxy;
or a pharmaceutically acceptable salt thereof.

A further object of the invention is a process for the preparation of a compound of formula (I) as described herein, or a pharmaceutically acceptable salt thereof, comprising reacting an amine 1

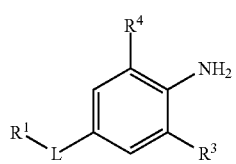

1 with a sulfonyl chloride 2

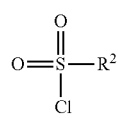

2 wherein R¹, R², R³ and R⁴ are as defined above, to form said compound of formula (I), and if desired, converting the compounds obtained into a pharmaceutically acceptable salt thereof.

A further object of the present invention is a compound as described herein, or a pharmaceutically acceptable salt thereof, when manufactured according to the process as described above.

A further object of the present invention is a compound of formula (I) as described herein, or a pharmaceutically acceptable salt thereof, for use as therapeutically active substance.

A further object of the present invention is a pharmaceutical composition comprising a compound of formula (I) as described herein, or a pharmaceutically acceptable salt thereof, and a pharmaceutically acceptable excipient.

A further object of the present invention is a compound of formula (I) as described herein, or a pharmaceutically acceptable salt thereof, for use in the therapeutic and/or prophylactic treatment of cancer, anxiety, emesis, obsessive compulsive disorder, autism, neuroprotection, Parkinson's disease, depression and diabetes type 2.

A further object of the present invention is the use of a compound of formula (I) as described herein, or a pharmaceutically acceptable salt thereof, for the therapeutic and/or prophylactic treatment of cancer, anxiety, emesis, obsessive compulsive disorder, autism, neuroprotection Parkinson's disease, depression and diabetes type 2.

A further object of the present invention is the use of a compound of formula (I) as described herein, or a pharmaceutically acceptable salt thereof, for the preparation of a medicament for the therapeutic and/or prophylactic treatment of cancer, anxiety, emesis, obsessive compulsive disorder, autism, neuroprotection, Parkinson's disease, depression and diabetes type 2.

A further object of the present invention is a method for the therapeutic and/or prophylactic treatment of cancer, anxiety, emesis, obsessive compulsive disorder, autism, neuroprotection, Parkinson's disease, depression and diabetes type 2, which method comprises administering an effective amount of a compound of formula (I) as described herein, or a pharmaceutically acceptable salt thereof.

It has been surprisingly found that compounds of the present invention are mGluR4 NAMs.

BRIEF DESCRIPTION OF THE FIGURES

FIG. 1 illustrates of the experimental outline for mGlu4 NAM $Ca^{2+}$ mobilization screening assay and the determination of $EC_{50}$ and % Emax values.

DETAILED DESCRIPTION OF THE DISCLOSURE

The following definitions of the general terms used in the present description apply irrespectively of whether the terms in question appear alone or in combination with other groups.

The term "lower alkyl", alone or in combination with other groups, refers to saturated straight- or branched-chain alkyl group, with single or multiple branching, wherein the alkyl group in general comprises 1 to 7 carbon atoms ("$C_{1-7}$-alkyl"), for example, methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl, 1,2-dimethyl-propyl and the like. Particular lower alkyl groups have 1 to 4 carbon atoms ("$C_{1-4}$-alkyl").

The term "alkoxy", alone or in combination, denotes a group of the formula alkyl-O— in which the term "alkyl" has the previously given significance, such as methoxy, ethoxy, n-propoxy, isopropoxy, n-butoxy, isobutoxy, sec-butoxy and tert-butoxy. Particular "alkoxy" are methoxy and tert-butyloxy.

The term "lower alkoxy" denotes an alkyl group as defined above, wherein the alkyl residue is attached via an oxygen atom.

The terms "halogen" or "halo", alone or in combination, denotes fluorine, chlorine, bromine or iodine and particularly fluorine, chlorine or bromine, more particularly fluorine and chlorine. The term "halo", in combination with another group, denotes the substitution of said group with at least one halogen, particularly substituted with one to five halogens, particularly one to four halogens, i.e. one, two, three or four halogens.

The term "haloalkyl" refers to an alkyl group, wherein at least one of the hydrogen atoms of the alkyl group has been replaced by a halogen atom, preferably fluoro. Preferably, "haloalkyl" refers to an alkyl group wherein 1, 2 or 3 hydrogen atoms of the alkyl group have been replaced by a halogen atom, most preferably fluoro. Particularly preferred, yet non-limiting examples of haloalkyl are trifluoromethyl and trifluoroethyl.

The term "alkoxyalkyl" refers to an alkyl group, wherein at least one of the hydrogen atoms of the alkyl group has been replaced by an alkoxy group. Preferably, "alkoxyalkyl" refers to an alkyl group wherein 1, 2 or 3 hydrogen atoms, most preferably one hydrogen atom of the alkyl group have been replaced by an alkoxy group. A particularly preferred, yet non-limiting example of alkoxyalkyl is 2-methoxyethyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, particularly hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein.

Particularly preferred pharmaceutically acceptable salts of compounds of formula (I) are the salts of hydrochloric acid, hydrobromic acid, sulfuric acid, phosphoric acid and methanesulfonic acid.

The term "protecting group" (PG) denotes the group which selectively blocks a reactive site in a multifunctional compound such that a chemical reaction can be carried out selectively at another unprotected reactive site in the meaning conventionally associated with it in synthetic chemistry. Protective groups can be removed at the appropriate point. Exemplary protective groups are amino-protective groups, carboxy-protective groups or hydroxy-protective groups. Particular protective groups are the tert-butoxycarbonyl (Boc), benzyloxycarbonyl (Cbz), fluorenylmethoxycarbonyl (Fmoc) and benzyl (Bn). Further particular protective groups are the tert-butoxycarbonyl (Boc) and the fluorenylmethoxycarbonyl (Fmoc). More particular protective group is the tert-butoxycarbonyl (Boc). Exemplary protective groups and their application in organic synthesis are described, for example, in "Protective Groups in Organic Chemistry" by T. W. Greene and P. G. M. Wutts, 5th Ed., 2014, John Wiley & Sons, N.Y.

The terms "asymmetric carbon atom" and "asymmetric center" mean a carbon atom with four different substituents. According to the Cahn-Ingold-Prelog Convention, an asymmetric carbon atom can be of the "R" or "S" configuration.

Compounds

In a first aspect, the present invention provides a compound of formula (I)

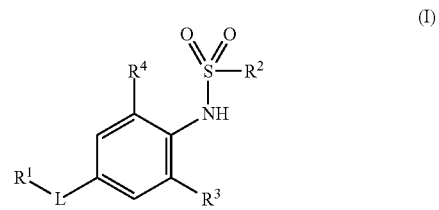

wherein

L is a bond or —C≡C—;

$R^1$ is phenyl optionally substituted with 1 or 2 substituents independently selected from halogen, hydroxy, lower alkyl, lower alkoxy or haloalkyl; or
  pyridyl optionally substituted with halogen, lower alkyl, lower alkoxy or haloalkyl; or
  pyrazolyl optionally substituted with halogen, hydroxy, lower alkyl, lower alkoxy or haloalkyl;

$R^2$ is phenyl optionally substituted with 1 to 3 substituents selected from halogen, hydroxy, lower alkyl, lower alkoxy, haloalkyl or alkoxyalkyl; or
  a heteroaryl group optionally substituted with halogen, hydroxy, lower alkyl, lower alkoxy, haloalkyl or alkoxyalkyl, selected from

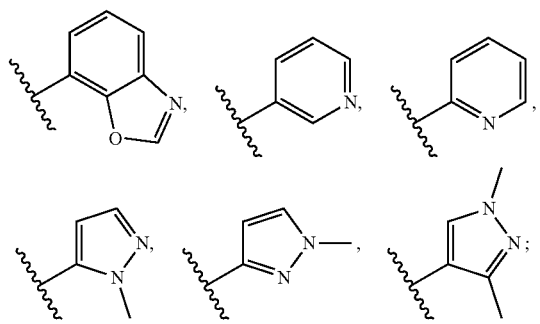

$R^3$ and $R^4$ are halogen, haloalkyl, lower alkyl or lower alkoxy;

or a pharmaceutically acceptable salt thereof.

In one embodiment, L is —C≡C—.

In one embodiment, there is provided a compound of formula (I) as described herein, or a pharmaceutically acceptable salt thereof, wherein $R^1$ is a group selected from

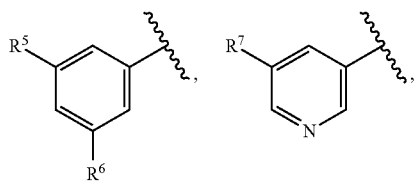

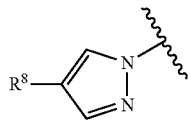

wherein
$R^5$ is hydrogen or halogen;
$R^6$ is hydrogen, halogen, hydroxy, lower alkyl or lower alkoxy;
$R^7$ is hydrogen or halogen;
$R^8$ is hydrogen, hydroxy or lower alkyl.

In one embodiment, there is provided a compound of formula (I) as described herein, or a pharmaceutically acceptable salt thereof, wherein $R^1$ is phenyl or pyridyl selected from

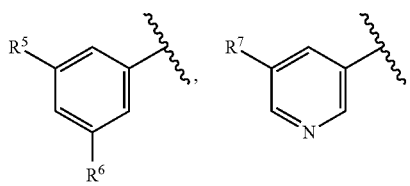

wherein
$R^5$ is hydrogen or halogen;
$R^6$ is hydrogen, halogen or hydroxy;
$R^7$ is hydrogen or halogen.

In one embodiment, there is provided a compound of formula (I) as described herein, or a pharmaceutically acceptable salt thereof, wherein $R^1$ is phenyl or pyridyl selected from

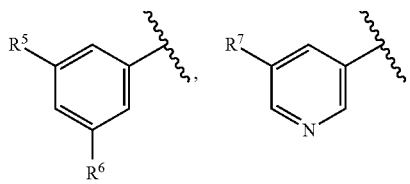

wherein
$R^5$ is hydrogen or fluorine;
$R^6$ is hydrogen, fluorine, chlorine or hydroxy;
$R^7$ is hydrogen or fluorine.

In one embodiment, there is provided a compound of formula (I) as described herein, or a pharmaceutically acceptable salt thereof, wherein $R^2$ is a group selected from

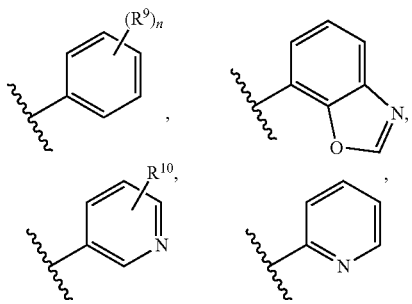

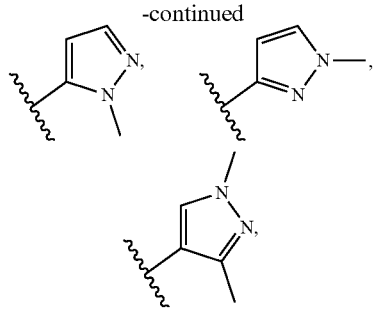

wherein
$R^9$ is halogen, lower alkyl, lower alkoxy, haloalkyl or alkoxyalkyl;
$R^{10}$ is hydrogen, halogen or lower alkyl;
n is 1, 2 or 3;
or a pharmaceutically acceptable salt thereof.

In one embodiment, there is provided a compound of formula (I) as described herein, or a pharmaceutically acceptable salt thereof, wherein $R^2$ is phenyl or pyrazolyl selected from

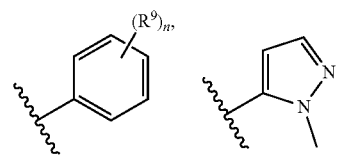

wherein
$R^9$ is halogen, lower alkyl or lower alkoxy;
n is 1, 2 or 3.

In a further embodiment, there is provided a compound of formula (I) as described herein, or a pharmaceutically acceptable salt thereof, wherein $R^2$ is phenyl or pyrazolyl selected from

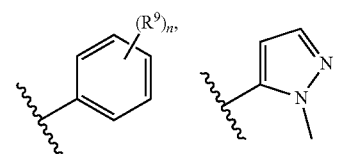

wherein
$R^9$ is chlorine, fluorine, methyl or methoxy;
n is 1, 2 or 3.

In a further embodiment, there is provided a compound of formula (I) as described herein, or a pharmaceutically acceptable salt thereof, wherein $R^3$ and $R^4$ are halogen.

In a preferred embodiment, there is provided a compound of formula (I) as described herein, or a pharmaceutically acceptable salt thereof, wherein $R^3$ and $R^4$ are fluorine.

In a further embodiment, there is provided a compound of formula (I) as described herein, or a pharmaceutically acceptable salt thereof, wherein L is —C≡C—;
R$^1$ is a group selected from

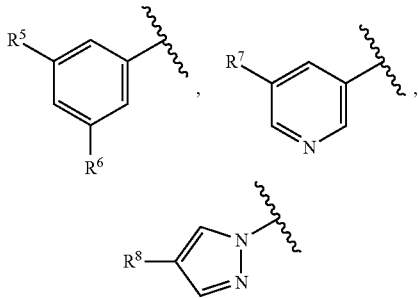

wherein
R$^5$ is hydrogen or halogen;
R$^6$ is hydrogen, halogen, hydroxy, lower alkyl or lower alkoxy;
R$^7$ is hydrogen or halogen;
R$^8$ is hydrogen, hydroxy or lower alkyl;
R$^2$ is a group selected from

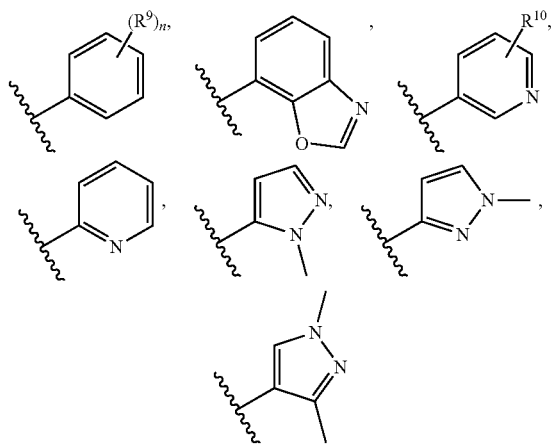

wherein
R$^9$ is halogen, lower alkyl, lower alkoxy, lower alkyl substituted by halogen or alkoxyalkyl;
R$^{10}$ is hydrogen, halogen or lower alkyl;
n is 1, 2 or 3;
R$^3$ and R$^4$ are halogen.

In a further embodiment, there is provided a compound of formula (I) as described herein, or a pharmaceutically acceptable salt thereof, wherein
L is —C≡C—;
R$^1$ is phenyl or pyridyl selected from

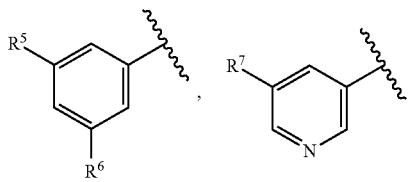

wherein
R$^5$ is hydrogen or halogen;
R$^6$ is hydrogen, halogen or hydroxy;
R$^7$ is hydrogen or halogen;
R$^2$ is phenyl or pyrazolyl selected from

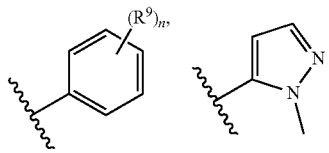

wherein
R$^9$ is halogen, lower alkyl or lower alkoxy;
n is 1, 2 or 3;
R$^3$ and R$^4$ are halogen.

In a further embodiment, there is provided a compound of formula (I) as described herein, or a pharmaceutically acceptable salt thereof, wherein
L is —C≡C—;
R$^1$ is phenyl or pyridyl selected from

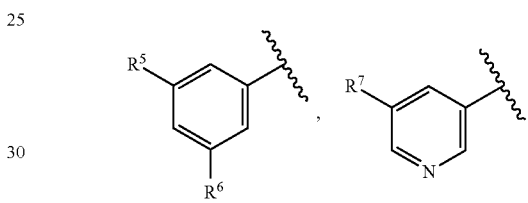

wherein
R$^5$ is hydrogen or fluorine;
R$^6$ is hydrogen, fluorine, chlorine or hydroxy;
R$^7$ is hydrogen or fluorine;
R$^2$ is phenyl or pyrazolyl selected from

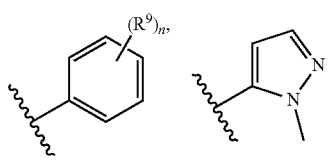

wherein
R$^9$ is chlorine, fluorine, methyl or methoxy;
n is 1, 2 or 3;
R$^3$ and R$^4$ are fluorine.

The compounds of formula (I), or pharmaceutically acceptable salts thereof, may contain one or more asymmetric centers and can be present in the form of optically pure enantiomers, mixtures of enantiomers such as, for example, racemates, mixtures of diastereoisomers, diastereoisomeric racemates or mixtures of diastereoisomeric racemates.

In a further embodiment, there is provided a compound of formula (I) as described herein, selected from:
2-chloro-N-[2,6-difluoro-4-(2-phenylethynyl)phenyl]benzenesulfonamide;
2,3-dichloro-N-[2,6-difluoro-4-(2-phenylethynyl)phenyl]benzenesulfonamide;
N-[2,6-difluoro-4-(2-phenylethynyl)phenyl]-2-(trifluoromethyl)benzenesulfonamide;
2,5-dichloro-N-[2,6-difluoro-4-(2-phenylethynyl)phenyl]benzenesulfonamide;

N-[2,6-difluoro-4-(2-phenylethynyl)phenyl]-2-methyl-benzenesulfonamide;
N-[2,6-difluoro-4-(2-phenylethynyl)phenyl]-2-fluoro-benzenesulfonamide;
N-[2,6-difluoro-4-(2-phenylethynyl)phenyl]pyridine-3-sulfonamide;
3-chloro-N-[2,6-difluoro-4-(2-phenylethynyl)phenyl]benzenesulfonamide;
2-chloro-N-[2,6-difluoro-4-[2-(3-pyridyl)ethynyl]phenyl]benzenesulfonamide;
N-[2,6-difluoro-4-(2-phenylethynyl)phenyl]pyridine-2-sulfonamide;
2,4-dichloro-N-[2,6-difluoro-4-(2-phenylethynyl)phenyl]benzenesulfonamide;
2-chloro-N-[2,6-difluoro-4-[2-(5-fluoro-3-pyridyl)ethynyl]phenyl]benzenesulfonamide;
2,3-dichloro-N-[2,6-difluoro-4-[2-(5-fluoro-3-pyridyl)ethynyl]phenyl]benzenesulfonamide;
3-chloro-N-[2,6-difluoro-4-[2-(5-fluoro-3-pyridyl)ethynyl]phenyl]benzenesulfonamide;
3-chloro-N-[2,6-difluoro-4-[2-(5-fluoro-3-pyridyl)ethynyl]phenyl]-2-methoxy-benzenesulfonamide;
2-chloro-N-[2,6-difluoro-4-(2-phenylethynyl)phenyl]-3-methyl-benzenesulfonamide;
2-chloro-N-[2,6-difluoro-4-(2-phenylethynyl)phenyl]-3-fluoro-benzenesulfonamide;
2-chloro-N-[2,6-difluoro-4-(2-phenylethynyl)phenyl]-5-methoxy-benzenesulfonamide;
2-chloro-N-[2,6-difluoro-4-(2-phenylethynyl)phenyl]-5-methyl-benzenesulfonamide;
3-chloro-N-[2,6-difluoro-4-(2-phenylethynyl)phenyl]-2-methyl-benzenesulfonamide;
3-chloro-N-[2,6-difluoro-4-(2-phenylethynyl)phenyl]-2-(trifluoromethyl)benzenesulfonamide;
2-chloro-N-[2,6-difluoro-4-(2-phenylethynyl)phenyl]pyridine-3-sulfonamide;
5-chloro-N-[2,6-difluoro-4-(2-phenylethynyl)phenyl]pyridine-3-sulfonamide;
N-[2,6-difluoro-4-(2-phenylethynyl)phenyl]-5-fluoropyridine-3-sulfonamide;
N-[2,6-difluoro-4-(2-phenylethynyl)phenyl]-1-methyl-1H-pyrazole-5-sulfonamide;
N-[2,6-difluoro-4-(2-phenylethynyl)phenyl]-1-methyl-pyrazole-3-sulfonamide;
2-chloro-N-[2,6-difluoro-4-(2-phenylethynyl)phenyl]-3-methoxy-benzenesulfonamide;
N-[2,6-difluoro-4-(2-phenylethynyl)phenyl]-2-methyl-3-(trifluoromethyl)benzenesulfonamide;
N-[2,6-difluoro-4-(2-phenylethynyl)phenyl]-2-methyl-pyridine-3-sulfonamide;
N-[2,6-difluoro-4-(2-phenylethynyl)phenyl]-2,5-dimethyl-benzenesulfonamide;
N-[2,6-difluoro-4-(2-phenylethynyl)phenyl]-4-methyl-pyridine-3-sulfonamide;
3-chloro-N-[2,6-difluoro-4-(2-phenylethynyl)phenyl]-2-(methoxymethyl)benzenesulfonamide;
2-chloro-N-[2,6-difluoro-4-(2-phenylethynyl)phenyl]-3-(trifluoromethyl)benzenesulfonamide;
N-[2,6-difluoro-4-(2-phenylethynyl)phenyl]-1,3-benzoxazole-7-sulfonamide;
3-chloro-N-[2,6-difluoro-4-(2-phenylethynyl)phenyl]-2-fluoro-benzenesulfonamide;
N-(2,6-difluoro-4-(phenylethynyl)phenyl)-3-methylbenzenesulfonamide;
N-[2,6-difluoro-4-(2-phenylethynyl)phenyl]-3-fluoro-2-methyl-benzenesulfonamide;
N-[2,6-difluoro-4-[2-(5-fluoro-3-pyridyl)ethynyl]phenyl]-3-fluoro-2,5-dimethyl-benzenesulfonamide; 2,2,2-trifluoroacetic acid salt;
N-[2,6-difluoro-4-[2-(5-fluoro-3-pyridyl)ethynyl]phenyl]-2-methyl-pyrazole-3-sulfonamide 2,2,2-trifluoroacetic acid salt;
N-[2,6-difluoro-4-(2-phenylethynyl)phenyl]-3-fluoro-2,5-dimethyl-benzenesulfonamide;
N-[2,6-difluoro-4-(2-phenylethynyl)phenyl]-1,3-dimethyl-pyrazole-4-sulfonamide; 2,2,2-trifluoroacetic acid salt;
3-chloro-N-[2,6-difluoro-4-[2-(3-methoxyphenyl)ethynyl]phenyl]-2-methyl-benzenesulfonamide;
3-chloro-N-[2,6-difluoro-4-[2-(3-fluorophenyl)ethynyl]phenyl]-2-methyl-benzenesulfonamide;
3-chloro-N-[4-[2-(3-chlorophenyl)ethynyl]-2,6-difluoro-phenyl]-2-methyl-benzenesulfonamide;
N-[2,6-difluoro-4-[2-(3-fluorophenyl)ethynyl]phenyl]-3-fluoro-2,5-dimethyl-benzenesulfonamide;
N-[2,6-difluoro-4-(2-phenylethynyl)phenyl]-3-fluoro-2-methoxy-benzenesulfonamide;
N-[2,6-difluoro-4-[2-(3-methoxyphenyl)ethynyl]phenyl]-3-fluoro-2,5-dimethyl-benzenesulfonamide;
N-[4-[2-(3-chlorophenyl)ethynyl]-2,6-difluoro-phenyl]-3-fluoro-2,5-dimethyl-benzenesulfonamide;
N-[4-[2-(3,5-difluorophenyl)ethynyl]-2,6-difluoro-phenyl]-3-fluoro-2,5-dimethyl-benzenesulfonamide;
N-[2,6-difluoro-4-[2-(3-pyridyl)ethynyl]phenyl]-3-fluoro-2,5-dimethyl-benzenesulfonamide;
N-[2,6-difluoro-4-[2-(m-tolyl)ethynyl]phenyl]-3-fluoro-2,5-dimethyl-benzenesulfonamide;
3-chloro-N-[2,6-difluoro-4-[2-(5-fluoro-3-pyridyl)ethynyl]phenyl]-2-methyl-benzenesulfonamide;
3-chloro-N-[2,6-difluoro-4-[2-(5-fluoro-3-pyridyl)ethynyl]phenyl]-5-fluoro-2-methyl-benzenesulfonamide;
3-chloro-N-(2,6-difluoro-4-((5-fluoropyridin-3-yl)ethynyl)phenyl)-2,5-dimethylbenzenesulfonamide 2,2,2-trifluoroacetate;
3-chloro-N-(4-((5-chloropyridin-3-yl)ethynyl)-2,6-difluoro-phenyl)-2-methylbenzenesulfonamide;
3-chloro-N-[2,6-difluoro-4-[2-(5-methyl-3-pyridyl)ethynyl]phenyl]-2-methyl-benzenesulfonamide; 2,2,2-trifluoroacetic acid;
N-[2,6-difluoro-4-[2-(5-fluoro-3-pyridyl)ethynyl]phenyl]-3-fluoro-2-methyl-benzenesulfonamide 2,2,2-trifluoroacetic acid;
N-[4-(4-tert-butylpyrazol-1-yl)-2,6-difluoro-phenyl]-2-chloro-benzenesulfonamide;
N-[4-(4-tert-butylpyrazol-1-yl)-2,6-difluoro-phenyl]-2,3-dichloro-benzenesulfonamide;
N-[4-(4-tert-butylpyrazol-1-yl)-2,6-difluoro-phenyl]-3,5-dichloro-benzenesulfonamide; and
N-[2,6-difluoro-4-[2-(3-hydroxyphenyl)ethynyl]phenyl]-3-fluoro-2,5-dimethyl-benzenesulfonamide;
or a pharmaceutically acceptable salt thereof.

In a further embodiment, there is provided a compound of formula (I) as described herein, selected from:
2,3-dichloro-N-[2,6-difluoro-4-[2-(5-fluoro-3-pyridyl)ethynyl]phenyl]benzenesulfonamide;
3-chloro-N-[2,6-difluoro-4-[2-(5-fluoro-3-pyridyl)ethynyl]phenyl]benzenesulfonamide;
3-chloro-N-[2,6-difluoro-4-[2-(5-fluoro-3-pyridyl)ethynyl]phenyl]-2-methoxy-benzenesulfonamide;
2-chloro-N-[2,6-difluoro-4-(2-phenylethynyl)phenyl]-3-fluoro-benzenesulfonamide;
2-chloro-N-[2,6-difluoro-4-(2-phenylethynyl)phenyl]-5-methyl-benzenesulfonamide;

3-chloro-N-[2,6-difluoro-4-(2-phenylethynyl)phenyl]-2-methyl-benzenesulfonamide;
N-[2,6-difluoro-4-(2-phenylethynyl)phenyl]-1-methyl-1H-pyrazole-5-sulfonamide;
N-[2,6-difluoro-4-(2-phenylethynyl)phenyl]-3-fluoro-2-methyl-benzenesulfonamide;
N-[2,6-difluoro-4-[2-(5-fluoro-3-pyridyl)ethynyl]phenyl]-3-fluoro-2,5-dimethyl-benzenesulfonamide; 2,2,2-trifluoroacetic acid salt;
N-[2,6-difluoro-4-(2-phenylethynyl)phenyl]-3-fluoro-2,5-dimethyl-benzenesulfonamide;
3-chloro-N-[2,6-difluoro-4-[2-(3-fluorophenyl)ethynyl]phenyl]-2-methyl-benzenesulfonamide;
N-[2,6-difluoro-4-[2-(3-fluorophenyl)ethynyl]phenyl]-3-fluoro-2,5-dimethyl-benzenesulfonamide;
N-[2,6-difluoro-4-[2-(3-methoxyphenyl)ethynyl]phenyl]-3-fluoro-2,5-dimethyl-benzenesulfonamide;
N-[4-[2-(3-chlorophenyl)ethynyl]-2,6-difluoro-phenyl]-3-fluoro-2,5-dimethyl-benzenesulfonamide;
N-[4-[2-(3,5-difluorophenyl)ethynyl]-2,6-difluoro-phenyl]-3-fluoro-2,5-dimethyl-benzenesulfonamide;
N-[2,6-difluoro-4-[2-(3-pyridyl)ethynyl]phenyl]-3-fluoro-2,5-dimethyl-benzenesulfonamide;
3-chloro-N-[2,6-difluoro-4-[2-(5-fluoro-3-pyridyl)ethynyl]phenyl]-2-methyl-benzenesulfonamide;
3-chloro-N-[2,6-difluoro-4-[2-(5-fluoro-3-pyridyl)ethynyl]phenyl]-5-fluoro-2-methyl-benzenesulfonamide;
3-chloro-N-(2,6-difluoro-4-((5-fluoropyridin-3-yl)ethynyl)phenyl)-2,5-dimethylbenzenesulfonamide 2,2,2-trifluoroacetate;
N-[2,6-difluoro-4-[2-(5-fluoro-3-pyridyl)ethynyl]phenyl]-3-fluoro-2-methyl-benzenesulfonamide; 2,2,2-trifluoroacetic acid; and
N-[2,6-difluoro-4-[2-(3-hydroxyphenyl)ethynyl]phenyl]-3-fluoro-2,5-dimethyl-benzenesulfonamide;
or a pharmaceutically acceptable salt thereof.

Processes of Manufacturing

Processes for the manufacture of compounds of formula (I), or pharmaceutically acceptable salts thereof, as described herein are also an object of the present invention.

The preparation of compounds of formula (I) as described herein may be carried out in sequential or convergent synthetic routes. Syntheses of the invention are shown in the following general schemes. The skills required for carrying out the reactions and purifications of the resulting products are known to those skilled in the art. The substituents and indices used in the following description of the processes have the significance given herein before unless indicated to the contrary.

If one of the starting materials, intermediates or compounds of formula (I) contain one or more functional groups which are not stable or are reactive under the reaction conditions of one or more reaction steps, appropriate protecting groups (as described e.g. in "Protective Groups in Organic Chemistry" by T. W. Greene and P. G. M. Wuts, 3rd Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethylsilylethyl carbamate (Teoc), carbobenzyloxy (Cbz) and p-methoxybenzyloxycarbonyl (Moz).

If starting materials or intermediates contain stereogenic centers, compounds of formula (I) can be obtained as mixtures of diastereomers or enantiomers, which can be separated by methods well known in the art e.g., chiral HPLC, chiral SFC or chiral crystallization. Racemic compounds can, for example, be separated into their antipodes via diastereomeric salts by crystallization with optically pure acids or by separation of the antipodes by specific chromatographic methods using either a chiral adsorbent or a chiral eluent. It is equally possible to separate starting materials and intermediates containing stereogenic centers to afford diastereomerically/enantiomerically enriched starting materials and intermediates. Using such diastereomerically/enantiomerically enriched starting materials and intermediates in the synthesis of compounds of formula (I) will typically lead to the respective diastereomerically/enantiomerically enriched compounds of formula (I).

A person skilled in the art will acknowledge that the sequence of reactions may be varied depending on reactivity and nature of the intermediates.

In more detail, the compounds of formula (I) can be manufactured by the methods given below, by the methods given in the examples or by analogous methods. Appropriate reaction conditions for the individual reaction steps are known to a person skilled in the art. Also, for reaction conditions described in literature affecting the described reactions see for example: *Comprehensive Organic Transformations: A Guide to Functional Group Preparations,* 2nd Edition, Richard C. Larock. John Wiley & Sons, New York, N.Y. 1999). It was found convenient to carry out the reactions in the presence or absence of a solvent. There is no particular restriction on the nature of the solvent to be employed, provided that it has no adverse effect on the reaction or the reagents involved and that it can dissolve the reagents, at least to some extent. The described reactions can take place over a wide range of temperatures, and the precise reaction temperature is not critical to the invention. It is convenient to carry out the described reactions in a temperature range between −78° C. to reflux. The time required for the reaction may also vary widely, depending on many factors, notably the reaction temperature and the nature of the reagents. However, a period of from 0.5 hours to several days will usually suffice to yield the described intermediates and compounds. The reaction sequence is not limited to the one displayed in the schemes, however, depending on the starting materials and their respective reactivity, the sequence of reaction steps can be freely altered.

If starting materials or intermediates are not commercially available or their synthesis not described in literature, they can be prepared in analogy to existing procedures for close analogues or as outlined in the experimental section.

In one embodiment, compounds of formula (I), as described herein or a pharmaceutically acceptable salt thereof, may be prepared by a process comprising reacting an amine 1

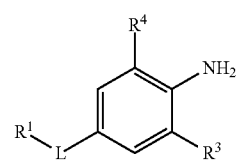

with a sulfonyl chloride 2

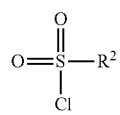

wherein R$^1$, R$^2$, R$^3$ and R$^4$ are as described herein, to form said compound of formula (I), and if desired, converting the compounds obtained into a pharmaceutically acceptable salt thereof.

In a further embodiment, the process according to the invention can be carried out under basic conditions, e.g. using pyridine or LiHMDS.

In one embodiment, compounds of formula (I) wherein R$^1$, R$^2$, R$^3$ and R$^4$ are as described herein and their intermediates may be prepared in analogy to literature procedures and/or depicted for example in schemes 1 to 7 respectively.

Compounds of formula (I), as described herein or a pharmaceutically acceptable salt thereof, may be prepared by reacting an amine of formula 1 with a sulfonyl chloride of formula 2 under basic conditions, for example using pyridine as solvent (elevated temperatures or nucleophilic catalysis (e.g. DMAP) can be used if required), or using LiHMDS in THF at low temperature (Scheme 1). Simpler sulfonamide building blocks such as 4 can also be generated using these methods.

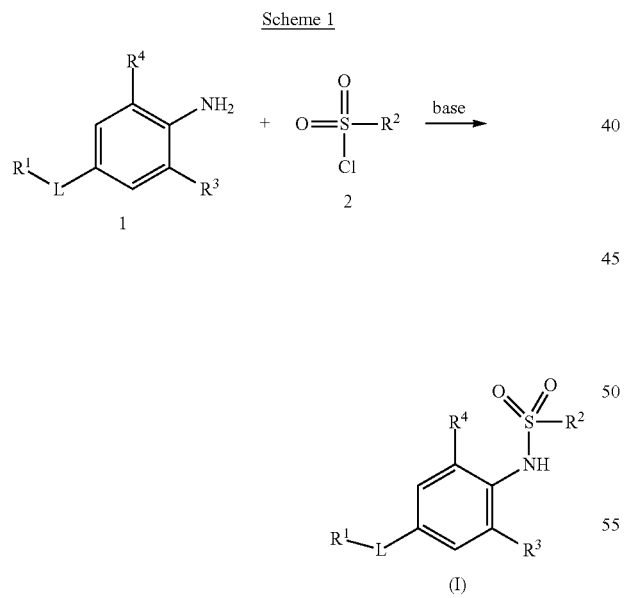

Alternatively, where L=alkyne triple bond, the compounds of formula (I) can be prepared using an alkyne derivative 3 and a suitably functionalised aryl precursor 4, using a transition-metal-catalyzed cross-coupling reaction, such as Sonogashira conditions (X=H, Y=Br, I) or sila-Sonogashira or Hiyama conditions (X=SiMe$_3$, Y=Br, I) (Scheme 2).

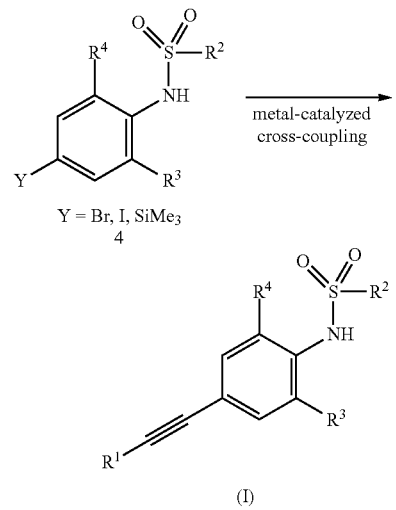

Alternatively, the directionality of the cross-coupling can be interchanged, such that compounds of formula (I) can be generated from a (hetero)aryl halide derivative 5 and an alkyne derivative 6, using a transition-metal-catalyzed cross-coupling reaction, such as Sonogashira conditions (X=H, Y=Br, I) or sila-Sonogashira or Hiyama conditions (X=SiMe$_3$, Y=Br, I) (Scheme 3).

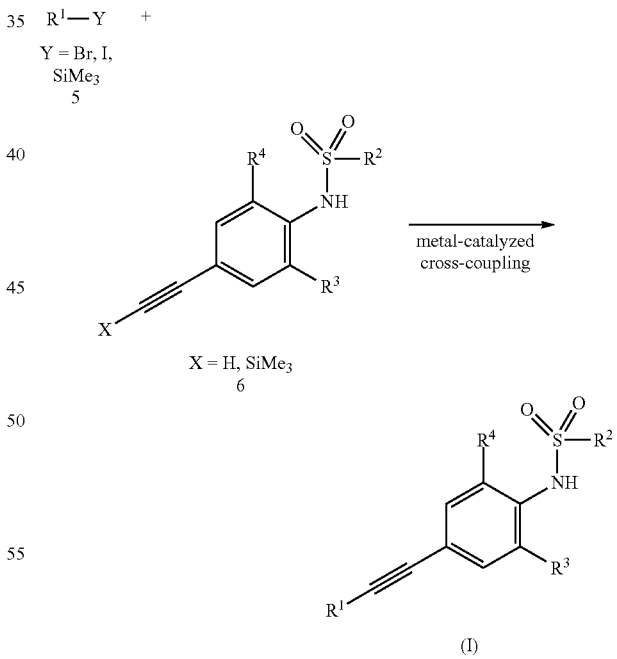

Aryl alkynylsilane building blocks (such as 3 and 6, where X=SiMe$_3$) can be generated from suitable arylhalide building blocks (such as 4 or 5, Y=Br, I) and trimethylsilylacetylene under Pd-catalysis (Sonogashira conditions).

Alternatively, where L=bond, and R$^1$=(substituted) N-linked heteroaryl, the compound of formula (I) can be generated using metal-catalyzed cross-coupling of an N—H heterocycle with a suitable aryl iodide derivative 4, for example Buchwald conditions or a copper-catalyzed cross-coupling. Alternatively, the N-linked heteroaryl $R^1$, can be constructed using standard heterocyclic synthesis techniques.

Where L=bond and $R^1$=(substituted) N-linked pyrazole, the compound of formula (I) can be generated by condensation of a dialdehyde derivative 10 with a hydrazino derivative 9. The hydrazino derivative 9 can be prepared from an amine derivative 8 via diazotization and reduction, and the amine can be prepared from a nitro derivative 7 via reduction (e.g. using iron powder) (Scheme 4). As in Scheme 1, the nitro derivatives 7 can be generated via reaction of a suitable nitro-aniline with a suitable sulfonyl chloride derivative 2 under basic conditions.

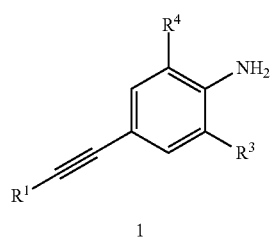

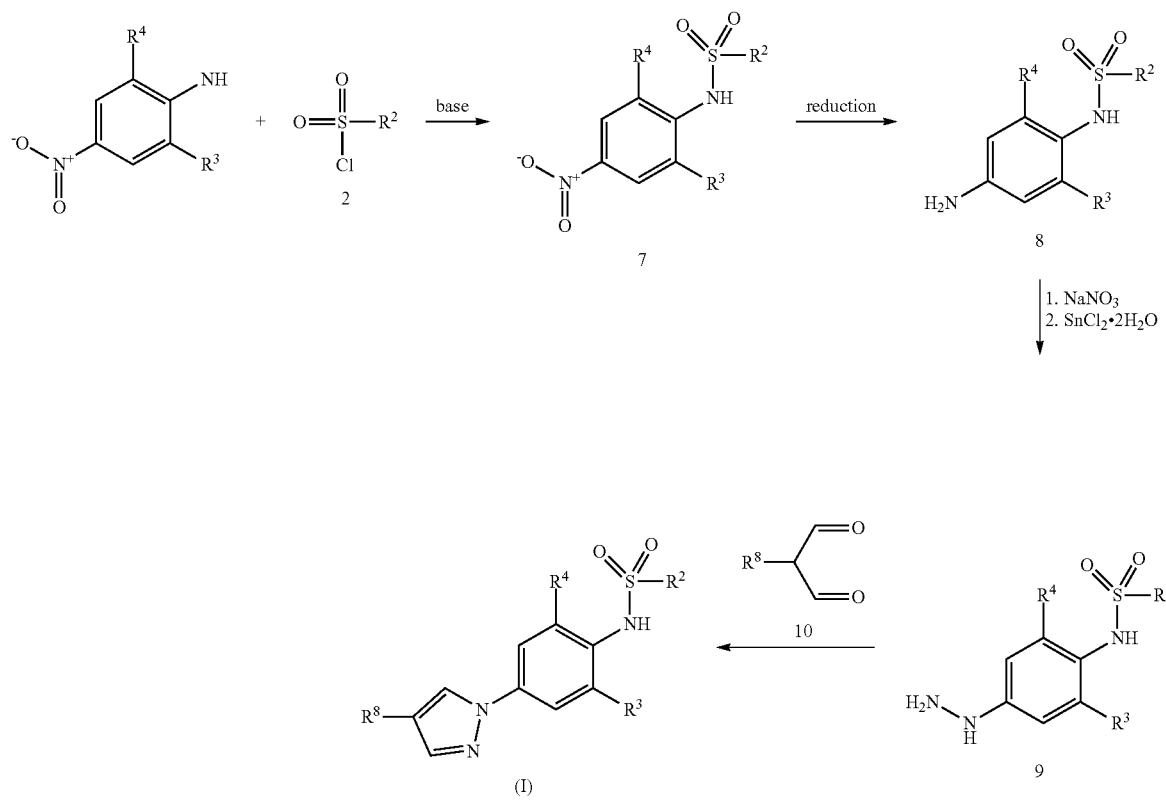

Building blocks of formula 1, may be synthesized from a suitable aryl iodide using a metal-catalyzed cross coupling reaction. In particular, where L=alkyne and $R^1$=(hetero)aryl, building blocks of formula 1 may be synthesized from an aryl iodide and a (hetero)arylalkyne under Sonogashira conditions. (Scheme 5)

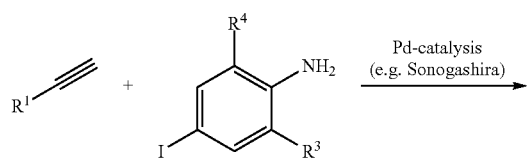

Non-commercial (hetero)arylsulfonyl chlorides of formula 2 can be generated from a suitable aryl halide (X=Br, I), for example by reacting with benzyl mercaptan under palladium catalysis to form a benzylsulfanyl derivative 11, which can be oxidised to the sulfonyl chloride (e.g. using N-chlorosuccinimide in AcOH). Alternatively the (hetero)aryl halide may be converted directly into the (hetero)arylsulfonyl chloride 2 via metal-halogen exchange (e.g. nBuLi or iPrMgCl) followed by reaction with $SO_2$ or DABSO (1,4-diazabicyclo[2.2.2]octane bis(sulfur dioxide) adduct) and oxidation (e.g. with sulfurylchloride or N-chlorosuccinimide). (Scheme 6)

Scheme 6

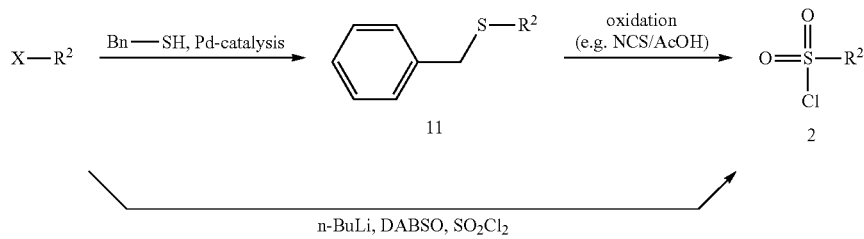

Alternatively (hetero)arylsulfonyl chlorides of formula 2 can be generated from a suitable nitroaryl compound 12 via reduction to the aniline 13 (e.g. using SnCl$_2$) and conversion to the sulfonyl chloride under Sandmeyer conditions (i.e. conversion to diazonium salt using NaNO$_2$, followed by reaction with SO$_2$ and CuCl). (Scheme 7)

Scheme 7

Pharmaceutical Composition and Administration

Another object of the present invention is a pharmaceutical composition comprising a compound of formula (I) as described herein, or a pharmaceutically acceptable salt thereof, and a pharmaceutically acceptable excipient.

The compounds of formula (I) and their pharmaceutically acceptable salts can be used as medicaments, in the form of pharmaceutical preparations. The pharmaceutical preparations can be administered internally, such as orally (e.g. in the form of tablets, coated tablets, dragées, hard and soft gelatine capsules, solutions, emulsions or suspensions), nasally (e.g. in the form of nasal sprays) or rectally (e.g. in the form of suppositories). However, the administration can also be effected parenterally, such as intramuscularly or intravenously (e.g. in the form of injection solutions). The administration can also be effected topically, e.g. transdermal administration, or in form of eye drops or ear drops.

The compounds of formula (I) and their pharmaceutically acceptable salts can be processed with pharmaceutically inert, inorganic or organic carriers for the production of pharmaceutical preparations, such as tablets, coated tablets, dragées, hard gelatin capsules, injection solutions or topical formulations. Lactose, corn starch or derivatives thereof, talc, stearic acids or salts thereof, and the like can be used, for example, as such carriers for tablets, coated tablets, dragées and hard gelatin capsules.

Suitable carriers for soft gelatin capsules are, for example, vegetable oils, waxes, fats, semi-solid substances and liquid polyols and the like. Depending on the nature of the active substance no carriers are, however, usually required in the case of soft gelatin capsules. Suitable carriers for the production of solutions and syrups are, for example, water, alcohols, polyols, saccharose, glucose, invert sugar, vegetable oil, and the like. Suitable carriers for injection solutions are, for example, water, alcohols, polyols, glycerol, vegetable oils, and the like. Suitable carriers for suppositories are, for example, natural or hardened oils, waxes, fats, semi-liquid or liquid polyols, and the like. Suitable carriers for topical ocular formulations are, for example, cyclodextrins, mannitol or many other carriers and excipients known in the art.

Moreover, the pharmaceutical preparations can contain preservatives, solubilizers, viscosity increasing substances, stabilizers, wetting agents, emulsifiers, sweeteners, colorants, flavorants, salts for varying the osmotic pressure, buffers, masking agents or antioxidants. They can also contain other therapeutically valuable substances.

Medicaments containing a compound of formula (I) or a pharmaceutically acceptable salt thereof and a pharmaceutically acceptable excipient are also an object of the present invention, as is a process for their production, which comprises bringing one or more compounds of formula (I) and/or pharmaceutically acceptable salts thereof and, if desired, one or more other therapeutically valuable substances into a galenical administration form together with one or more pharmaceutically acceptable excipients.

The dosage can vary within wide limits and will, of course, have to be adjusted to the individual requirements in each particular case. In general, in the case of oral administration a daily dosage of about 0.1 mg to 20 mg per kg body weight, preferably 0.5 mg to 4 mg per kg body weight (e.g. about 300 mg per person), divided into preferably 1-3 individual doses, which can consist, for example, of the same amounts, should be appropriate. In the case of topical administration, the formulation can contain 0.001% to 15% by weight of medicament and the required dose, which can be between 0.1 and 25 mg, and can be administered either by single dose per day or per week, or by multiple doses (2 to 4) per day, or by multiple doses per week. It will, however, be clear that the upper or lower limit given herein can be exceeded when this is shown to be indicated.

The pharmaceutical composition according to the invention may be prepared as follows.

Preparation of Pharmaceutical Compositions

| Tablet Formulation (Wet Granulation) | | | | |
|---|---|---|---|---|
| | mg/tablet | | | |
| Ingredient | 5 | 25 | 100 | 500 |
| 1) Compound of formula (I) | 5 | 25 | 100 | 500 |
| 2) Lactose Anhydrous DTG | 125 | 105 | 30 | 150 |

Tablet Formulation (Wet Granulation)

| Ingredient | mg/tablet | | | |
|---|---|---|---|---|
| | 5 | 25 | 100 | 500 |
| 3) Sta-Rx 1500 | 6 | 6 | 6 | 30 |
| 4) Microcrystalline Cellulose | 30 | 30 | 30 | 150 |
| 5) Magnesium Stearate | 1 | 1 | 1 | 1 |
| Total | 167 | 167 | 167 | 831 |

Manufacturing Procedure:
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Capsule Formulation

| Ingredient | mg/capsule | | | |
|---|---|---|---|---|
| | 5 | 25 | 100 | 500 |
| 1) Compound of formula (I) | 5 | 25 | 100 | 500 |
| 2) Hydrous Lactose | 159 | 123 | 148 | — |
| 3) Corn Starch | 25 | 35 | 40 | 70 |
| 4) Talc | 10 | 15 | 10 | 25 |
| 5) Magnesium Stearate | 1 | 2 | 2 | 5 |
| Total | 200 | 200 | 300 | 600 |

Manufacturing Procedure:
1. Mix ingredients 1, 2 and 3 in a suitable mixer for 30 minutes.
2. Add ingredients 4 and 5 and mix for 3 minutes.
3. Fill into a suitable capsule.

Injection Solutions

| Ingredient | mg/injection solution |
|---|---|
| Compound of formula I | 3 |
| Polyethylene Glycol 400 | 150 |
| acetic acid | q.s. ad pH 5.0 |
| water for injection solutions | ad 1.0 ml |

Manufacturing Procedure:

A compound of formula (I) is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Indications

Also an object of the present invention is a compound of formula (I) as described herein, or a pharmaceutically acceptable salt thereof, for use as therapeutically active substance.

As described above, compounds of formula (I) and their pharmaceutically acceptable salts are useful as mGluR4 negative allosteric modulators.

In one aspect, the present invention provides compounds of formula (I) as described herein, or a pharmaceutically acceptable salt thereof, for use in the therapeutic and/or prophylactic treatment of diseases associated with mGluR4, such as cancer, anxiety, emesis, obsessive compulsive disorder, autism, neuroprotection, Parkinson's disease, depression and diabetes type 2.

In a further aspect, the present invention provides the use of compounds of formula (I) as described herein, or a pharmaceutically acceptable salt thereof, for therapeutic and/or prophylactic treatment of diseases associated with mGluR4, such as cancer, anxiety, emesis, obsessive compulsive disorder, autism, neuroprotection, Parkinson's disease, depression and diabetes type 2.

In a further aspect, the present invention provides the use of compounds of formula (I) as described herein, or a pharmaceutically acceptable salt thereof, for the preparation of a medicament for the therapeutic and/or prophylactic treatment of diseases associated with mGluR4, such as cancer, anxiety, emesis, obsessive compulsive disorder, autism, neuroprotection, Parkinson's disease, depression and diabetes type 2.

In a further aspect, the present invention provides a method for the therapeutic and/or prophylactic treatment of diseases associated with mGluR4, such as cancer, anxiety, emesis, obsessive compulsive disorder, autism, neuroprotection, Parkinson's disease, depression and diabetes type 2, which method comprises administering an effective amount of a compound of formula (I) as described herein, or a pharmaceutically acceptable salt thereof.

EXAMPLES

The invention will be more fully understood by reference to the following examples. The claims should not, however, be construed as limited to the scope of the examples.

1) Preparative Examples

All reaction examples and intermediates were prepared under an argon atmosphere if not specified otherwise.

ABBREVIATIONS

AcOH=acetic acid, ACN=acetonitrile, Bn=benzyl, BINAP=(2,2'-bis(diphenylphosphino)-1,1'-binaphthyl), Boc=tert-butyloxycarbonyl, CAS RN=chemical abstracts registration number, Cbz=benzyloxycarbonyl, $Cs_2CO_3$=cesium carbonate, CO=carbon monoxide, CuCi=copper(I) chloride, CuCN=copper(I) cyanide, CuI=copper(I) iodide, DABCO=1,4-Diazabicyclo[2.2.2]octane;triethylenediamine, DAST=(diethylamino)sulfur trifluoride, DBU=1,8-diazabicyclo[5,4,0]undec-7-ene, DEAD=diethyl azodicarboxylate, DIAD=diisopropyl azodicarboxylate, DIBAL-H=diisobutyl aluminium hydride, DMAP=4-dimethylaminopyridine, DME=dimethoxyethane, DMEDA=N,N'-dimethylethylenediamine, DMF=N,N-dimethylformamide, DIPEA=N,N-diisopropylethylamine, dppf=1,1 bis(diphenyl phosphino)ferrocene, EDC.HCl=N-(3-dimethylaminopropyl)-N'-ethylcarbodiimide hydrochloride, EI=electron impact, ESI=electrospray ionization, EtOAc=ethyl acetate, EtOH=ethanol, h=hour(s), FA=formic acid, $H_2O$=water, $H_2SO_4$=sulfuric acid, HATU=1-[bis(dimethylamino)methylene]-1H-1,2,3-triazolo[4,5-b]pyridinium-3-oxide hexafluorophosphate, HBTU=O-benzotriazole-N,N,N',N'-tetramethyl-uronium-hexafluorophosphate, HCl=hydrogen chloride, HOBt=1-hydroxy-1H-benzotriazole; HPLC=high performance liquid chromatography, iPrMgCl=isopropylmagnesium chloride, 12=iodine, IPA=2-propanol, ISP=ion spray positive (mode), ISN=ion spray negative (mode), K₂CO₃=potassium carbonate, KHCO₃=potassium bicarbonate, KI=potassium iodide, KOH=potassium hydroxide, K₃PO₄=potassium phosphate tribasic, LiAlH₄ or LAH=lithium aluminium hydride, LiHMDS=lithium bis(trimethylsilyl)amide, LiGH=lithium hydroxide, mCPBA=meta-chloroperoxybenzoic acid, MgSO₄=magnesium sulfate, min=minute(s), mL=milliliter, MPLC=medium pressure liquid chromatography, MS=mass spectrum, nBuLi=n-butyllithium, NaBH₃CN=sodium cyanoborohydride, NaH=sodium hydride, NBS=N-bromosuccinimide, NaHCO₃=sodium hydrogen carbonate, NaNO₂=sodium nitrite, NaBH(OAc)₃=sodium triacetoxyborohydride, NaOH=sodium hydroxide, Na₂CO₃=sodium carbonate, Na₂SO₄=sodium sulfate, Na₂S₂O₃=sodium thiosulfate, NBS=N-bromosuccinimide, nBuLi=n-butyllithium, NEt₃=triethylamine (TEA), NH₄Cl=ammonium chloride, NMP=N-methyl-2-pyrrolidone, OAc=Acetoxy, T3P=propylphosphonic anhydride, PE=petroleum ether, PG=protective group, Pd-C=palladium on activated carbon, PdCl2(dppf)-CH₂Cl₂=1,1'-bis(diphenylphosphino)ferrocene-palladium(II)dichloride dichloromethane complex, Pd₂(dba)₃=tris(dibenzylideneacetone)dipalladium(0), Pd(OAc)₂=palladium(II) acetate, Pd(OH)₂=palladium hydroxide, Pd(PPh₃)₄=tetrakis(triphenylphosphine)palladium(0), PTSA=p-toluenesulfonic acid, R=any group, RP=reverse phase, RT=room temperature, SFC=Supercritical Fluid Chromatography, S-PHOS=2-dicyclohexylphosphino-2',6'-dimethoxybiphenyl, TBAI=tetra butyl ammonium iodine, TEA=triethylamine, TFA=trifluoroacetic acid, THF=tetrahydrofuran, TMEDA=N,N,N',N'-tetramethylethylenediamine, ZnCl₂=zinc chloride, Hal=halogen, prep-TLC=preparative thin layer chromatography Example 1

2-chloro-N-[2,6-difluoro-4-(2-phenylethynyl phenyl]benzenesulfonamide

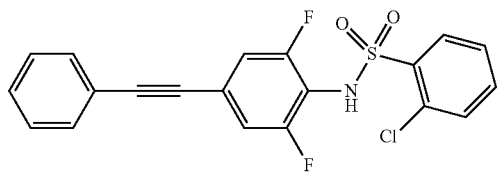 [SMILES: O=S(=O)(Nc1c(F)cc(C#Cc2ccccc2)cc1F)c1ccccc1Cl]

2,6-difluoro-4-(phenylethynyl)aniline (A.1) (100 mg, 436 μmol, Eq: 1.00) was combined with pyridine (1.5 mL) to give a yellow solution. 2-chlorobenzene-1-sulfonyl chloride (CAS: 2905-23-9) (113 mg, 72.8 μl, 524 μmol, Eq: 1.20) was added. The reaction mixture was heated to 22° C. and stirred for 20 h. The crude reaction mixture was concentrated in vacuo and purified by flash column chromatography, eluting with EtOAc in heptanes (0-30%) to give an initial product which was further purified by preparative HPLC to yield the title compound (27 mg, 15%) as a white solid. MS (ESI): m/z=402.2 [M−H]⁻.

Examples 2 to 15 of the following table were prepared in analogy to Example 1, using aniline and sulfonyl chloride building blocks. In some cases, the reaction was heated to 50° C., or DMAP was added as catalyst.

| Ex. | Structure | Systematic Name | Building Blocks | MS, ESI: m/z |
|---|---|---|---|---|
| 2 | 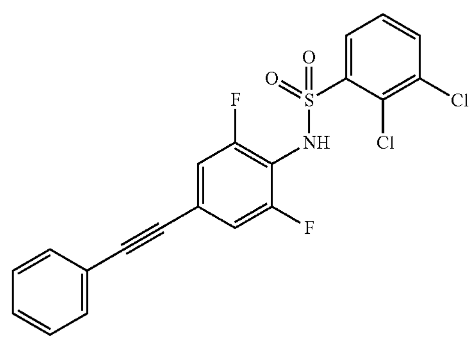 [SMILES: O=S(=O)(Nc1c(F)cc(C#Cc2ccccc2)cc1F)c1cccc(Cl)c1Cl] | 2,3-dichloro-N-[2,6-difluoro-4-(2-phenylethynyl)phenyl]benzenesulfonamide | A.1 and CAS 82417-45-6 | 436.2 [M − H]⁻ |
| 3 | 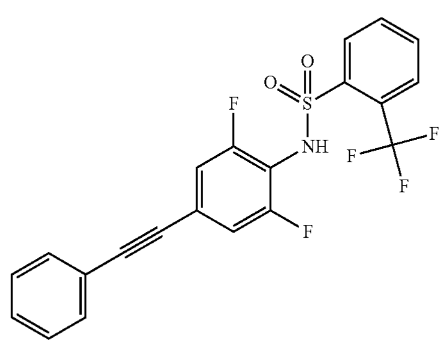 [SMILES: O=S(=O)(Nc1c(F)cc(C#Cc2ccccc2)cc1F)c1ccccc1C(F)(F)F] | N-[2,6-difluoro-4-(2-phenylethynyl)phenyl]-2-(trifluoromethyl)benzenesulfonamide | A.1 and CAS 776-04-5 | 436.6 [M − H]⁻ |

-continued

| Ex. | Structure | Systematic Name | Building Blocks | MS, ESI: m/z |
|---|---|---|---|---|
| 4 | 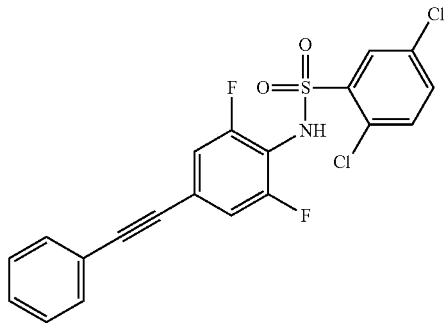 [SMILES: O=S(=O)(Nc1c(F)cc(C#Cc2ccccc2)cc1F)c1cc(Cl)ccc1Cl] | 2,5-dichloro-N-[2,6-difluoro-4-(2-phenylethynyl)phenyl]benzenesulfonamide | A.1 and CAS 5402-73-3 | 436.2 [M − H]⁻ |
| 5 | 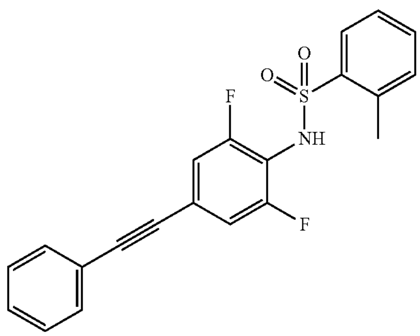 [SMILES: Cc1ccccc1S(=O)(=O)Nc1c(F)cc(C#Cc2ccccc2)cc1F] | N-[2,6-difluoro-4-(2-phenylethynyl)phenyl]-2-methyl-benzenesulfonamide | A.1 and CAS 133-59-5 | 382.2 [M − H]⁻ |
| 6 | 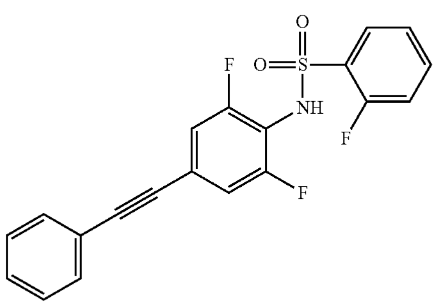 [SMILES: O=S(=O)(Nc1c(F)cc(C#Cc2ccccc2)cc1F)c1ccccc1F] | N-[2,6-difluoro-4-(2-phenylethynyl)phenyl]-2-fluoro-benzenesulfonamide | A.1 and CAS 2905-21-7 | 386.2 [M − H]⁻ |
| 7 | 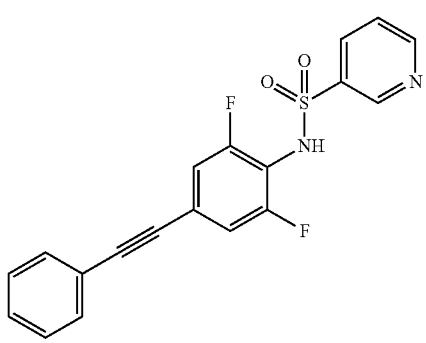 [SMILES: O=S(=O)(Nc1c(F)cc(C#Cc2ccccc2)cc1F)c1cccnc1] | N-[2,6-difluoro-4-(2-phenylethynyl)phenyl]pyridine-3-sulfonamide | A.1 and CAS 42899-76-3 | 369.2 [M − H]⁻ |

-continued

| Ex. | Structure | Systematic Name | Building Blocks | MS, ESI: m/z |
|---|---|---|---|---|
| 8 | 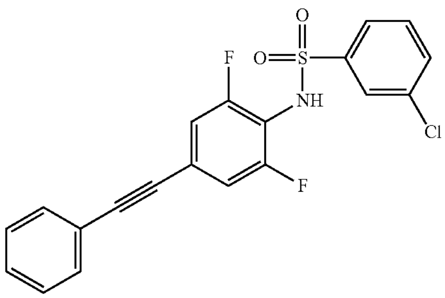 [SMILES: O=S(=O)(Nc1c(F)cc(C#Cc2ccccc2)cc1F)c1cccc(Cl)c1] | 3-chloro-N-[2,6-difluoro-4-(2-phenylethynyl)phenyl]benzenesulfonamide | A.1 and CAS 2888-06-4 | 402.3 [M − H]− |
| 9 | 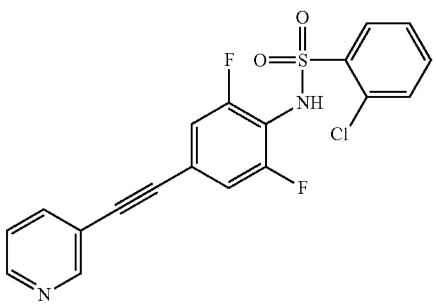 [SMILES: O=S(=O)(Nc1c(F)cc(C#Cc2cccnc2)cc1F)c1ccccc1Cl] | 2-chloro-N-[2,6-difluoro-4-[2-(3-pyridyl)ethynyl]phenyl]benzenesulfonamide | A.2 and CAS 2905-23-9 | 405.2 [M + H]+ |
| 10 | 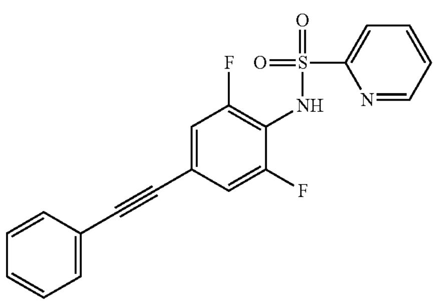 [SMILES: O=S(=O)(Nc1c(F)cc(C#Cc2ccccc2)cc1F)c1ccccn1] | N-[2,6-difluoro-4-(2-phenylethynyl)phenyl]pyridine-2-sulfonamide | A.1 and CAS 66715-65-9 | 369.3 [M − H]− |
| 11 | 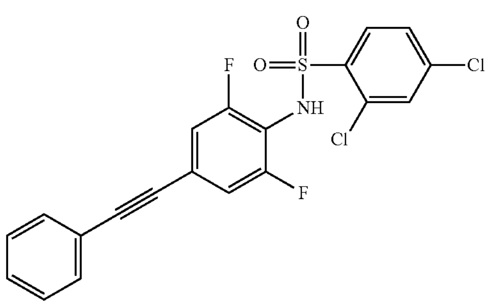 [SMILES: O=S(=O)(Nc1c(F)cc(C#Cc2ccccc2)cc1F)c1ccc(Cl)cc1Cl] | 2,4-dichloro-N-[2,6-difluoro-4-(2-phenylethynyl)phenyl]benzenesulfonamide | A.1 and CAS 16271-33-3 | 436.2 [M − H]− |
| 12 | 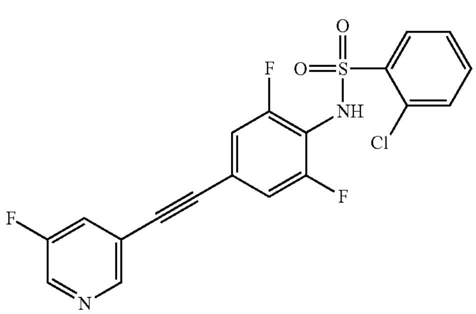 [SMILES: O=S(=O)(Nc1c(F)cc(C#Cc2cncc(F)c2)cc1F)c1ccccc1Cl] | 2-chloro-N-[2,6-difluoro-4-[2-(5-fluoro-3-pyridyl)ethynyl]phenyl]benzenesulfonamide | A.3 and CAS 2905-23-9 | 421.0 [M − H]− |

-continued

| Ex. | Structure | Systematic Name | Building Blocks | MS, ESI: m/z |
|---|---|---|---|---|
| 13 | 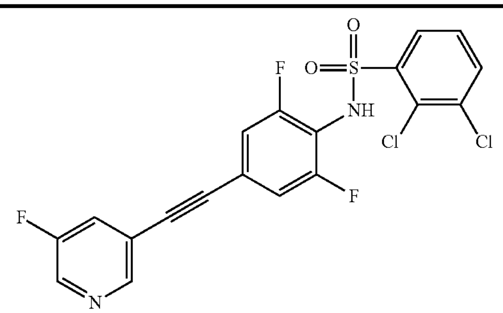 | 2,3-dichloro-N-[2,6-difluoro-4-[2-(5-fluoro-3-pyridyl)ethynyl]phenyl]benzenesulfonamide | A.3 and CAS 82417-45-6 | 455.0 [M − H]− |
| 14 | 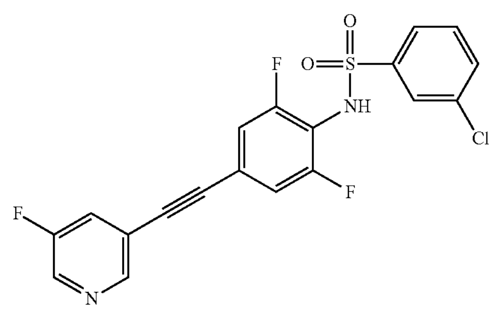 [SMILES: O=S(=O)(Nc1c(F)cc(C#Cc2cncc(F)c2)cc1F)c1cccc(Cl)c1] | 3-chloro-N-[2,6-difluoro-4-[2-(5-fluoro-3-pyridyl)ethynyl]phenyl]benzenesulfonamide | A.3 and CAS 2888-06-4 | 420.8 [M − H]− |
| 15 | 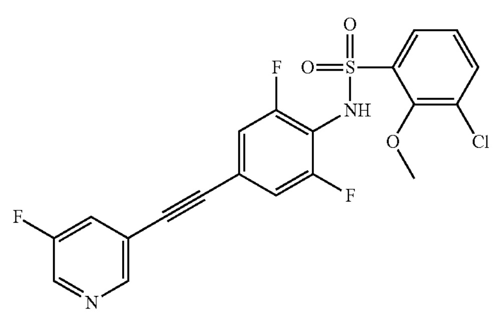 [SMILES: COc1c(Cl)cccc1S(=O)(=O)Nc1c(F)cc(C#Cc2cncc(F)c2)cc1F] | 3-chloro-N-[2,6-difluoro-4-[2-(5-fluoro-3-pyridyl)ethynyl]phenyl]-2-benzenesulfonamide | A.3 and CAS 847652-81-7 | 451.2 [M − H]− |

Example 16

2-chloro-N-[2,6-difluoro-4-(2-phenylethynyl)phenyl]-3-methyl-benzenesulfonamide

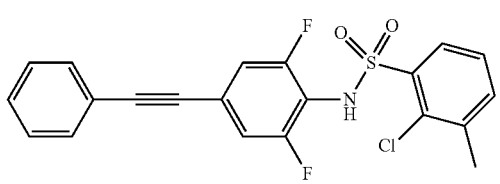 [SMILES: Cc1cccc(S(=O)(=O)Nc2c(F)cc(C#Cc3ccccc3)cc2F)c1Cl]

To a stirred solution of 2,6-Difluoro-4-phenylethynyl-phenylamine (70.0 mg, 0.3 mmol) and 2-chloro-3-methylbenzene-1-sulfonyl chloride (CAS: 1191545-47-7) (103.2 mg, 0.5 mmol) in THF (2 mL), LiHMDS (1 M in TTIF) (0.3 mL, 0.3 mmol) was added at −78° C. and stirred for 1 h at the same temp. After that the reaction mixture was allowed to attain at 25° C. temperature over a period of 1 h. Reaction was quenched by addition of water followed by extraction with ethyl acetate. The organic layer was dried over $Na_2SO_4$ and evaporated under reduced pressure to get the crude mass. The crude mass was purified by prep-HPLC method to get the title compound 2-chloro-N-[2,6-difluoro-4-(2-phenylethynyl)phenyl]-3-methylbenzene-1-sulfonamide (72.0 mg, 56%) as an off-white solid. MS (ESI): m/z=416.2 [M−H]−.

Examples 17 to 41 of the following table were prepared in analogy to Example 16, using aniline and sulfonyl chloride building blocks.

| Ex. | Structure | Systematic Name | Building Blocks | MS, ESI: m/z |
|---|---|---|---|---|
| 17 | 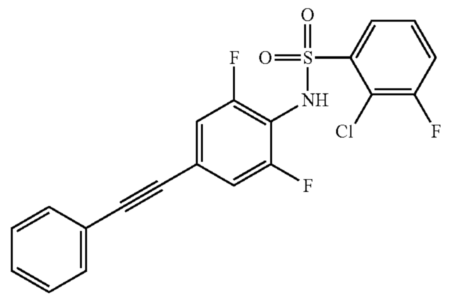 [SMILES: O=S(=O)(Nc1c(F)cc(C#Cc2ccccc2)cc1F)c1cccc(F)c1Cl] | 2-chloro-N-[2,6-difluoro-4-(2-phenylethynyl)phenyl]-3-fluoro-benzenesulfonamide | A.1 and CAS 5044024-79-7 | 420.2 [M − H]⁻ |
| 18 | 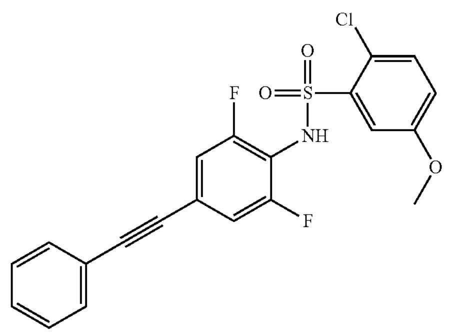 [SMILES: COc1ccc(Cl)c(S(=O)(=O)Nc2c(F)cc(C#Cc3ccccc3)cc2F)c1] | 2-chloro-N-[2,6-difluoro-4-(2-phenylethynyl)phenyl]-5-methoxy-benzenesulfonamide | A.1 and CAS 201935-41-3 | 432.1 [M − H]⁻ |
| 19 | 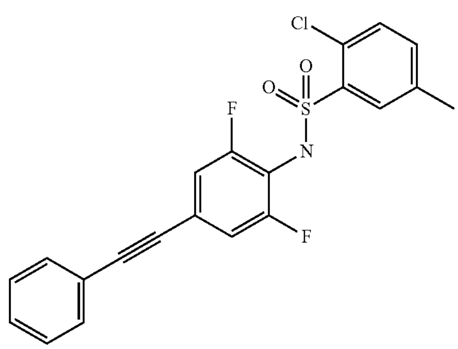 [SMILES: Cc1ccc(Cl)c(S(=O)(=O)Nc2c(F)cc(C#Cc3ccccc3)cc2F)c1] | 2-chloro-N-[2,6-difluoro-4-(2-phenylethynyl)phenyl]-5-methyl-benzenesulfonamide | A.1 and CAS 99876-69-4 | 416.1 [M − H]⁻ |
| 20 | 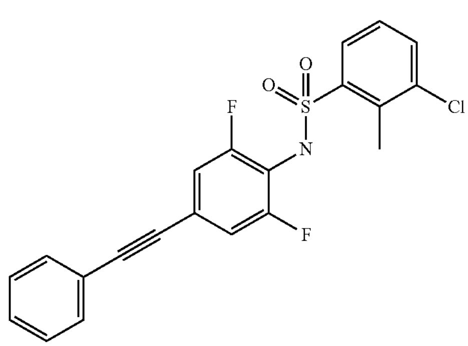 [SMILES: Cc1c(Cl)cccc1S(=O)(=O)Nc1c(F)cc(C#Cc2ccccc2)cc1F] | 3-chloro-N-[2,6-difluoro-4-(2-phenylethynyl)phenyl]-2-methyl-benzenesulfonamide | A.1 and CAS 80563-86-6 | 416.0 [M − H]⁻ |

| Ex. | Structure | Systematic Name | Building Blocks | MS, ESI: m/z |
|---|---|---|---|---|
| 21 | 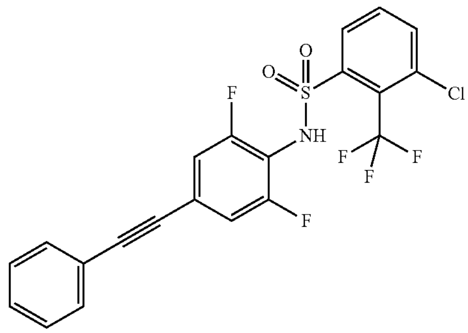 [SMILES: O=S(=O)(Nc1c(F)cc(C#Cc2ccccc2)cc1F)c1cccc(Cl)c1C(F)(F)F] | 3-chloro-N-[2,6-difluoro-4-(2-phenylethynyl)phenyl]-2-(trifluoromethyl)benzenesulfonamide | A.1 and CAS 1214340-24-5 | 469.9 [M − H]⁻ |
| 22 | 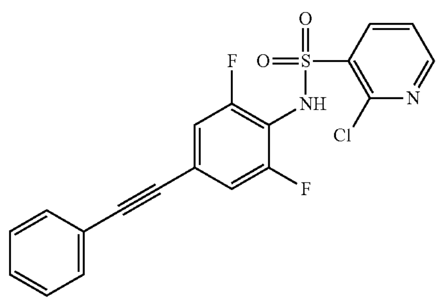 [SMILES: O=S(=O)(Nc1c(F)cc(C#Cc2ccccc2)cc1F)c1cccnc1Cl] | 2-chloro-N-[2,6-difluoro-4-(2-phenylethynyl)phenyl]pyridine-3-sulfonamide | A.1 and CAS 6684-06-6 | 403.2 [M − H]⁻ |
| 23 | 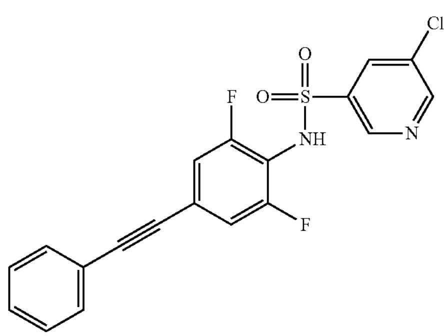 [SMILES: O=S(=O)(Nc1c(F)cc(C#Cc2ccccc2)cc1F)c1cncc(Cl)c1] | 5-chloro-N-[2,6-difluoro-4-(2-phenylethynyl)phenyl]pyridine-3-sulfonamide | A.1 and CAS 1060802-18-7 | 403.2 [M − H]⁻ |
| 24 | 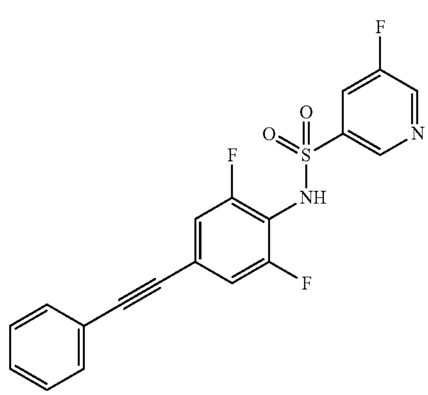 [SMILES: O=S(=O)(Nc1c(F)cc(C#Cc2ccccc2)cc1F)c1cncc(F)c1] | N-[2,6-difluoro-4-(2-phenylethynyl)phenyl]-5-fluoropyridine-3-sulfonamide | A.1 and CAS 1060802-49-4 | 387.2 [M − H]⁻ |

-continued

| Ex. | Structure | Systematic Name | Building Blocks | MS, ESI: m/z |
|---|---|---|---|---|
| 25 | 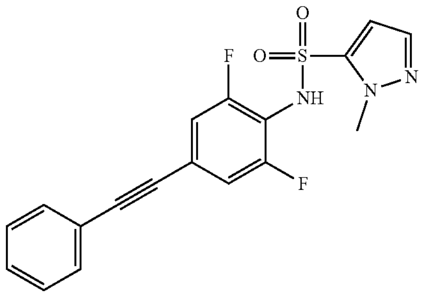 [SMILES: Cn1nccc1S(=O)(=O)Nc1c(F)cc(C#Cc2ccccc2)cc1F] | N-[2,6-difluoro-4-(2-phenylethynyl)phenyl]-1-methyl-1H-pyrazole-5-sulfonamide | A.1 and CAS 1020721-61-2 | 372.1 [M − H]− |
| 26 | 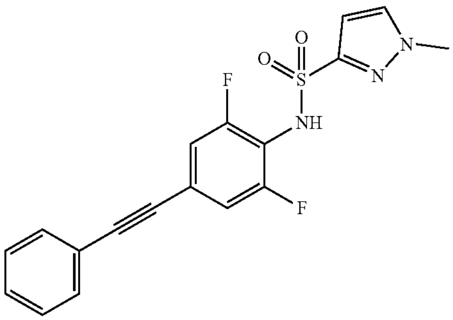 [SMILES: Cn1ccc(S(=O)(=O)Nc2c(F)cc(C#Cc3ccccc3)cc2F)n1] | N-[2,6-difluoro-4-(2-phenylethynyl)phenyl]-1-methyl-pyrazole-3-sulfonamide | A.1 and CAS 89501-90-6 | 372.1 [M − H]− |
| 27 | 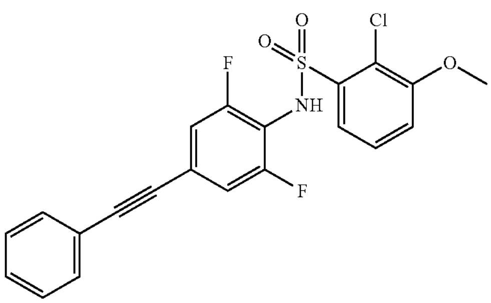 [SMILES: COc1cccc(S(=O)(=O)Nc2c(F)cc(C#Cc3ccccc3)cc2F)c1Cl] | 2-chloro-N-[2,6-difluoro-4-(2-phenylethynyl)phenyl]-3-methoxy-benzenesulfonamide | A.1 and B.1 | 432.1 [M − H]− |
| 28 | 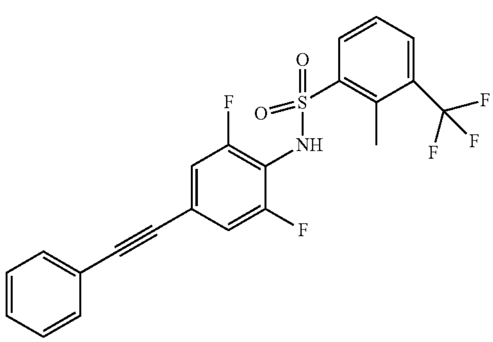 [SMILES: Cc1c(C(F)(F)F)cccc1S(=O)(=O)Nc1c(F)cc(C#Cc2ccccc2)cc1F] | N-[2,6-difluoro-4-(2-phenylethynyl)phenyl]-2-methyl-3-(trifluoromethyl benzenesulfonamide | A.1 and B.2 | 469.1 [M + NH$_3$ + H]+ |
| 29 | 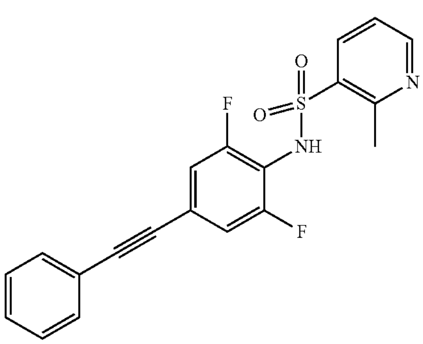 [SMILES: Cc1ncccc1S(=O)(=O)Nc1c(F)cc(C#Cc2ccccc2)cc1F] | N-[2,6-difluoro-4-(2-phenylethynyl)phenyl]-2-methyl-pyridine-3-sulfonamide | A.1 and B.3 | 385.1 [M + H]+ |

-continued

| Ex. | Structure | Systematic Name | Building Blocks | MS, ESI: m/z |
|---|---|---|---|---|
| 30 | 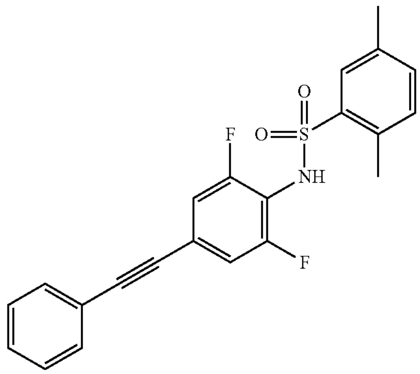 [SMILES: Cc1ccc(C)c(S(=O)(=O)Nc2c(F)cc(C#Cc3ccccc3)cc2F)c1] | N-[2,6-difluoro-4-(2-phenylethynyl)phenyl]-2,5-dimethyl-benzenesulfonamide | A.1 and CAS 19040-62-1 | 398.1 [M + H]+ |
| 31 | 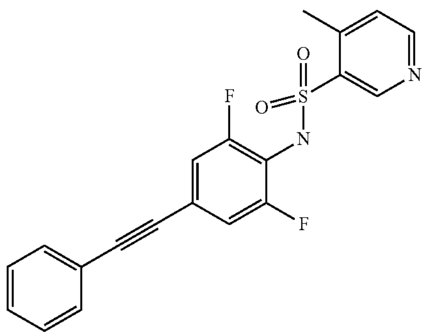 [SMILES: Cc1ccncc1S(=O)(=O)Nc1c(F)cc(C#Cc2ccccc2)cc1F] | N-[2,6-difluoro-4-(2-phenylethynyl)phenyl]-4-methyl-pyridine-3-sulfonamide | A.1 and B.4 | 385.1 [M + H]+ |
| 32 | 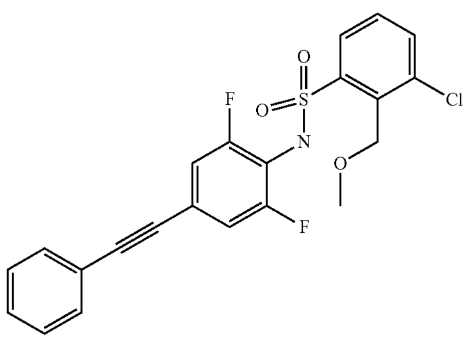 [SMILES: COCc1c(Cl)cccc1S(=O)(=O)Nc1c(F)cc(C#Cc2ccccc2)cc1F] | 3-chloro-N-[2,6-difluoro-4-(2-phenylethynyl)phenyl]-2-(methoxymethyl)benzenesulfonamide | A.1 and B.5 | 470.1 [M + Na]+ |
| 33 | 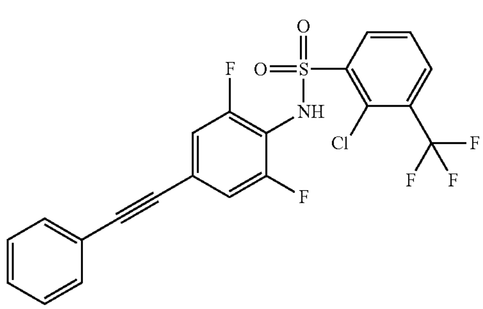 [SMILES: O=S(=O)(Nc1c(F)cc(C#Cc2ccccc2)cc1F)c1cccc(C(F)(F)F)c1Cl] | 2-chloro-N-[2,6-difluoro-4-(2-phenylethynyl)phenyl]-3-(trifluoromethyl)benzenesulfonamide | A.1 and B.6 | 494.0 [M + Na]+ |

-continued

| Ex. | Structure | Systematic Name | Building Blocks | MS, ESI: m/z |
|---|---|---|---|---|
| 34 | 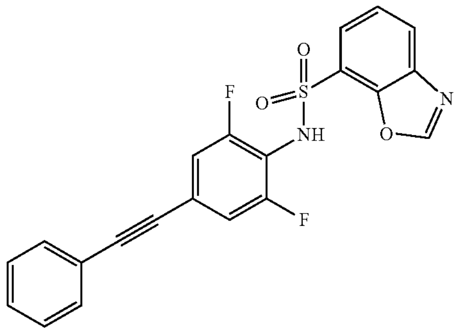 [SMILES: O=S(=O)(Nc1c(F)cc(C#Cc2ccccc2)cc1F)c1cccc2ncoc12] | N-[2,6-difluoro-4-(2-phenylethynyl)phenyl]-1,3-benzoxazole-7-sulfonamide | A.1 and B.7 | 411.0 [M + H]$^+$ |
| 35 | 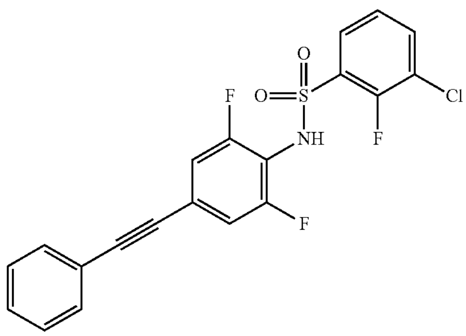 [SMILES: O=S(=O)(Nc1c(F)cc(C#Cc2ccccc2)cc1F)c1cccc(Cl)c1F] | 3-chloro-N-[2,6-difluoro-4-(2-phenylethynyl)phenyl]-2-fluoro-benzenesulfonamide | A.1 and CAS 351003-48-0 | 444.0 [M + Na]$^+$ |
| 36 | 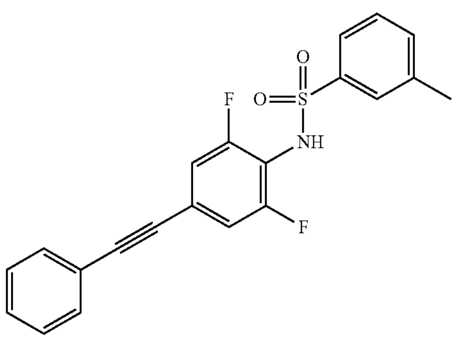 [SMILES: Cc1cccc(S(=O)(=O)Nc2c(F)cc(C#Cc3ccccc3)cc2F)c1] | -(2,6-difluoro-4-(phenylethynyl)phenyl)-3-methylbenzenesulfonamide | A.1 and CAS 1899-93-0 | 406.3 [M + Na]$^+$ |
| 37 | 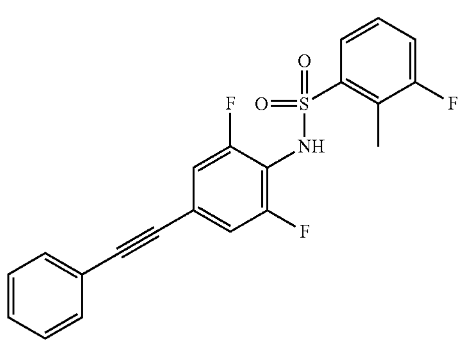 [SMILES: Cc1c(F)cccc1S(=O)(=O)Nc1c(F)cc(C#Cc2ccccc2)cc1F] | N-[2,6-difluoro-4-(2-phenylethynyl)phenyl]-3-fluoro-2-methyl-benzenesulfonamide | A.1 and CAS 875166-92-0 | 424.0 [M + Na]$^+$ |

-continued

| Ex. | Structure | Systematic Name | Building Blocks | MS, ESI: m/z |
|---|---|---|---|---|
| 38 | 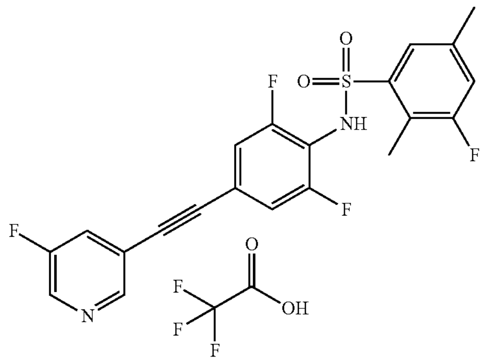 | N-[2,6-difluoro-4-[2-(5-fluoro-3-pyridyl)ethynyl]phenyl]-3-fluoro-2,5-dimethyl-benzenesulfonamide; 2,2,2-trifluoroacetic acid salt | A.3 and B.9 | 435.2 [M + H]$^+$ |
| 39 | 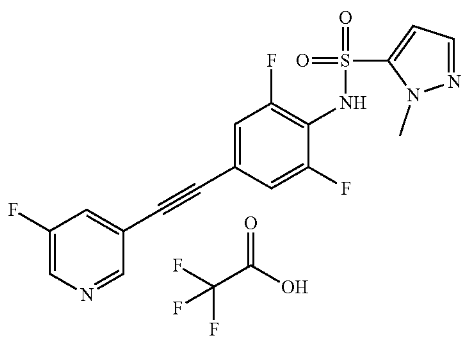 | N-[2,6-difluoro-4-[2-(5-fluoro-3-pyridyl)ethynyl]phenyl]-2-methyl-pyrazole-3-sulfonamide; 2,2,2-trifluoroacetic acid salt | A.3 and CAS 1020721-61-2 | 393.1 [M + H]$^+$ |
| 40 | 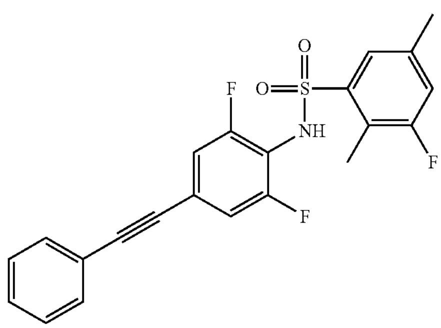 [SMILES: Cc1cc(F)c(C)c(S(=O)(=O)Nc2c(F)cc(C#Cc3ccccc3)cc2F)c1] | N-[2,6-difluoro-4-(2-phenylethynyl)phenyl]-3-fluoro-2,5-dimethyl-benzenesulfonamide | A.1 and B.9 | 433.2 [M + NH$_4$]$^+$ |
| 41 | 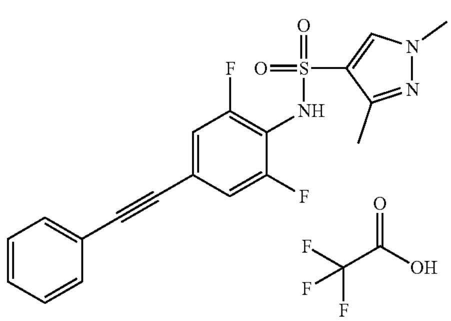 | N-[2,6-difluoro-4-(2-phenylethynyl)phenyl]-1,3-dimethyl-pyrazole-4-sulfonamide; 2,2,2-trifluoroacetic acid salt | A.1 and CAS 89501-93-9 | 388.2 [M + H]$^+$ |

Example 42

3-chloro-N-[2,6-difluoro-4-[2-(3-methoxyphenyl)ethynyl]phenyl]-2-methyl-benzenesulfonamide

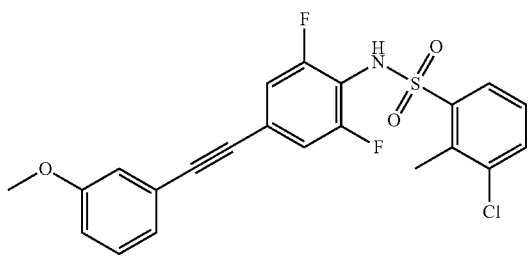 [SMILES: COc1cccc(C#Cc2cc(F)c(NS(=O)(=O)c3cccc(Cl)c3C)c(F)c2)c1]

A solution of 3-ethynylanisole (89 mg, 0.680 mmol), 3-chloro-N-(2,6-difluoro-4-iodo-phenyl)-2-methyl-benzenesulfonamide (B.8) (200 mg, 0.450 mmol), cuprous iodide (9 mg, 0.050 mmol), Pd(dppf)Cl$_2$ (16.5 mg, 0.020 mmol) and triethylamine (0.09 mL, 0.680 mmol) in N,N-dimethylformamide (5 mL) was stirred at 80° C. for 12 h. The mixture was diluted with water (10 mL) and extracted with ethyl acetate (20 mL×3). The combined organic phase was washed by brine (10 mL), dried over anhydrous sodium sulfate, filtered and concentrated under reduced pressure to give a residue. The residue was purified by prep-HPLC (FA) and lyophilized to give 3-chloro-N-[2,6-difluoro-4-[2-(3-methoxyphenyl)ethynyl]phenyl]-2-methyl-benzenesulfonamide (130 mg, 0.290 mmol, 64.3% yield) as light yellow solid. MS (ESI+): m/z=448.2 [M+H]$^+$ Examples 43 to 51 of the following table were prepared in analogy to Example 42, using a sulfonamide building block B.X and following alkyne building blocks.

| Ex. | Structure | Systematic Name | Building Blocks | MS, ESI: m/z |
|---|---|---|---|---|
| 43 | 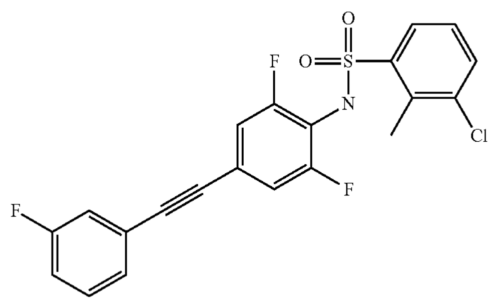 [SMILES: Cc1c(Cl)cccc1S(=O)(=O)Nc1c(F)cc(C#Cc2cccc(F)c2)cc1F] | 3-chloro-N-[2,6-difluoro-4-[2-(3-fluorophenyl)ethynyl]phenyl]-2-methyl-benzenesulfonamide | B.8 and 3-fluorophenyl acetylene | 453.1 [M + NH$_4$]$^+$ |
| 44 | 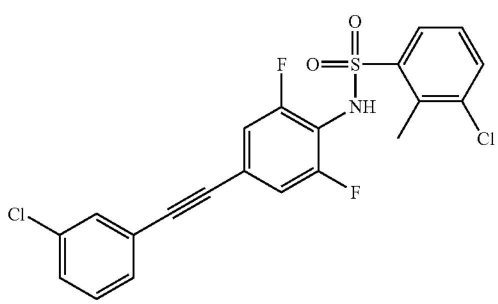 [SMILES: Cc1c(Cl)cccc1S(=O)(=O)Nc1c(F)cc(C#Cc2cccc(Cl)c2)cc1F] | 3-chloro-N-[4-[2-(3-chlorophenyl)ethynyl]-2,6-difluoro-phenyl]-2-methyl-benzenesulfonamide | B.8 and 3-chlorophenyl acetylene | 474.0 [M + Na]$^+$ |
| 45 | 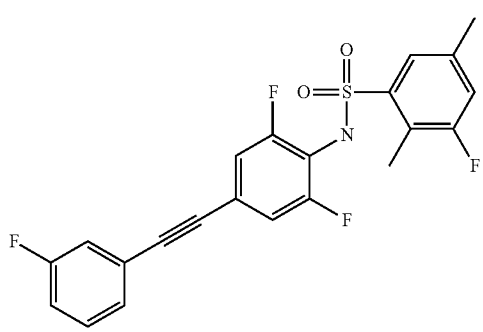 [SMILES: Cc1cc(F)c(C)c(S(=O)(=O)Nc2c(F)cc(C#Cc3cccc(F)c3)cc2F)c1] | N-[2,6-difluoro-4-[2-(3-fluorophenyl)ethynyl]phenyl]-3-fluoro-2,5-dimethyl-benzenesulfonamide | B.10 and 3-fluorophenyl acetylene | 451.0 [M + NH$_4$]$^+$ |

-continued

| Ex. | Structure | Systematic Name | Building Blocks | MS, ESI: m/z |
|---|---|---|---|---|
| 46 | 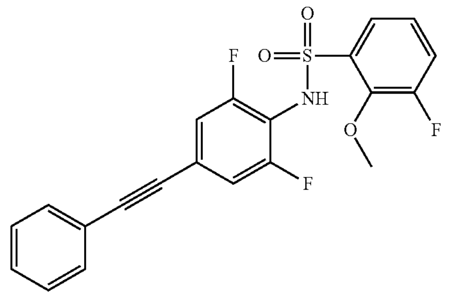 [SMILES: COc1c(F)cccc1S(=O)(=O)Nc1c(F)cc(C#Cc2ccccc2)cc1F] | N-[2,6-difluoro-4-(2-phenylethynyl)phenyl]-3-fluoro-2-methoxy-benzenesulfonamide | B.11 and phenylacetylene | 435.0 [M + NH$_4$]$^+$ |
| 47 | 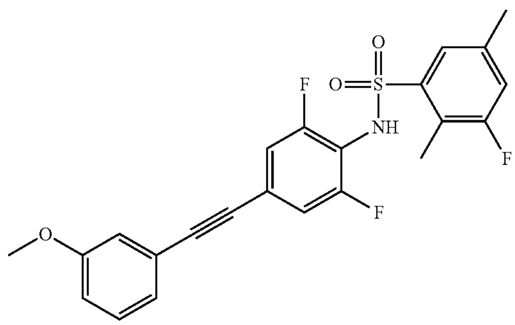 | N-[2,6-difluoro-4-[2-(3-methoxyphenyl)ethynyl]phenyl]-3-fluoro-2,5-dimethyl-benzenesulfonamide | B.10 and 3-ethynylanisole | 463.2 [M + NH$_4$]$^+$ |
| 48 | 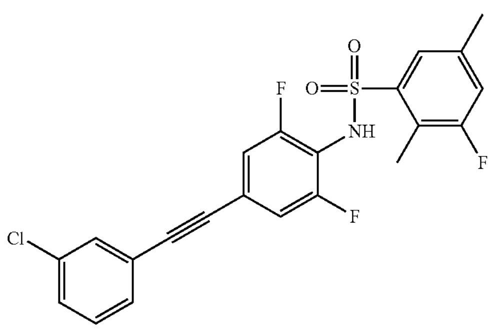 [SMILES: Cc1cc(F)c(C)c(S(=O)(=O)Nc2c(F)cc(C#Cc3cccc(Cl)c3)cc2F)c1] | N-[4-[2-(3-chlorophenyl)ethynyl]-2,6-difluoro-phenyl]-3-fluoro-2,5-dimethyl-benzenesulfonamide | B.10 and 3-chlorophenyl acetylene | 467.1 [M + NH$_4$]$^+$ |
| 49 | 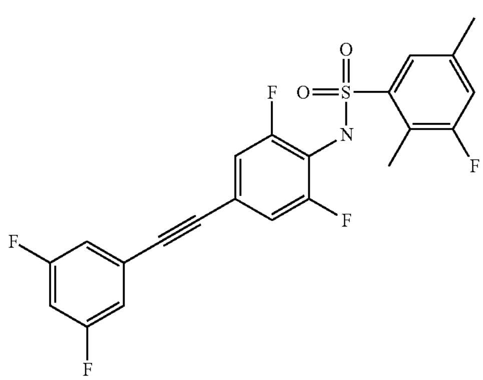 [SMILES: Cc1cc(F)c(C)c(S(=O)(=O)Nc2c(F)cc(C#Cc3cc(F)cc(F)c3)cc2F)c1] | N-[4-[2-(3,5-difluorophenyl)ethynyl]-2,6-difluoro-phenyl]-3-fluoro-2,5-dimethyl-benzenesulfonamide | B.10 and 1-ethynyl-3,5-difluorobenzene | 469.1 [M + NH$_4$]$^+$ |

| Ex. | Structure | Systematic Name | Building Blocks | MS, ESI: m/z |
|---|---|---|---|---|
| 50 | 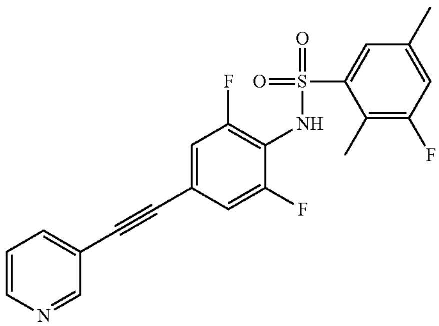 [SMILES: Cc1cc(F)c(C)c(S(=O)(=O)Nc2c(F)cc(C#Cc3cccnc3)cc2F)c1] | N-[2,6-difluoro-4-[2-(3-pyridyl)ethynyl]phenyl]-3-fluoro-2,5-dimethyl-benzenesulfonamide | B.10 and 3-ethynylpyridine | 417.1 [M + H]⁺ |
| 51 | 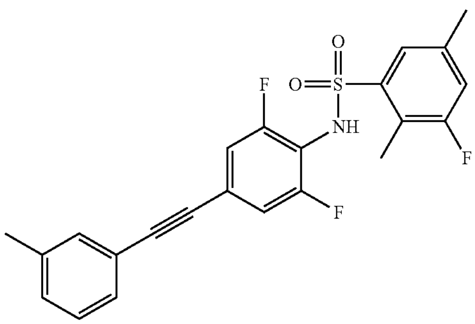 | N-[2,6-difluoro-4-[2-(m-tolyl)ethynyl]phenyl]-3-fluoro-2,5-dimethyl-benzenesulfonamide | B.10 and 3-ethynyltoluene | 447.1 [M + NH₄]⁺ |

Example 52

3-chloro-N-[2,6-difluoro-4-[2-(5-fluoro-3-pyridyl)ethynyl]phenyl]-2-methyl-benzenesulfonamide

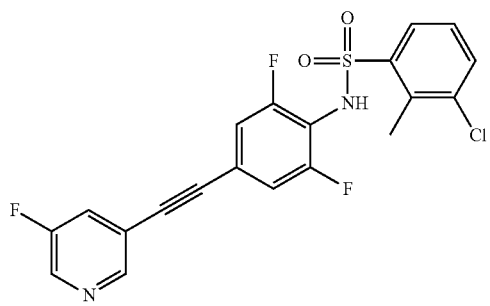 [SMILES: Cc1c(Cl)cccc1S(=O)(=O)Nc1c(F)cc(C#Cc2cncc(F)c2)cc1F]

To a solution of 3-chloro-N-(2,6-difluoro-4-iodo-phenyl)-2-methyl-benzenesulfonamide (B.8) (100 mg, 0.230 mmol, 1 eq) in DMF (3 mL) and water (0.600 mL) was added 2-(5-fluoro-3-pyridyl)ethynyl-trimethyl-silane (1.27 mL, 0.340 mmol), copper(I) iodide (4.29 mg, 0.020 mmol), cesium fluoride (0.02 mL, 0.680 mmol, 3 eq) and [1,1'-Bis(diphenylphosphino) ferrocene]dichloropalladium(II) (8.25 mg, 0.010 mmol) at 25° C. The mixture was heated to 90° C. and stirred for 16 h under N₂. To the reaction mixture was added EtOAc (6 mL), then the solution was washed with brine (10 mL×3). The organic layer was dried over Na₂SO₄, filtered, the filtrate was concentrated in vacuo to afford crude product as a black brown oil. The crude product was purified by Prep-TLC (PE: EtOAc=2:1) to afford desired product as a light yellow solid (20.9 mg, 20.9% yield, 98.6% purity). MS (ESI): m/z=437.0 [M+H]⁺.

Step a) 2-(5-fluoro-3-pyridyl)ethynyl-trimethyl-silane

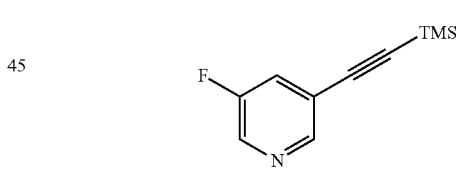

To a solution of 3-fluoro-5-iodopyridine (1.0 g, 4.48 mmol) in THF (10 mL) was added trimethylsilylacetylene (1.27 mL, 8.97 mmol), copper(I) iodide (85.4 mg, 0.450 mmol), triethylamine (1.88 mL, 13.5 mmol) and Bis(triphenylphosphine)palladium(II) dichloride (314.77 mg, 0.450 mmol) at 25° C. The mixture was stirred for 16 h at 25° C. under N₂. To the solution was added H₂O (10 mL), then extracted with EtOAc (15 mL), washed with brine (15 mL×2). The organic layer was dried over Na₂SO₄, filtered, the filtrate was concentrated in vacuo to afford crude product as a yellow oil. The crude product was purified by column chromatography (PE: EtOAc=1:0 to 50:1) to afford the title compound (contaminated with EtOAc) as a yellow oil (1.15 g, 132% yield) which could be carried into the next step without further purification. MS (ESI): m/z=194.2 [M+H]⁺

Example 53

3-chloro-N-[2,6-difluoro-4-[2-(5-fluoro-3-pyridyl)ethynyl]phenyl]-5-fluoro-2-methyl-benzenesulfonamide

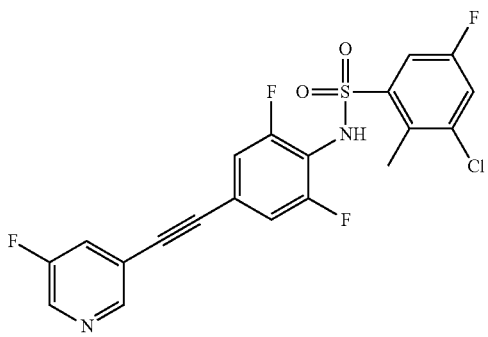 [SMILES: Cc1c(Cl)cc(F)cc1S(=O)(=O)Nc1c(F)cc(C#Cc2cncc(F)c2)cc1F]

To a solution of 3-chloro-N-(2,6-difluoro-4-iodo-phenyl)-5-fluoro-2-methyl-benzenesulfonamide (400 mg, 0.870 mmol) and 2-(5-fluoro-3-pyridyl)ethynyl-trimethyl-silane (334 mg, 1.73 mmol) in N,N-dimethylformamide (15 mL) were added cuprous iodide (8.25 mg, 0.040 mmol), Pd(dppf)Cl$_2$ (63.4 mg, 0.090 mmol) and cesium fluoride (0.1 mL, 2.6 mmol) at 25° C. The mixture was stirred at 80° C. for 15 h. To the mixture was added 20 mL water and extracted with ethyl acetate (20 mL×3). Combined the organic layer to wash with brine (10 mL×3), dry over anhydrous sodium sulfate, filter and concentrate in vacuo. The residue was purified by prep-HPLC and the fraction was freeze-dried under reduced pressure. The title compound, 3-chloro-N-[2,6-difluoro-4-[2-(5-fluoro-3-pyridyl)ethynyl]phenyl]-5-fluoro-2-methyl-benzenesulfonamide (123 mg, 0.270 mmol, 31% yield) was obtained as a yellow solid. MS (ESI+): m/z=455.0 [M+H]$^+$ Step a) 1-benzylsulfanyl-3-chloro-5-fluoro-2-methyl-benzene

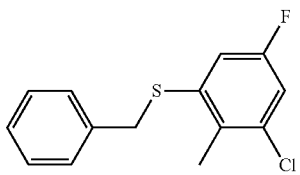 [SMILES: Cc1c(Cl)cc(F)cc1SCc1ccccc1]

To a mixture of 1-bromo-3-chloro-5-fluoro-2-methyl-benzene (1.33 g, 5.95 mmol) and benzyl mercaptan (1.48 g, 11.9 mmol) in N,N-dimethylformamide (30 mL) were added tris(dibenzylideneacetone)dipalladium(0) (272 mg, 0.300 mmol), 4,5-Bis(diphenylphosphino)-9,9-dimethylxanthene (344 mg, 0.600 mmol) and triethylamine (1.24 mL, 8.93 mmol) at 25° C. under N$_2$. Then the mixture was stirred at 100° C. for 15 h. The mixture was diluted with water (50 mL) and extracted with ethyl acetate (100 mL×3). The combined organic phase was washed by brine (50 mL), dried over Na$_2$SO$_4$, filtered and concentrated under reduced pressure to give a residue. The residue was purified by silica gel chromatography (PE:EA=10:1 to 5:1) to give 1-benzylsulfanyl-3-chloro-5-fluoro-2-methyl-benzene (1.4 g, 5.25 mmol, 88% yield) as a white solid. $^1$H NMR (400 MHz, CHLOROFORM-d) δ 7.35 (m, 5H), 6.91-6.97 (m, 2H), 4.12 (s, 2H), 2.36 (s, 3H).

Step b) 3-chloro-5-fluoro-2-methyl-benzenesulfonyl chloride

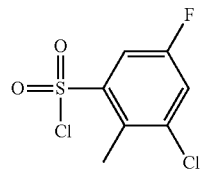

To a mixture of 1-benzylsulfanyl-3-chloro-5-fluoro-2-methyl-benzene (1.0 g, 3.75 mmol) in acetic acid (18 mL) and water (6 mL) was added N-chlorosuccinimide (2.0 g, 15.0 mmol) at 25° C. Then the mixture was stirred at 25° C. for 3 h. The mixture was added 20 mL water and extracted with ethyl acetate (20 mL×3). Combined the organic layer to dry over anhydrous sodium sulfate, filtered and concentrated in vacuo. The crude compound 3-chloro-5-fluoro-2-methyl-benzenesulfonyl chloride (900 mg, 3.7 mmol, 98% yield) was obtained as a colorless oil and directly used without any purification.

Step c) 3-chloro-N-(2,6-difluoro-4-iodo-phenyl)-5-fluoro-2-methyl-benzenesulfonamide

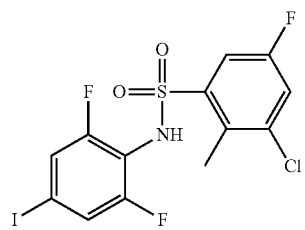 [SMILES: Cc1c(Cl)cc(F)cc1S(=O)(=O)Nc1c(F)cc(I)cc1F]

To a mixture of 2,6-difluoro-4-iodoaniline (1.42 g, 5.55 mmol) in tetrahydrofuran (20 mL) was added lithium bis(trimethylsilyl)amide (5.55 mL, 5.55 mmol) at −70° C. The mixture was stirred at −70° C. for 1 h and then was added 3-chloro-5-fluoro-2-methylbenzenesulfonyl chloride (900 mg, 3.7 mmol). Then the mixture was stirred at 25° C. for 2 h. The mixture was added 20 mL water and extracted with ethyl acetate (30 mL×3). The combined organic layer was dried over anhydrous sodium sulfate, filtered and concentrated in vacuo. The residue was purified by silica gel flash column chromatography, eluting with 20% ethyl acetate in petroleum ether and the fraction was concentrated in vacuo. The compound 3-chloro-N-(2,6-difluoro-4-iodo-phenyl)-5-fluoro-2-methyl-benzenesulfonamide (900 mg, 1.95 mmol, 53% yield) was obtained as a brown solid. MS (ESI+): m/z=483.8 [M+Na]$^+$

Example 54

3-chloro-N-(2,6-difluoro-4-((5-fluoropyridin-3-yl)ethynyl)phenyl)-2,5-dimethylbenzenesulfonamide 2,2,2-trifluoroacetate

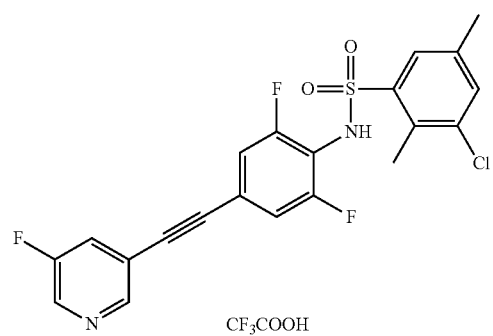 [SMILES: Cc1cc(Cl)c(C)c(S(=O)(=O)Nc2c(F)cc(C#Cc3cncc(F)c3)cc2F)c1 ; "CF3COOH"]

To a solution of 3-chloro-N-(2,6-difluoro-4-iodo-phenyl)-2,5-dimethyl-benzenesulfonamide (20.0 mg, 0.040 mmol) in 1,4-dioxane (1 mL) was added $Na_2CO_3$ (9.26 mg, 0.090 mmol), bis(triphenylphosphine)palladium(II) dichloride (30.7 mg, 0.040 mmol), 2-(5-fluoro-3-pyridyl)ethynyl-trimethyl-silane (8.45 mg, 0.040 mmol) and CuI (8.32 mg, 0.040 mmol). The mixture was heated to 90° C. and stirred for 3 h under $N_2$. 2 mL $H_2O$ was added, then extracted with EtOAc (5 mL×3), and the organics washed with 5 mL brine. The organic layer was dried over $Na_2SO_4$ and filtered. The filtrate was concentrated in vacuo to obtain crude product (69 mg) as a yellow oil, which was purified by prep-HPLC TFA) and freeze-dried to afford 3-chloro-N-[2,6-difluoro-4-[2-(5-fluoro-3-pyridyl)ethynyl]phenyl]-2,5-dimethyl-benzenesulfonamide; 2,2,2-trifluoroacetic acid (8.8 mg, 0.020 mmol, 35.7% yield) as a white solid. MS (ESI): m/z=451.0 [M+H]$^+$ Step a) 3-chloro-2,5-dimethylaniline

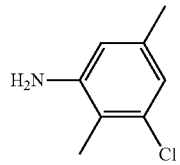

To a solution of 1-chloro-2,5-dimethyl-3-nitro-benzene (400 mg, 2.16 mmol) in EtOAc (10 mL) was added $SnCl_2 \cdot 2H_2O$ (972 mg, 4.31 mmol, 2 eq) and the mixture was stirred at 90° C. for 3 h. The solvent was removed under reduced pressure, the residue was purified by column chromatography on silica gel eluted with (PE:EA=20:1→10:1→5:1) to afford 3-chloro-2,5-dimethyl-aniline (120 mg, 0.770 mmol, 35.8% yield) as a yellow oil MS=156.0, 158.1 [M+H]$^+$ Step b) 3-chloro-2,5-dimethylbenzene-1-sulfonyl chloride

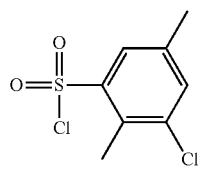

3-chloro-2,5-dimethyl-aniline (80.0 mg, 0.510 mmol, 1 eq) was added to a three-necked flask containing aqueous HCl (0.4 mL, 4 N), placed in an ice bath, temperature control about 0° C., 1 mL of $NaNO_2$ (53.2 mg, 0.770 mmol, 1.5 eq) solution (6.0 mol/L in $H_2O$) was slowly added dropwise, maintaining the temperature below 5° C., stirring for 60 min, obtained diazonium salt solution. Saturated $SO_2$ in acetone solution (2 mL) was added, then add CuCl (101.79 mg, 1.03 mmol, 2 eq), after stirring at room temperature for 60 min, extracted with DCM(10 mL×3). The combined organic phase was washed with 10 mL saturated brine, dried over $MgSO_4$ and concentrated in vacuum, the residue was directly used without any purification as a yellow solid.

Step c) 3-chloro-N-(2,6-difluoro-4-iodophenyl)-2,5-dimethylbenzenesulfonamide

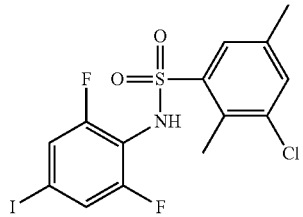 [SMILES: Cc1cc(Cl)c(C)c(S(=O)(=O)Nc2c(F)cc(I)cc2F)c1]

To a solution of 2,6-difluoro-4-iodoaniline (100 mg, 0.390 mmol) in THF (10 mL) was added LiMHDS (0.86 mL, 0.860 mmol, 2.2 eq) at −70° C., the mixture was stirred at −70° C. for 30 min, 3-chloro-2,5-dimethyl-benzenesulfonyl chloride (93.8 mg, 0.390 mmol) was added. The mixture was heated to 20° C. and stirred for 30 min under $N_2$. LCMS showed desired MS, the solvent was removed by reduce pressure, the residue was by prep-TLC (PE: EtOAc=5:1) to afford 3-chloro-N-(2,6-difluoro-4-iodo-phenyl)-2,5-dimethyl-benzenesulfonamide (20 mg, 0.040 mmol, 11.14% yield) as a yellow oil. MS=457.9 [M+H]$^+$.

Example 55

3-chloro-N-(4-((5-chloropyridin-3-yl)ethynyl)-2,6-difluorophenyl)-2-methylbenzenesulfonamide

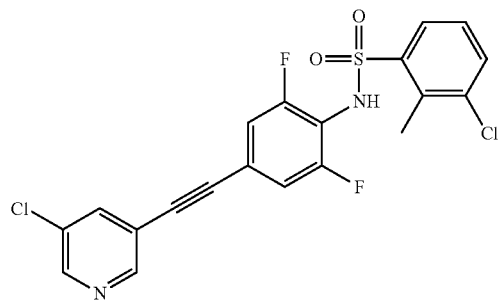 [SMILES: Cc1c(Cl)cccc1S(=O)(=O)Nc1c(F)cc(C#Cc2cncc(Cl)c2)cc1F]

To a solution of copper(I) iodide (39.8 mg, 0.210 mmol) in ACN (10 mL) was added triethylamine (0.87 mL, 6.26 mmol), bis(triphenylphosphine)palladium(II) dichloride (147 mg, 0.210 mmol), 2-(5-chloro-3-pyridyl)ethynyl-trimethyl-silane (100 mg, 0.480 mmol) and copper(I) iodide (39.8 mg, 0.210 mmol), 3-chloro-N-(2,6-difluoro-4-iodo-phenyl)-2-methyl-benzenesulfonamide (Example B.8) (212 mg, 0.480 mmol) at 25° C. The mixture was heated to 60° C. and stirred for 4 h under $N_2$. To the solution was added 5 mL $H_2O$, then the mixture was extracted with 5 mL EtOAc three times, then the combined organics were washed with 15 mL brine. The organic layer was dried over $Na_2SO_4$. After filtration, the filtrate was concentrated in vacuo to obtain crude product (169 mg) as a yellow oil, which was purified by prep-HPLC ($NH_3 \cdot H_2O$) and freeze-dried to afford 3-chloro-N-[4-[2-(5-chloro-3-pyridyl)ethynyl]-2,6-difluoro-phenyl]-2-methyl-benzenesulfonamide; 2,2,2-trifluoroacetic acid (14.2 mg, 0.030 mmol, 6.46% yield) as a white solid. MS (ESI): m/z=452.9 [M+H]$^+$

Step a) 3-chloro-5-((trimethylsilyl)ethynyl)pyridine

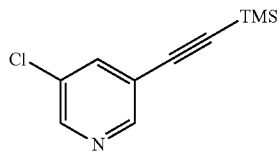 [SMILES: C[Si](C)(C)C#Cc1cncc(Cl)c1]

To a solution of 3-chloro-5-iodo-pyridine (500 mg, 2.09 mmol) in THF (10 mL) was added trimethylsilylacetylene (0.59 mL, 4.18 mmol), copper(I) iodide (39.8 mg, 0.210 mmol), triethylamine (0.87 mL, 6.26 mmol) and bis(triphenylphosphine)palladium(II) dichloride (147 mg, 0.210 mmol) at 25° C. The mixture was heated to 25° C. and stirred for 3 h under $N_2$. To the solution was added 5 mL $H_2O$, the solution was extracted with EtOAc (5 mL×3), and the organics washed with 15 mL brine. The organic layer was dried over $Na_2SO_4$. After filtration, the filtrate was concentrated in vacuo to obtain crude product (169 mg) as a yellow oil. The crude product was purified by Prep-TLC (PE: EA=3:1) to obtain title compound 2-(5-chloro-3-pyridyl)ethynyl-trimethyl-silane (260 mg, 1.24 mmol, 59.4% yield) as a colorless oil. MS (ESI): m/z=293.0, 210.1 $[M+H]^+$.

Example 56

3-chloro-N-[2,6-difluoro-4-[2-(5-methyl-3-pyridyl)ethynyl]phenyl]-2-methyl-benzenesulfonamide; 2,2,2-trifluoroacetic acid

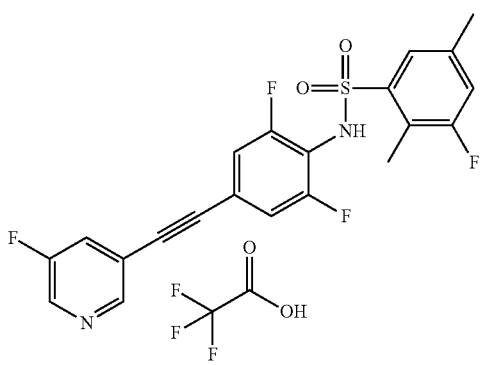

To a solution of 3-chloro-N-[2,6-difluoro-4-(2-trimethylsilylethynyl)phenyl]-2-methyl-benzenesulfonamide (67.0 mg, 0.160 mmol) in DMF (1 mL) and water (0.200 mL) was added 3-bromo-5-methylpyridine (27.8 mg, 0.160 mmol, 1 eq), copper(I) iodide (3.08 mg, 0.020 mmol), Cesium fluoride (73.8 mg, 0.490 mmol) and [1,1'-Bis(diphenylphosphino)ferrocene]dichloropalladium(II) (5.92 mg, 0.010 mmol) at 25° C. The mixture was heated to 90° C. and stirred for 16 h under $N_2$. To the solution was added EtOAc (3 mL), and the resultant solution was washed with brine (3 mL×3). The organic layer was dried over $Na_2SO_4$, filtered, and the filtrate was concentrated in vacuo to afford crude product as a black brown oil. All batches of the crude product were purified by Prep-TLC (PE: EtOAc=1:1) and then purified by Prep-HPLC (TFA) to afford desired product as a white solid (6.3 mg, 7.1% yield, 99.7% purity). MS (ESI): m/z=433.0 $[M+H]^+$.

Step a) 3-chloro-N-[2,6-difluoro-4-(2-trimethylsilylethynyl)phenyl]-2-methyl-benzenesulfonamide

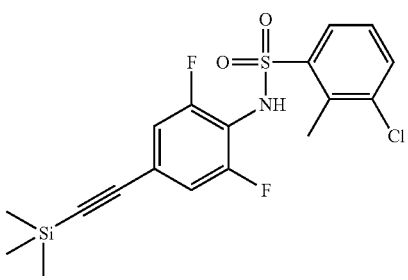 [SMILES: Cc1c(Cl)cccc1S(=O)(=O)Nc1c(F)cc(C#C[Si](C)(C)C)cc1F]

To a solution of 3-chloro-N-(2,6-difluoro-4-iodo-phenyl)-2-methyl-benzenesulfonamide (B.8) (300 mg, 0.680 mmol) in THF (4 mL) was added trimethylsilylacetylene (0.19 mL, 1.35 mmol), copper(I) iodide (12.9 mg, 0.070 mmol), triethylamine (0.28 mL, 2.03 mmol) and bis(triphenylphosphine)palladium(II) dichloride (47.5 mg, 0.070 mmol) at 25° C. The mixture was stirred for 16 h at 25° C. under $N_2$. To the solution was added $H_2O$ (5 mL), and the resultant solution was then extracted with EtOAc (5 mL×2), and the combined organics were washed with brine (15 mL). The organic layer was dried over $Na_2SO_4$, filtered, the filtrate was concentrated in vacuo to afford crude product as a yellow oil. The crude product was purified by Prep-TLC (PE: EtOAc=5:1) to afford desired product as a yellow oil (117 mg, 39.8% yield). MS (ESI): m/z=414.1 $[M+H]^+$.

Example 57

N-[2,6-difluoro-4-[2-(5-fluoro-3-pyridyl)ethynyl]phenyl]-3-fluoro-2-methyl-benzenesulfonamide; 2,2,2-trifluoroacetic acid

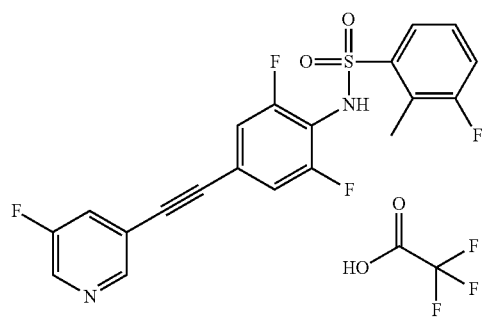

To a solution of N-(2,6-difluoro-4-iodo-phenyl)-3-fluoro-2-methyl-benzenesulfonamide (100 mg, 0.230 mmol) in DMF (4 mL) and water (0.800 mL) was added 2-(5-fluoro-3-pyridyl)ethynyl-trimethyl-silane (45.25 mg, 0.230 mmol), copper(I) iodide (4.46 mg, 0.020 mmol), cesium fluoride (107 mg, 0.700 mmol) and [1,1'-Bis(diphenylphosphino)ferrocene]dichloropalladium(II) (8.56 mg, 0.010 mmol) at 25° C. The mixture was heated to 90° C. and stirred for 16 hs under $N_2$. To the solution was added EtOAc (10 mL), then washed with brine (10 mL×3). The organic layer was dried over $Na_2SO_4$, filtered, and the filtrate was concentrated in vacuo to afford crude product as a black brown oil. The crude product was purified by Prep-TLC (PE: EtOAc=2:1) and then purified by Prep-HPLC (TFA) to afford desired product as a white solid (26.4 mg, 26.7% yield, 99.7% purity). MS (ESI): m/z=421.0 [M+H]+

Step a) N-(2,6-difluoro-4-iodo-phenyl)-3-fluoro-2-methyl-benzenesulfonamide

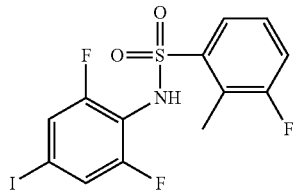 [SMILES: Cc1c(F)cccc1S(=O)(=O)Nc1c(F)cc(I)cc1F]

A mixture of 2,6-difluoro-4-iodoaniline (300.0 mg, 1.18 mmol) in tetrahydrofuran (3 mL) was cooled to −70° C., LiHMDS (1 M in THF) (1.76 mL, 1.76 mmol) was added dropwise maintaining the temperature not higher than −60° C., then stirred for 1 h. A solution of 3-fluoro-2-methyl-benzenesulfonyl chloride (CAS: 875166-92-0) (589.1 mg, 2.82 mmol, 2.4 eq) in tetrahydrofuran (0.500 mL) was added dropwise maintaining the inner temperature not higher than −60° C., then it was stirred at −70° C. for another 4 h. To the solution was added NH4Cl solution (5 mL), then extracted with EtOAc (5 mL×3). The organics were washed with brine (10 mL). The organic layer was dried over Na2SO4, filtered, and the filtrate was concentrated in vacuo to afford crude product as a black brown oil. The crude product was purified by Prep-TLC (PE: EtOAc=4:1) to afford desired product as a light yellow oil (233.0 mg, 44.4% yield). MS (ESI): m/z=449.9 [M+Na]+.

Example 58

N-[4-(4-tert-butylpyrazol-1-yl)-2,6-difluoro-phenyl]-2-chloro-benzenesulfonamide

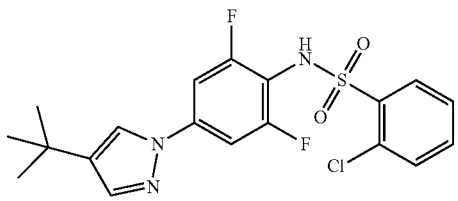 [SMILES: CC(C)(C)c1cnn(-c2cc(F)c(NS(=O)(=O)c3ccccc3Cl)c(F)c2)c1]

To a solution of 2-chloro-N-(2,6-difluoro-4-hydrazino-phenyl)benzenesulfonamide (50 mg, 0.150 mmol) and 2-tert-butylpropanedial (19.2 mg, 0.150 mmol) in 1-butanol (0.5 mL) was stirred at 120° C. for 12 h. The reaction was purified by prep-HPLC and lyophilized to give N-[4-(4-tert-butylpyrazol-1-yl)-2,6-difluoro-phenyl]-2-chloro-benzenesulfonamide (2 mg, 3% yield) as a white solid. MS (ESI+): m/z=425.9 [M+H]+.

Step a) 2-chloro-N-(2,6-difluoro-4-nitro-phenyl)benzenesulfonamide

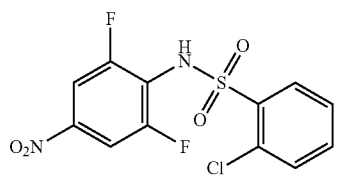

A mixture of 2,6-difluoro-4-nitro-aniline (1.0 g, 5.74 mmol) in THF (10 mL) at −75° C. was added 1 M LiHMDS in THF (6.32 mL, 6.32 mmol). The reaction mixture was stirred at 25° C. for 30 min and then 2-chlorobenzenesulfonyl chloride (1.33 g, 6.32 mmol) was added, the mixture was continually stirred at 25° C. for 11.5 h. The reaction was quenched by 20 mL saturated ammonia chloride solution and then extracted with ethyl acetate (50 mL×3). The combined organic phase was washed by brine (20 mL×2), dried with anhydrous anhydrous sodium sulfate, filtered and concentrated in vacuo. The residue was purified by silica gel chromatography (PE:EA=100:1 to 5:1) to afford 2-chloro-N-(2,6-difluoro-4-nitro-phenyl)benzenesulfonamide (1.1 g, 3.15 mmol, 55% yield) as yellow solid.

Step b) N-(4-amino-2,6-difluoro-phenyl)-2-chloro-benzenesulfonamide

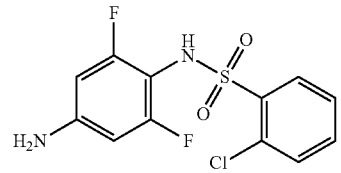 [SMILES: O=[N+]([O-])c1cc(F)c(NS(=O)(=O)c2ccccc2Cl)c(F)c1]

To a solution of 2-chloro-N-(2,6-difluoro-4-nitro-phenyl) benzenesulfonamide (1.1 g, 3.15 mmol), ammonium chloride (337 mg, 6.31 mmol) in ethanol (10 mL) and water (2 mL) was added iron powder (352 mg, 6.31 mmol). The reaction was stirred at 80° C. for 2 h. The reaction mixture was filtered and the filtrate was concentrated to give N-(4-amino-2,6-difluoro-phenyl)-2-chloro-benzenesulfonamide (1 g, 3.14 mmol, 99% yield) as a light brown solid.

Step c) 2-chloro-N-(2,6-difluoro-4-hydrazino-phenyl) benzenesulfonamide

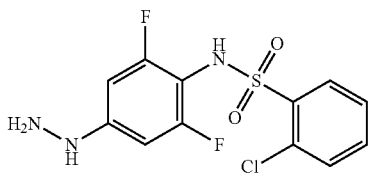 [SMILES: NNc1cc(F)c(NS(=O)(=O)c2ccccc2Cl)c(F)c1]

A stirred mixture of N-(4-amino-2,6-difluoro-phenyl)-2-chloro-benzenesulfonamide (500 mg, 1.57 mmol), 37% HCl aqueous solution (2 mL) and water (1 mL) was heated to form a complete solution (about 70° C.) under nitrogen atmosphere. Then the solution was cooled to −5° C., and was added a solution of sodium nitrite (130 mg, 1.88 mmol, 1.2 eq) in water (1 mL). The reaction mixture was stirred at −5° C. for 1 h. Then the mixture was cooled to −20° C., and was added a solution of tin(II) dichloride dihydrate (1.06 g, 4.71 mmol) in 37% HCl aqueous solution (2 mL). The reaction mixture was stirred at 20° C. for 2 h. The reaction mixture was basified to pH=9 with 1 mol/L NaOH aqueous solution, diluted with ethyl acetate (20 mL×3) and washed with brine (10 mL×2). The combined organic layers were dried over anhydrous sodium sulfate, and concentrated to give the crude product. The crude product was purified by prep-HPLC to give 2-chloro-N-(2,6-difluoro-4-hydrazino-phenyl)benzenesulfonamide (60 mg, 0.180 mmol, 11% yield) as yellow solid. MS (ESI+): m/z=355.9 [M+Na]+

Step d) 2-tert-butylpropanedial

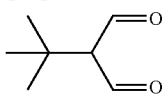

To a solution of 2-tert-butylpropanedinitrile (200 mg, 1.64 mmol) in toluene (1 mL) was added DIBAL-H (3.27 mL, 4.91 mmol) at −60° C. The reaction was stirred at 25° C. for 4 h. The reaction mixture was acidified to pH=2 with 1 mol/L HCl aqueous solution, diluted with ethyl acetate (50 mL×3), washed with brine (20 mL×2). The combined organic layers were dried over anhydrous sodium sulfate, and then concentrated to give 2-tert-butylpropanedial (60 mg, 0.470 mmol, 28% yield) as light yellow liquid.

Examples 59 to 60 of the following table were prepared in analogy to Example 58, using the following sulfonyl chloride building blocks in place of 2-chlorobenzenesulfonyl chloride in Step a).

To a solution of N-[2,6-difluoro-4-[2-(3-methoxyphenyl)ethynyl]phenyl]-3-fluoro-2,5-dimethyl-benzenesulfonamide (Example 47) (426 mg, 0.960 mmol) in DCM (4.5 mL) was added BBr$_3$ (0.27 mL, 2.87 mmol) at 0° C. The solution was stirred for 4 h at 15° C. To the solution was added saturated NaHCO$_3$ solution (4 mL) at 0° C., then extracted with EtOAc (4 mL×3), and the organics washed with brine (10 mL). The organic layer was dried over Na$_2$SO$_4$, filtered, and the filtrate was concentrated in vacuo to afford crude product as a brown oil. The crude product was purified by Prep-HPLC (TFA) to afford desired product as a light brown solid (99.7 mg, 23.8% yield, 98.7% purity). MS (ESI): m/z=449.0 [M+NH$_4$]$^+$

| Ex. | Structure | Systematic Name | Building Blocks | MS, ESI: m/z |
|---|---|---|---|---|
| 59 | 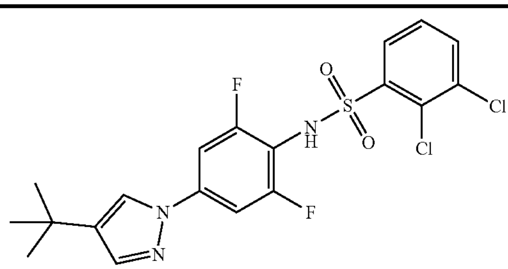 | N-[4-(4-tert-butylpyrazol-1-yl)-2,6-difluoro-phenyl]-2,3-dichloro-benzenesulfonamide | 2,3-dichlorobenzenesulfonyl chloride, CAS 82417-45-6 | 459.9 [M + Na]$^+$ |
| 60 | 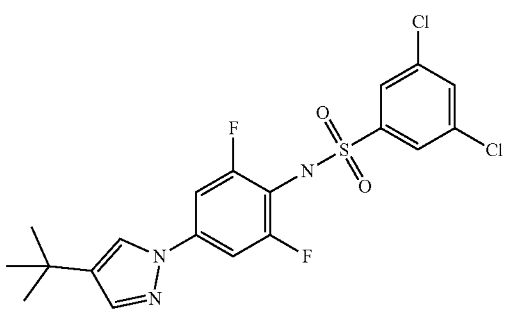 [SMILES: CC(C)(C)c1cnn(-c2cc(F)c(NS(=O)(=O)c3cc(Cl)cc(Cl)c3)c(F)c2)c1] | N-[4-(4-tert-butylpyrazol-1-yl)-2,6-difluoro-phenyl]-3,5-dichloro-benzenesulfonamide | 3,5-dichlorobenzenesulfonyl chloride, CAS 705-21-5 | 460.1 [M + H]$^+$ |

Example 61

N-[2,6-difluoro-4-[2-(3-hydroxyphenyl)ethynyl]phenyl]-3-fluoro-2,5-dimethyl-benzenesulfonamide

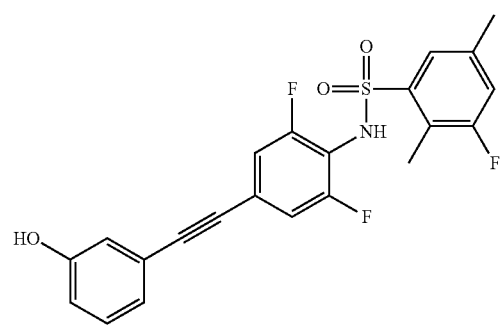 [SMILES: Cc1cc(F)c(C)c(S(=O)(=O)Nc2c(F)cc(C#Cc3cccc(O)c3)cc2F)c1]

Synthesis of Building Blocks

Example A.1

2,6-difluoro-4-(phenylethynyl)aniline

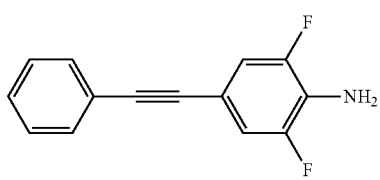

To a solution of 2,6-difluoro-4-iodo-phenylamine (3.0 g, 11.8 mmol) in THF (30 mL) were added phenyl acetylene (2.6 mL, 23.5 mmol) and Et$_3$N (3.4 mL, 23.5 mmol) and nitrogen was purged for 20 min. Then Pd(PPh$_3$)$_2$Cl$_2$ (495.0 mg, 0.7 mmol) and CuI (67 mg, 0.4 mmol) were added and the solution again degassed for another 10 min. Reaction mixture was stirred at 70° C. for 16 h. The reaction mixture was cooled to 25° C. and concentrated. Resulting crude product was purified by column chromatography over silica gel (30-40% EtOAc/hexane) to obtain 2,6-difluoro-4-phenylethynyl-phenyl amine (2.2 g, 82%) as light yellow solid. MS (ESI): m/z=230.1 [M+H]$^+$ Example A.2

2,6-difluoro-4-[2-(3-pyridyl)ethynyl]aniline

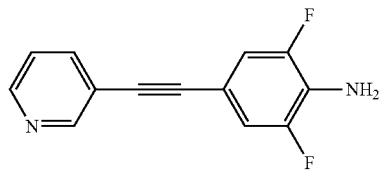 [SMILES: Nc1c(F)cc(C#Cc2ccccc2)cc1F]

To a solution of 2,6-difluoro-4-iodoaniline (10.0 g, 39.22 mmol) in THF (150 mL) were added 3-ethynylpyridine (12.1 g, 117 mmol) and $Et_3N$ (10.9 mL, 78.4 mmol) and nitrogen was purged for 10 min. Then $Pd(PPh_3)_2Cl_2$ (1.67 g, 2.35 mmol) and CuI (0.22 g, 1.18 mmol) were added and again degassed for another 10 min. The reaction mixture stirred at 70° C. for 6 h. Solvent was evaporated and the resulting crude was purified by column chromatography over silica gel to get 2,6-difluoro-4-[2-(3-pyridyl)ethynyl]aniline (9.2 g, 40.0 mmol, 96.8% yield) as yellow solid. MS (ESI): m/z=230.8 [M+H]$^+$ Example A.3

2,6-difluoro-4-(5-fluoro-pyridin-3-ylethynyl)-phenylamine

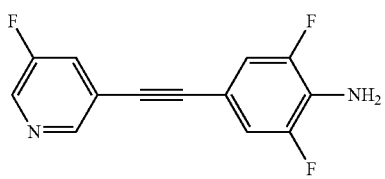 [SMILES: Nc1c(F)cc(C#Cc2cncc(F)c2)cc1F]

To a solution of 2,6-Difluoro-4-iodo-phenylamine (1.5 g, 5.9 mmol) in THF (30 mL) was added 3-ethynyl-5-fluoropyridine (2.2 g, 17.7 mmol) and $Et_3N$ (1.6 ml, 11.7 mmol) and nitrogen was purged for 10 min. Then $Pd(PPh_3)_2Cl_2$ (250.0 mg, 0.35 mmol) and CuI (34.0 mg, 0.17 mmol) were added and again degassed for another 10 min. Reaction mixture was stirred at 70° C. for 5 h. TLC monitoring confirmed complete consumption of starting. Then solvent was evaporated and resulting crude was purified by column chromatography eluting with 20% EtOAc-hexane to obtain 2,6-difluoro-4-(5-fluoro-pyridin-3-ylethynyl)-phenylamine (1.1 g, 75%) as a yellow solid.

Example B.1

2-chloro-3-methoxybenzenesulfonyl chloride

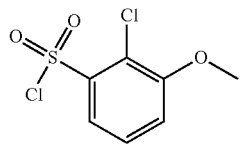

A solution of $SO_2$/CuCl/AcOH was prepared by bubbling $SO_2$ gas into the AcOH (11.0 mL) solution at 0° C. for 10 min and then CuCl (190.0 mg, 1.9 mmol) was added followed by again bubbling of $SO_2$ gas for 5 min at the same temp. In a separate flask an aqueous solution of $NaNO_2$ (660 mg, 9.5 mmol) in $H_2O$ (9.5 mL) was added to a pre-cooled (0° C.) solution of 2-Chloro-3-methoxyphenylamine (CAS: 113206-03-4) (1.0 g, 6.3 mmol) in conc. HCl (9.5 mL). After stirring for 1 h the reaction mixture was added to the $SO_2$/CuCl/AcOH solution at 0° C. and allowed to warm to 25° C. At this temperature reaction was continued for 2 h. After that water was added and the white precipitate was filtered out. The white solid was lyophilized to get the desired product 2-Chloro-3-methoxy-benzenesulfonyl chloride (1.3 g, crude) as off-white solid and directly used for next step without further purification.

Example B.2

2-methyl-3-(trifluoromethyl)benzenesulfonyl chloride

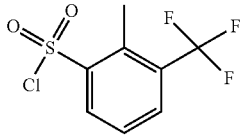

A solution of $SO_2$/CuCl/AcOH was prepared by bubbling $SO_2$ gas into the AcOH (11.0 mL) solution at 0° C. for 10 min and then CuCl (190.0 mg, 1.9 mmol) was added followed by again bubbling of $SO_2$ gas for 5 min at the same temp. In a separate flask an aqueous solution of $NaNO_2$ (660 mg, 9.5 mmol) in $H_2O$ (9.5 mL) was added to a pre-cooled (0° C.) solution of 2-Chloro-3-methoxyphenylamine (CAS: 113206-03-4) (1.0 g, 6.3 mmol) in conc. HCl (9.5 mL). After stirring for 1 h the reaction mixture was added to the $SO_2$/CuCl/AcOH solution at 0° C. and allowed to warm to 25° C. At this temperature reaction was continued for 2 h. After that water was added and the white precipitate was filtered out. The white solid was lyophilized to get the desired product 2-Chloro-3-methoxy-benzenesulfonyl chloride (1.3 g, crude) as off-white solid and directly used for next step without further purification.

Example B.3

2-methylpyridine-3-sulfonyl chloride

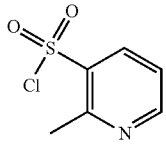

To a solution of 3-bromo-2-methylpyridine (500 mg, 2.91 mmol) in THE (10 mL) was added n-butyllithium (1.74 mL, 4.36 mmol) at −70° C. Then the mixture was stirred at −70° C. for 1 h and DABCO-bis(sulfur dioxide) (1.05 g, 4.36 mmol) was added. The mixture was stirred at −70° C. for 1 h again. Then to the mixture was added sulfuryl chloride (1.96 g, 14.53 mmol, 5 eq) and the reaction mixture was allowed to slowly warm to 25° C. and stirred for 2 h. To the mixture was added 20 mL water and extracted with ethyl acetate (20 mL×3). The combined organic layer was dried over anhydrous sodium sulfate, filtered and concentrated in vacuo. The crude compound 2-methylpyridine-3-sulfonyl chloride (500 mg, 2.61 mmol, 90% yield) was obtained as a brown oil.

Example B.4

4-methylpyridine-3-sulfonyl chloride

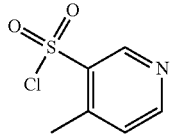

Step a) 3-benzylsulfanyl-4-methyl-pyridine

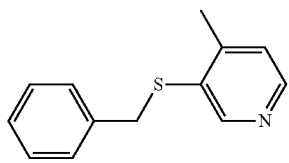

To a mixture of benzyl mercaptan (3.25 g, 26.16 mmol, 1.5 eq) and 3-bromo-4-methylpyridine (3.0 g, 17.4 mmol, 1 eq) in N,N-dimethylformamide (30 mL) were added Tris(dibenzylideneacetone)dipalladium(0) (800 mg, 0.870 mmol), 4,5-Bis(diphenylphosphino)-9,9-dimethylxanthene (1.01 g, 1.74 mmol) and triethylamine (3.65 mL, 26.16 mmol) at 25° C. Then the mixture was stirred at 100° C. for 15 h. Then mixture was added 20 mL water and extracted with ethyl acetate (30 mL×3). Combined the organic layer to wash by brine (15 mL×3), dried over anhydrous sodium sulfate, filtered and concentrated in vacuo. The residue was purified by silica gel chromatography (PE/EA=20/1 to 5/1). The compound 3-benzylsulfanyl-4-methyl-pyridine (400 mg, 1.86 mmol, 11% yield) was obtained as a brown oil. MS (ESI+): m/z=216.1 [M+H]+

Step b) 4-methylpyridine-3-sulfonyl chloride

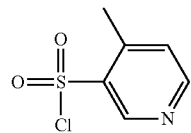

To a mixture of 3-benzylsulfanyl-4-methyl-pyridine (400 mg, 1.86 mmol) in acetic acid (6 mL) and water (6 mL) was added N-chlorosuccinimide (992 mg, 7.43 mmol) and at 25° C. Then the mixture was stirred at 25° C. for 3 h. The mixture was added 20 mL water and extracted with ethyl acetate (20 mL×3). Combined the organic layer to dry over anhydrous sodium sulfate, filtered and concentrated in vacuo. The crude compound 4-methylpyridine-3-sulfonyl chloride (300 mg, 1.57 mmol, 84% yield) was obtained as a colorless oil and directly used without any purification.

Example B.5

3-chloro-2-(methoxymethyl)benzenesulfonyl chloride

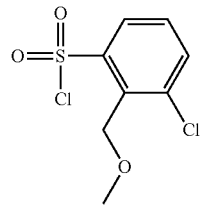

Step a) (2-bromo-6-chloro-phenyl)methanol

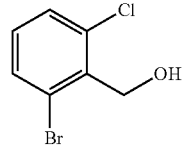

To a mixture of 2-bromo-6-chlorobenzaldehyde (3.0 g, 13.67 mmol) in methanol (50 mL) was slowly added sodium borohydride (776 mg, 20.5 mmol) at 0° C. Then the mixture was stirred at 25° C. for 1 h. The mixture was quenched by 50 mL water and extracted with ethyl acetate (50 mL×3). Combined the organic layer to dry over anhydrous sodium sulfate, filtered and concentrated in vacuo. The crude compound (2-bromo-6-chloro-phenyl)methanol (2.5 g, 11.29 mmol, 82% yield) as a white solid was used into next reaction without further purification.

Step b) 1-bromo-3-chloro-2-(methoxymethyl)benzene

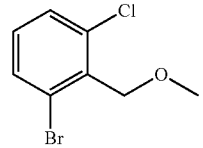

To a mixture of (2-bromo-6-chloro-phenyl)methanol (2.5 g, 11.3 mmol) in tetrahydrofuran (50 mL) was added sodium hydride (677 mg, 16.9 mmol) at 0° C. and stirred for 1 h. Then the mixture was added iodomethane (1.05 mL, 16.9 mmol) at 0° C. Finally the mixture was stirred at 25° C. for 2 h. The mixture was quenched by 30 mL water and extracted with ethyl acetate (30 mL×3). Combined the organic layer to dry over anhydrous sodium sulfate, filtered and concentrated in vacuo. The residue was purified by silica gel flash column chromatography eluting with 100% petroleum ether. The compound 1-bromo-3-chloro-2-(methoxymethyl)benzene (2.5 g, 10.6 mmol, 94% yield) was obtained as a colorless oil. ¹H NMR (400 MHz, CHLOROFORM-d) δ 7.53 (d, J=8.0 Hz, 1H), 7.39 (d, J=8.0 Hz, 1H), 7.14 (t, J=8.0 Hz, 1H), 4.77 (s, 2H), 3.47 (s, 3H)

Step c) 3-chloro-2-(methoxymethyl)benzenesulfonyl chloride

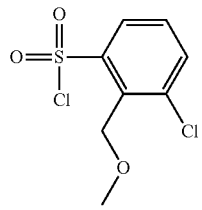

To a solution of 1-bromo-3-chloro-2-(methoxymethyl)benzene (300 mg, 1.27 mmol) in THF (15 mL) was added isopropylmagnesium chloride (1.47 mL, 1.91 mmol, 1.5 eq) at −40° C. Then the mixture was stirred at −40° C. for 1 h and DABCO-bis(sulfur dioxide) (459 mg, 1.91 mmol) was added. The mixture was stirred at −40° C. for 1 h again. Then the mixture was added N-chlorosuccinamide (258 mg, 1.91 mmol) and allowed to slowly warm to 25° C. and stirred for 2 h. The mixture was quenched by 20 mL and extracted with ethyl acetate (30 mL×3). Combined the organic layer to dry over anhydrous sodium sulfate, filtered and concentrated in vacuo. The crude compound 3-chloro-2-(methoxymethyl)benzenesulfonyl chloride (200 mg, 0.780 mmol, 61% yield) was obtained as a colorless oil.

Example B.6

2-chloro-3-(trifluoromethyl)benzenesulfonyl chloride

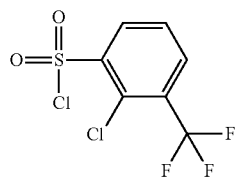 [SMILES: O=S(=O)(Cl)c1cccc(C(F)(F)F)c1Cl]

To a solution of 1-bromo-2-chloro-3-(trifluoromethyl)benzene (500 mg, 1.93 mmol) in THF (50 mL) was added isopropylmagnesium chloride (2.89 mL, 2.89 mmol) at −70° C. Then the mixture was stirred at −70° C. for 1 h and DABCO-bis(sulfur dioxide) (695 mg, 2.89 mmol) was added. The mixture was stirred at −70° C. for 1 h again. Then to the mixture was added N-chlorosuccinimide (386 mg, 2.89 mmol) and allowed to slowly warm to 25° C. and stirred for 2 h. The mixture was quenched by 20 mL and extracted with ethyl acetate (30 mL×3). Combined the organic layer to dry over anhydrous sodium sulfate, filtered and concentrated in vacuo. The crude compound 2-chloro-3-(trifluoromethyl)benzenesulfonyl chloride (500 mg, 1.79 mmol, 93% yield) was obtained as a yellow solid without any further purification.

Example B.7 benzo[d]oxazole-7-sulfonyl chloride

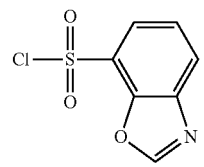 [SMILES: O=S(=O)(Cl)c1cccc2ncoc12]

Step a) 7-benzylsulfanyl-1,3-benzoxazole

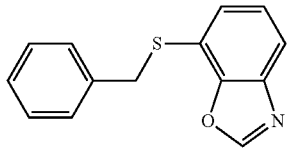

To a mixture of benzyl mercaptan (1.88 g, 15.2 mmol) and 7-bromo-1,3-benzoxazole (2.0 g, 10.1 mmol) in N,N-dimethylformamide (15 mL) were added Tris(dibenzylideneacetone) dipalladium(0) (462 mg, 0.500 mmol), 4,5-Bis(diphenylphosphino)-9,9-dimethylxanthene (584 mg, 1.01 mmol) and triethylamine (2.11 mL, 15.2 mmol) at 25° C. Then the mixture was stirred at 100° C. for 15 h. The mixture was added 20 mL water and extracted with ethyl acetate (30 mL×3). Combined the organic layers to wash by brine (10 mL×3, dry over anhydrous sodium sulfate, filter and concentrate in vacuo. The residue was purified by silica gel chromatography column (PE/EA=50/1 to 10/1). The compound 7-benzylsulfanyl-1,3-benzoxazole (2 g, 8.29 mmol, 82% yield) was obtained as a red oil.

Step b) benzo[d]oxazole-7-sulfonyl chloride

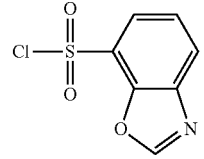 [SMILES: O=S(=O)(Cl)c1cccc2ncoc12]

To a mixture of 7-benzylsulfanyl-1,3-benzoxazole (1.0 g, 4.14 mmol) and acetic acid (4 mL) in DCM (20 mL) were added sulfuryl dichloride (4.0 g, 29.7 mmol, 7.15 eq) and water (0.8 mL) at 25° C. Then the mixture was stirred at 25° C. for 4 h. The mixture was added 20 mL water and extracted with DCM (20 mL×3). Combined the organic layer to dry over anhydrous sodium sulfate, filtered and concentrated in vacuo. The crude compound 1,3-benzoxazole-7-sulfonyl chloride (500 mg, 2.3 mmol, 55% yield) was used without any purification.

Example B.8

3-chloro-N-(2,6-difluoro-4-iodo-phenyl)-2-methyl-benzenesulfonamide

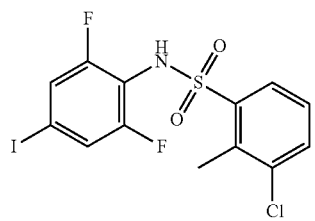 [SMILES: Cc1c(Cl)cccc1S(=O)(=O)Nc1c(F)cc(I)cc1F]

A mixture of 2,6-difluoro-4-iodoaniline (10.0 g, 39.2 mmol) in THF (150 mL) was cooled to −70° C., then LiHMDS (47.1 mL, 1 M in THF, 47.1 mmol) was added dropwise keeping the temperature not higher than −60° C., then stirred for 1 h, a solution of 3-chloro-2-methylbenzenesulfonyl chloride (10.6 g, 47.1 mmol, 1.2 eq) in THF(50 mL) was added. Finally the mixture was stirred at −65° C. for another 4 h. The reaction was quenched by saturated NH$_4$Cl aqueous solution (100 mL) and extracted with EtOAc (200 mL×2). The combined organic layer was dried over anhydrous sodium sulfate, filtered and concentrated in vacuo. The crude was purified by column chromatography (PE/EA=100/0 to 5/1) to afford 3-chloro-N-(2,6-difluoro-4-iodo-phenyl)-2-methyl-benzenesulfonamide (9.6 g, 21.6 mmol, 55% yield) as gray solid. 1H NMR (400 MHz, CHLOROFORM-d) δ 7.88 (d, J=8 Hz, 1H), 7.65 (d, J=8 Hz, 1H), 7.24-7.30 (m, 3H), 6.37 (br, 1H), 2.79 (s, 3H).

Example B.9

3-fluoro-2,5-dimethyl-benzenesulfonyl chloride

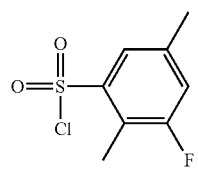

Step a) 1-bromo-3-fluoro-2,5-dimethyl-benzene

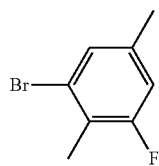

To a solution of 3-bromo-5-fluorotoluene (5.0 g, 26.5 mmol) in THF (50 mL) was added LDA (14.6 mL, 29.1 mmol) dropwise at −70° C. The mixture was stirred for 1 hour at −70° C. To the mixture was added iodomethane (3.75 g, 26.45 mmol) in THF (5 mL) at −70° C. The mixture was stirred for 6 hours at 25° C. The solution was quenched by saturated aqueous NH$_4$Cl solution (30 mL), then extracted with EtOAc (30 mL×2), and the organics washed with brine (50 mL). The organic layer was dried over Na$_2$SO$_4$, filtered, the filtrate was concentrated in vacuo to afford crude product as a yellow oil. The crude product was purified by column chromatography (PE: EtOAc=1:0) to afford the title compound as a colorless oil (5.34 g, 99.4% yield) which was carried into the next step without further purification.

Step b) 3-fluoro-2,5-dimethyl-benzenesulfonyl chloride

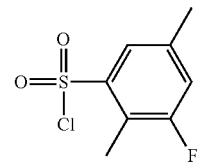

To a solution of 1-bromo-3-fluoro-2,5-dimethyl-benzene (500 mg, 2.46 mmol) in tetrahydrofuran (20 mL) was added n-Butyllithium solution (1.48 mL, 3.69 mmol) at −70° C. The mixture was stirred at −70° C. for 0.5 h. Sulfur dioxide (158 mg, 2.46 mmol) was passed through the resulting solution for 10 minutes (inner temperature maintained below 10° C.), and allowed to slowly warm to 25° C. and stirred for 0.5 h. To the mixture was added N-chlorosuccinimide (394 mg, 2.95 mmol) in DCM (5 mL) at 10° C., then the solution was stirred for 0.5 h at 25° C. The mixture was quenched by water (1 mL) and dried over Na$_2$SO$_4$. The mixture was filtered and washed with EtOAc (6 mL×2). The organic layer was concentrated in vacuo to afford crude product as a light yellow oil (564 mg, 102.9% yield). The crude product was used in next step directly.

Example B.10

N-(2,6-difluoro-4-iodo-phenyl)-3-fluoro-2,5-dimethyl-benzenesulfonamide

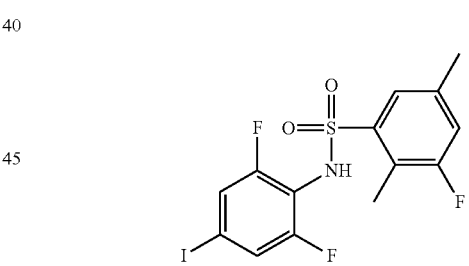

A mixture of 2,6-difluoro-4-iodoaniline (300 mg, 1.18 mmol) in tetrahydrofuran (3 mL) was cooled to −70° C., LiHMDS (1.41 mL, 1.41 mmol) was added dropwise maintaining the temperature not higher than −60° C., then stirred for 0.5 h. A solution of 3-fluoro-2,5-dimethyl-benzenesulfonyl chloride (B.9) (563 mg, 2.53 mmol, 2.15 eq) in tetrahydrofuran (1 mL) was added dropwise maintaining the inner temperature not higher than −60° C., then the reaction mixture was stirred at −70° C. for another 4 hrs. To the solution was added saturated aqueous NH$_4$Cl solution (3 mL), and the resultant solution was extracted with EtOAc (3 mL×3). The organic layer was dried over Na$_2$SO$_4$, filtered, and the filtrate was concentrated in vacuo to obtain crude product as a yellow oil. The crude product was purified by Prep-TLC (PE: EtOAc=4:1) to afford desired product as a yellow solid (100 mg, 17.2% yield). MS (ESI): m/z=459.0 [M+NH$_4$]$^+$.

Example B.11

N-(2,6-difluoro-4-iodo-phenyl)-3-fluoro-2-methoxy-benzenesulfonamide

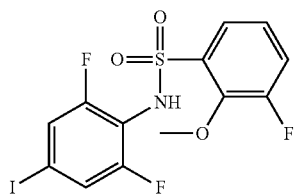 [SMILES: COc1c(F)cccc1S(=O)(=O)Nc1c(F)cc(I)cc1F]

Step a) 3-fluoro-2-methoxy-benzenesulfonyl chloride

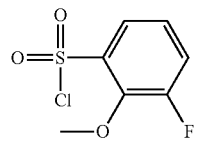

To a solution of 2-bromo-6-fluoroanisole (500.0 mg, 2.44 mmol) in tetrahydrofuran (20 mL) was added n-Butyllithium solution (2.5 M in hexane) (1.46 mL, 3.66 mmol, 1.5 eq) at −70° C. The mixture was stirred at −70° C. for 0.5 h. Sulfur dioxide (156 mg, 2.44 mmol) was passed through the resulting solution for 10 min (maintaining inner temperature below −40° C.), and stirred for 0.5 h at 25° C. To the mixture was added N-chlorosuccinimide (391 mg, 2.93 mmol) at 25° C., then the solution was stirred for 0.5 h at 25° C. The mixture was quenched by water (1 mL) and dried over $Na_2SO_4$. The solution was filtered and washed with EtOAc (5 mL×2). The organic layer was concentrated in vacuo to afford crude product as a yellow solid (555 mg, 101.3% yield). The crude product was used in next step directly.

Step b) N-(2,6-difluoro-4-iodo-phenyl)-3-fluoro-2-methoxy-benzenesulfonamide

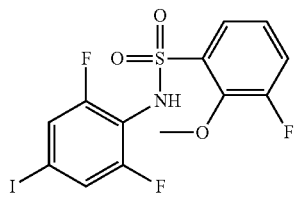 [SMILES: COc1c(F)cccc1S(=O)(=O)Nc1c(F)cc(I)cc1F]

A mixture of 2,6-difluoro-4-iodoaniline (300 mg, 1.18 mmol) in tetrahydrofuran (3 mL) was cooled to −70° C., LiHMDS (1 M in THF) (1.76 mL, 1.76 mmol) was added dropwise maintaining the temperature not higher than −60° C., then stirred for 1 h. A solution of 3-fluoro-2-methoxy-benzenesulfonyl chloride (555 mg, 2.47 mmol) in tetrahydrofuran (0.500 mL) was added dropwise maintaining the inner temperature not higher than −60° C., and it was stirred at −70° C. for another 4 h. To the solution was added aq. $NH_4Cl$ solution (3 mL) at 0° C., then the mixture was extracted with EtOAc (3 mL×3), and the organics washed with brine (9 mL). The organic layer was dried over $Na_2SO_4$, filtered, and the filtrate was concentrated in vacuo to obtain crude product as a black brown oil. The crude product was purified by Prep-TLC (PE: EtOAc=4:1) to afford desired product as a light yellow oil (196 mg, 32.2% yield). MS (ESI): m/z=444.0 [M+H]$^+$.

2) Biological Examples

2.1) Intracellular $Ca^{2+}$ Mobilization Assay (FLIPR)

A monoclonal HEK-293 cell line stably transfected with a cDNA encoding for the human mGlu4 receptor was generated. Cells were cultured according to standard protocols (Freshney, 2000) in Dulbecco's Modified Eagle Medium with high glucose supplemented with 1 mM glutamine, 10% (vol/vol) heat-inactivated bovine calf serum, penicillin/streptomycin, 50 μg/ml hygromycin and 15 μg/ml blasticidin (all cell culture reagents and antibiotics from Invitrogen, Basel, Switzerland).

About 24 hrs before an experiment, 5×10$^4$ cells/well were seeded in poly-D-lysine coated, black/clear-bottomed 96-well plates. The cells were loaded with 2.5 μM Fluo-4AM in loading buffer (1×HBSS, 20 mM HEPES) for 1 hr at 37° C. and washed five times with loading buffer. The cells were transferred into a Functional Drug Screening System 7000 (Hamamatsu, Paris, France), and 11 half logarithmic serial dilutions of test compound at 37° C. were added and the cells were incubated for 10-30 min. with on-line recording of fluorescence. Following this pre-incubation step, the agonist (2S)-2-amino-4-phosphonobutanoic acid (L-AP4) was added to the cells at a concentration corresponding to EC80 with on-line recording of fluorescence; in order to account for day-to-day variations in the responsiveness of cells, the EC80 of L-AP4 was determined immediately ahead of each experiment by recording of a full dose-response curve of L-AP4.

Responses were measured as peak increase in fluorescence minus basal (i.e. fluorescence without addition of L-AP4), normalized to the maximal stimulatory effect obtained with saturating concentrations of L-AP4. Graphs were plotted with the % maximal stimulatory using XLfit, a curve fitting program that iteratively plots the data using Levenburg Marquardt algorithm. The single site competition analysis equation used was y=A+((B−A)/(1+((x/C)D))), where y is the % maximal stimulatory effect, A is the minimum y, B is the maximum y, C is the IC50, x is the log 10 of the concentration of the competing compound and D is the slope of the curve (the Hill Coefficient). From these curves the IC50 (drug concentration at which 50% of the receptor activation achieved from the addition of L-AP4 in the experiment was inhibited), the Hill coefficient as well as the maximal response in % of the maximal stimulatory effect obtained with saturating concentrations of L-AP4 were calculated (see FIG. 1).

2.2) Results
The table below shows the data for all compounds for FLIPR assay.

| Example | Systematic Name | EC50 mGlu4 NAM FLIPR [μM] |
|---|---|---|
| 1 | 2-chloro-N-(2,6-difluoro-4-(phenylethynyl)phenyl)benzenesulfonamide | 4.280 |
| 2 | 2,3-dichloro-N-[2,6-difluoro-4-(2-phenylethynyl)phenyl]benzenesulfonamide | 1.682 |
| 3 | N-[2,6-difluoro-4-(2-phenylethynyl)phenyl]-2-(trifluoromethyl)benzenesulfonamide | 2.812 |
| 4 | 2,5-dichloro-N-[2,6-difluoro-4-(2-phenylethynyl)phenyl]benzenesulfonamide | 3.427 |
| 5 | N-[2,6-difluoro-4-(2-phenylethynyl)phenyl]-2-methyl-benzenesulfonamide | 3.715 |
| 6 | N-[2,6-difluoro-4-(2-phenylethynyl)phenyl]-2-fluoro-benzenesulfonamide | 4.636 |
| 7 | N-[2,6-difluoro-4-(2-phenylethynyl)phenyl]pyridine-3-sulfonamide | 4.667 |
| 8 | 3-chloro-N-[2,6-difluoro-4-(2-phenylethynyl)phenyl]benzenesulfonamide | 5.918 |
| 9 | 2-chloro-N-[2,6-difluoro-4-[2-(3-pyridyl)ethynyl]phenyl]benzenesulfonamide | 14.163 |
| 10 | N-[2,6-difluoro-4-(2-phenylethynyl)phenyl]pyridine-2-sulfonamide | 14.261 |
| 11 | 2,4-dichloro-N-[2,6-difluoro-4-(2-phenylethynyl)phenyl]benzenesulfonamide | 15.653 |
| 12 | 2-chloro-N-[2,6-difluoro-4-[2-(5-fluoro-3-pyridyl)ethynyl]phenyl]benzenesulfonamide | 2.958 |
| 13 | 2,3-dichloro-N-[2,6-difluoro-4-[2-(5-fluoro-3-pyridyl)ethynyl]phenyl]benzenesulfonamide | 0.556 |
| 14 | 3-chloro-N-[2,6-difluoro-4-[2-(5-fluoro-3-pyridyl)ethynyl]phenyl]benzenesulfonamide | 1.046 |
| 15 | 3-chloro-N-[2,6-difluoro-4-[2-(5-fluoro-3-pyridyl)ethynyl]phenyl]-2-methoxy-benzenesulfonamide | 0.778 |
| 16 | 2-chloro-N-[2,6-difluoro-4-(2-phenylethynyl)phenyl]-3-methyl-benzenesulfonamide | 1.563 |
| 17 | 2-chloro-N-[2,6-difluoro-4-(2-phenylethynyl)phenyl]-3-fluoro-benzenesulfonamide | 0.734 |
| 18 | 2-chloro-N-[2,6-difluoro-4-(2-phenylethynyl)phenyl]-5-methoxy-benzenesulfonamide | 3.938 |
| 19 | 2-chloro-N-[2,6-difluoro-4-(2-phenylethynyl)phenyl]-5-methyl-benzenesulfonamide | 1.261 |
| 20 | 3-chloro-N-[2,6-difluoro-4-(2-phenylethynyl)phenyl]-2-methyl-benzenesulfonamide | 1.075 |
| 21 | 3-chloro-N-[2,6-difluoro-4-(2-phenylethynyl)phenyl]-2-(trifluoromethyl)benzenesulfonamide | 15.307 |
| 22 | 2-chloro-N-[2,6-difluoro-4-(2-phenylethynyl)phenyl]pyridine-3-sulfonamide | 4.328 |
| 23 | 5-chloro-N-[2,6-difluoro-4-(2-phenylethynyl)phenyl]pyridine-3-sulfonamide | 3.110 |
| 24 | N-[2,6-difluoro-4-(2-phenylethynyl)phenyl]-5-fluoropyridine-3-sulfonamide | 2.047 |
| 25 | N-[2,6-difluoro-4-(2-phenylethynyl)phenyl]-1-methyl-1H-pyrazole-5-sulfonamide | 1.063 |
| 26 | N-[2,6-difluoro-4-(2-phenylethynyl)phenyl]-1-methyl-pyrazole-3-sulfonamide | 15.996 |
| 27 | 2-chloro-N-[2,6-difluoro-4-(2-phenylethynyl)phenyl]-3-methoxy-benzenesulfonamide | 8.428 |
| 28 | N-[2,6-difluoro-4-(2-phenylethynyl)phenyl]-2-methyl-3-(trifluoromethyl)benzenesulfonamide | 1.948 |
| 29 | N-[2,6-difluoro-4-(2-phenylethynyl)phenyl]-2-methyl-pyridine-3-sulfonamide | 2.893 |
| 30 | N-[2,6-difluoro-4-(2-phenylethynyl)phenyl]-2,5-dimethyl-benzenesulfonamide | 1.338 |
| 31 | N-[2,6-difluoro-4-(2-phenylethynyl)phenyl]-4-methyl-pyridine-3-sulfonamide | 1.400 |
| 32 | 3-chloro-N-[2,6-difluoro-4-(2-phenylethynyl)phenyl]-2-(methoxymethyl)benzenesulfonamide | 3.876 |
| 33 | 2-chloro-N-[2,6-difluoro-4-(2-phenylethynyl)phenyl]-3-(trifluoromethyl)benzenesulfonamide | 2.078 |
| 34 | N-[2,6-difluoro-4-(2-phenylethynyl)phenyl]-1,3-benzoxazole-7-sulfonamide | 6.560 |
| 35 | 3-chloro-N-[2,6-difluoro-4-(2-phenylethynyl)phenyl]-2-fluoro-benzenesulfonamide | 1.609 |
| 36 | N-[2,6-difluoro-4-(2-phenylethynyl)phenyl]-3-methyl-benzenesulfonamide | 5.022 |
| 37 | N-[2,6-difluoro-4-(2-phenylethynyl)phenyl]-3-fluoro-2-methyl-benzenesulfonamide | 1.052 |
| 38 | N-[2,6-difluoro-4-[2-(5-fluoro-3-pyridyl)ethynyl]phenyl]-3-fluoro-2,5-dimethyl-benzenesulfonamide; 2,2,2-trifluoroacetic acid | 0.434 |
| 39 | N-[2,6-difluoro-4-[2-(5-fluoro-3-pyridyl)ethynyl]phenyl]-2-methyl-pyrazole-3-sulfonamide; 2,2,2-trifluoroacetic acid | 10.478 |
| 40 | N-[2,6-difluoro-4-(2-phenylethynyl)phenyl]-3-fluoro-2,5-dimethyl-benzenesulfonamide | 0.808 |
| 41 | N-[2,6-difluoro-4-(2-phenylethynyl)phenyl]-1,3-dimethyl-pyrazole-4-sulfonamide; 2,2,2-trifluoroacetic acid | 9.347 |
| 42 | 3-chloro-N-[2,6-difluoro-4-[2-(3-methoxyphenyl)ethynyl]phenyl]-2-methyl-benzenesulfonamide | 1.325 |
| 43 | 3-chloro-N-[2,6-difluoro-4-[2-(3-fluorophenyl)ethynyl]phenyl]-2-methyl-benzenesulfonamide | 1.274 |
| 44 | 3-chloro-N-[4-[2-(3-chlorophenypethynyl]-2,6-difluoro-phenyl] -2-methyl-benzenesulfonamide | |
| 45 | N-[2,6-difluoro-4-[2-(3-fluorophenyl)ethynyl]phenyl]-3-fluoro-2,5-dimethyl-benzenesulfonamide | 1.318 |
| 46 | N-[2,6-difluoro-4-(2-phenylethynyl)phenyl]-3-fluoro-2-methoxy-benzenesulfonamide | 2.113 |
| 47 | N-[2,6-difluoro-4-[2-(3-methoxyphenyl)ethynyl]phenyl]-3-fluoro-2,5-dimethyl-benzenesulfonamide | 1.051 |
| 48 | N-[4-[2-(3-chlorophenyl)ethynyl]-2,6-difluoro-phenyl]-3-fluoro-2,5-dimethyl-benzenesulfonamide | 1.250 |
| 49 | N-[4-[2-(3,5-difluorophenyl)ethynyl]-2,6-difluoro-phenyl]-3-fluoro-2,5-dimethyl-benzenesulfonamide | 0.902 |

-continued

| Example | Systematic Name | EC50 mGlu4 NAM FLIPR [μM] |
|---|---|---|
| 50 | N-[2,6-difluoro-4-[2-(3-pyridyl)ethynyl]phenyl]-3-fluoro-2,5-dimethyl-benzenesulfonamide | 0.274 |
| 51 | N-[2,6-difluoro-4-[2-(m-tolypethynyl]phenyl]-3-fluoro-2,5-dimethyl-benzenesulfonamide | 1.409 |
| 52 | 3-chloro-N-[2,6-difluoro-4-[2-(5-fluoro-3-pyridyl)ethynyl]phenyl]-2-methyl-benzenesulfonamide | 0.761 |
| 53 | 3-chloro-N-[2,6-difluoro-4-[2-(5-fluoro-3-pyridyl)ethynyl]phenyl]-5-fluoro-2-methyl-benzenesulfonamide | 0.523 |
| 54 | 3-chloro-N-[2,6-difluoro-4-[2-(5-fluoro-3-pyridyl)ethynyl]phenyl]-2,5-dimethyl-benzenesulfonamide; 2,2,2-trifluoroacetic acid | 0.918 |
| 55 | 3-chloro-N-[4-[2-(5-chloro-3-pyridyl)ethynyl]-2,6-difluoro-phenyl]-2-methyl-benzenesulfonamide | 1.923 |
| 56 | 3-chloro-N-[2,6-difluoro-4-[2-(5-methyl-3-pyridyl)ethynyl]phenyl]-2-methyl-benzenesulfonamide; 2,2,2-trifluoroacetic acid | 1.469 |
| 57 | N-[2,6-difluoro-4-[2-(5-fluoro-3-pyridyl)ethynyl]phenyl]-3-fluoro-2-methyl-benzenesulfonamide; 2,2,2-trifluoroacetic acid | 0.575 |
| 58 | N-[4-(4-tert-butylpyrazol-1-yl)-2,6-difluoro-phenyl]-2-chloro-benzenesulfonamide | 13.036 |
| 59 | N-[4-(4-tert-butylpyrazol-1-yl)-2,6-difluoro-phenyl]-2,3-dichloro-benzenesulfonamide | 9.284 |
| 60 | N-[4-(4-tert-butylpyrazol-1-yl)-2,6-difluoro-phenyl]-3,5-dichloro-benzenesulfonamide | 6.724 |
| 61 | N-[2,6-difluoro-4-[2-(3-hydroxyphenyl)ethynyl]phenyl]-3-fluoro-2,5-dimethyl-benzenesulfonamide | 0.992 |

The invention claimed is:

1. A compound of formula (I)

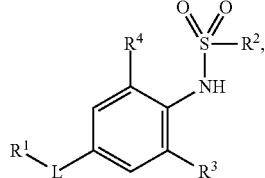
(I)

or a pharmaceutically acceptable salt thereof, wherein

L is a bond or —C≡C—;

$R^1$ is phenyl optionally substituted with 1 or 2 substituents independently selected from the group consisting of halogen, hydroxy, lower alkyl, lower alkoxy or haloalkyl;

or pyridyl optionally substituted with halogen, lower alkyl, lower alkoxy or haloalkyl;

or pyrazolyl optionally substituted with halogen, hydroxy, lower alkyl, lower alkoxy or haloalkyl;

$R^2$ is phenyl optionally substituted with 1 to 3 substituents selected from the group of halogen, hydroxy, lower alkyl, lower alkoxy, haloalkyl or alkoxyalkyl;

or a heteroaryl group optionally substituted with halogen, hydroxy, lower alkyl, lower alkoxy, haloalkyl or alkoxyalkyl, wherein the heteroaryl group is selected from the group consisting of:

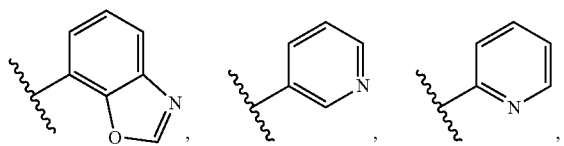

-continued

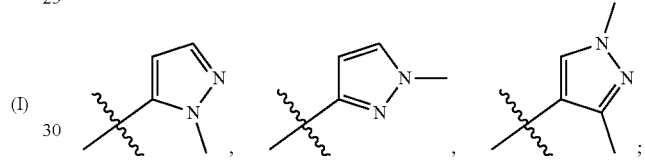

and $R^3$ and $R^4$ are halogen, haloalkyl, lower alkyl or lower alkoxy.

2. The compound of formula (I) according to claim 1, or a pharmaceutically acceptable salt thereof, wherein $R^1$ is a group selected from the group consisting of:

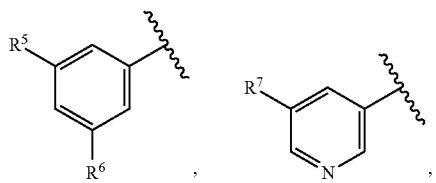

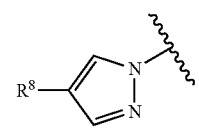

wherein $R^5$ is hydrogen or halogen;

$R^6$ is hydrogen, halogen, hydroxy, lower alkyl or lower alkoxy;

$R^7$ is hydrogen or halogen;

$R^8$ is hydrogen, hydroxy or lower alkyl.

3. The compound of formula (I) according to claim 1, or a pharmaceutically acceptable salt thereof, wherein $R^1$ is phenyl or pyridyl selected from the group consisting of:

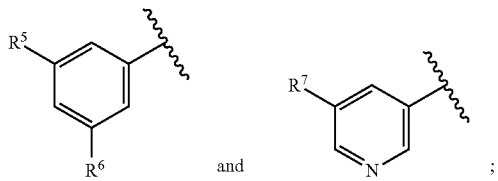

wherein
 R⁵ is hydrogen or halogen;
 R⁶ is hydrogen, halogen or hydroxy;
 R⁷ is hydrogen or halogen.
4. The compound of formula (I) according to claim 3, or a pharmaceutically acceptable salt thereof, wherein:
 R⁵ is hydrogen or fluorine;
 R⁶ is hydrogen, fluorine, chlorine or hydroxy; and
 R⁷ is hydrogen or fluorine.
5. The compound of formula (I) according to claim 1, or a pharmaceutically acceptable salt thereof, wherein R² is selected from the group consisting of:

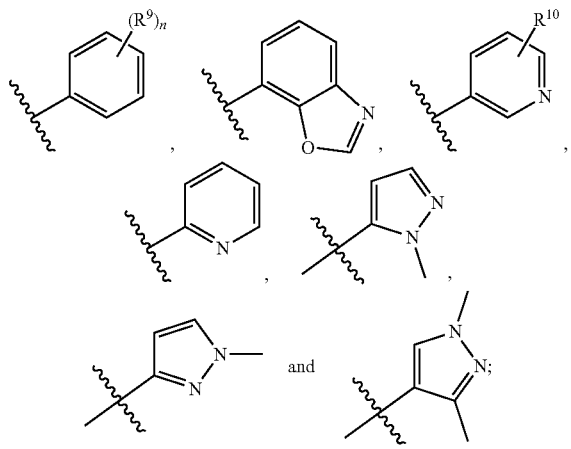

wherein
 R⁹ is halogen, lower alkyl, lower alkoxy, haloalkyl or alkoxyalkyl;
 R¹⁰ is hydrogen, halogen or lower alkyl; and
 n is 1, 2 or 3.
6. The compound of formula (I) according to claim 1, or a pharmaceutically acceptable salt thereof, wherein R² is phenyl or pyrazolyl selected from the group consisting of:

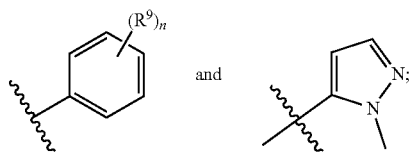

wherein
 R⁹ is halogen, lower alkyl or lower alkoxy; and
 n is 1, 2 or 3.
7. The compound of formula (I) according to claim 6, or a pharmaceutically acceptable salt thereof, wherein:
 R⁹ is chlorine, fluorine, methyl or methoxy; and
 n is 1, 2 or 3.
8. The compound of formula (I) according to claim 1, or a pharmaceutically acceptable salt thereof, wherein R³ and R⁴ are halogen.

9. The compound of formula (I) according to claim 8, or a pharmaceutically acceptable salt thereof, wherein R³ and R⁴ are fluorine.
10. The compound of formula (I) according to claim 1, or a pharmaceutically acceptable salt thereof, wherein:
 R¹ is a group selected from:

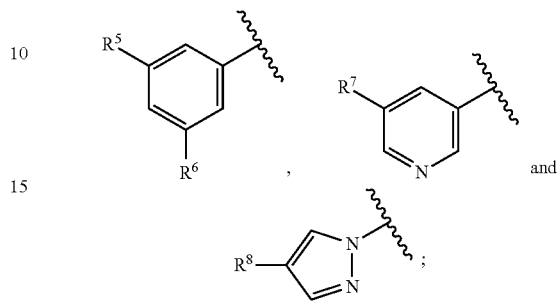

wherein
 R⁵ is hydrogen or halogen;
 R⁶ is hydrogen, halogen, hydroxy, lower alkyl or lower alkoxy;
 R⁷ is hydrogen or halogen;
 R⁸ is hydrogen, hydroxy or lower alkyl;
 R² is a group selected from:

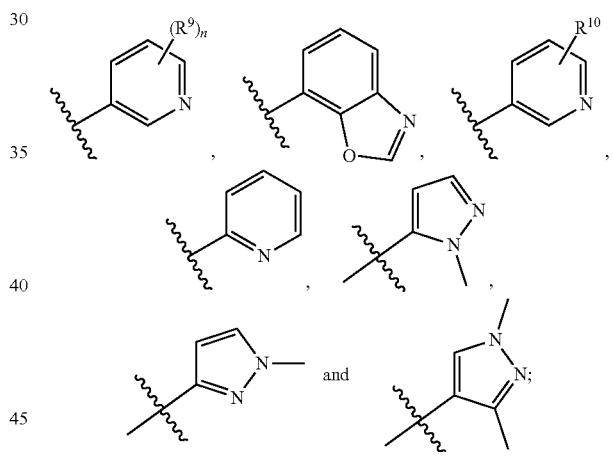

wherein
 R⁹ is halogen, lower alkyl, lower alkoxy, lower alkyl substituted by halogen or alkoxyalkyl;
 R¹⁰ is hydrogen, halogen or lower alkyl;
 n is 1, 2 or 3;
 R³ and R⁴ are halogen.
11. The compound of formula (I) according to claim 1, or a pharmaceutically acceptable salt thereof, wherein:
 R¹ is phenyl or pyridyl selected from:

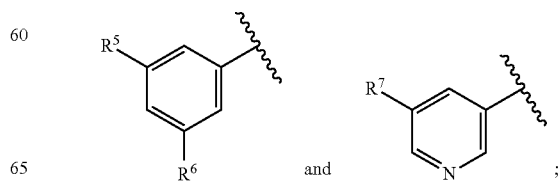

wherein
$R^5$ is hydrogen or halogen;
$R^6$ is hydrogen, halogen or hydroxy;
$R^7$ is hydrogen or halogen;
$R^2$ is phenyl or pyrazolyl selected from:

[structure: phenyl with $(R^9)_n$ substituent and N-methyl pyrazolyl]

wherein
$R^9$ is halogen, lower alkyl or lower alkoxy; and
n is 1, 2 or 3;
$R^3$ and $R^4$ are halogen.

12. The compound of formula (I) according to claim 11, or a pharmaceutically acceptable salt thereof, wherein:
$R^3$ and $R^4$ are fluorine;
$R^5$ is hydrogen or fluorine;
$R^6$ is hydrogen, fluorine, chlorine or hydroxy;
$R^7$ is hydrogen or fluorine;
$R^9$ is chloro, fluorine, methyl or methoxy; and
n is 1, 2 or 3.

13. The compound of formula (I) according to claim 1, or a pharmaceutically acceptable salt thereof, wherein the compound is selected from the group consisting of:
2-chloro-N-[2,6-difluoro-4-(2-phenylethynyl)phenyl] benzenesulfonamide;
2,3-dichloro-N-[2,6-difluoro-4-(2-phenylethynyl)phenyl] benzenesulfonamide;
N-[2,6-difluoro-4-(2-phenylethynyl)phenyl]-2-(trifluoromethyl)benzenesulfonamide;
2,5-dichloro-N-[2,6-difluoro-4-(2-phenylethynyl)phenyl] benzenesulfonamide;
N-[2,6-difluoro-4-(2-phenylethynyl)phenyl]-2-methyl-benzenesulfonamide;
N-[2,6-difluoro-4-(2-phenylethynyl)phenyl]-2-fluoro-benzenesulfonamide;
N-[2,6-difluoro-4-(2-phenylethynyl)phenyl]pyridine-3-sulfonamide;
3-chloro-N-[2,6-difluoro-4-(2-phenylethynyl)phenyl] benzenesulfonamide;
2-chloro-N-[2,6-difluoro-4-[2-(3-pyridyl)ethynyl]phenyl]benzenesulfonamide;
N-[2,6-difluoro-4-(2-phenylethynyl)phenyl]pyridine-2-sulfonamide;
2,4-dichloro-N-[2,6-difluoro-4-(2-phenylethynyl)phenyl]benzenesulfonamide;
2-chloro-N-[2,6-difluoro-4-[2-(5-fluoro-3-pyridyl)ethynyl]phenyl]benzenesulfonamide;
2,3-dichloro-N-[2,6-difluoro-4-[2-(5-fluoro-3-pyridyl)ethynyl]phenyl]benzenesulfonamide;
3-chloro-N-[2,6-difluoro-4-[2-(5-fluoro-3-pyridyl)ethynyl]phenyl]benzenesulfonamide;
3-chloro-N-[2,6-difluoro-4-[2-(5-fluoro-3-pyridyl)ethynyl]phenyl]-2-methoxy-benzenesulfonamide;
2-chloro-N-[2,6-difluoro-4-(2-phenylethynyl)phenyl]-3-methyl-benzenesulfonamide;
2-chloro-N-[2,6-difluoro-4-(2-phenylethynyl)phenyl]-3-fluoro-benzenesulfonamide;
2-chloro-N-[2,6-difluoro-4-(2-phenylethynyl)phenyl]-5-methoxy-benzenesulfonamide;
2-chloro-N-[2,6-difluoro-4-(2-phenylethynyl)phenyl]-5-methyl-benzenesulfonamide;
3-chloro-N-[2,6-difluoro-4-(2-phenylethynyl)phenyl]-2-methyl-benzenesulfonamide;
3-chloro-N-[2,6-difluoro-4-(2-phenylethynyl)phenyl]-2-(trifluoromethyl)benzenesulfonamide;
2-chloro-N-[2,6-difluoro-4-(2-phenylethynyl)phenyl] pyridine-3-sulfonamide;
5-chloro-N-[2,6-difluoro-4-(2-phenylethynyl)phenyl] pyridine-3-sulfonamide;
N-[2,6-difluoro-4-(2-phenylethynyl)phenyl]-5-fluoro-pyridine-3-sulfonamide;
N-[2,6-difluoro-4-(2-phenylethynyl)phenyl]-1-methyl-1H-pyrazole-5-sulfonamide;
N-[2,6-difluoro-4-(2-phenylethynyl)phenyl]-1-methyl-pyrazole-3-sulfonamide;
2-chloro-N-[2,6-difluoro-4-(2-phenylethynyl)phenyl]-3-methoxy-benzenesulfonamide;
N-[2,6-difluoro-4-(2-phenylethynyl)phenyl]-2-methyl-3-(trifluoromethyl)benzenesulfonamide;
N-[2,6-difluoro-4-(2-phenylethynyl)phenyl]-2-methyl-pyridine-3-sulfonamide;
N-[2,6-difluoro-4-(2-phenylethynyl)phenyl]-2,5-dimethyl-benzenesulfonamide;
N-[2,6-difluoro-4-(2-phenylethynyl)phenyl]-4-methyl-pyridine-3-sulfonamide;
3-chloro-N-[2,6-difluoro-4-(2-phenylethynyl)phenyl]-2-(methoxymethyl)benzenesulfonamide;
2-chloro-N-[2,6-difluoro-4-(2-phenylethynyl)phenyl]-3-(trifluoromethyl)benzenesulfonamide;
N-[2,6-difluoro-4-(2-phenylethynyl)phenyl]-1,3-benzoxazole-7-sulfonamide;
3-chloro-N-[2,6-difluoro-4-(2-phenylethynyl)phenyl]-2-fluoro-benzenesulfonamide;
N-(2,6-difluoro-4-(phenylethynyl)phenyl)-3-methylbenzenesulfonamide;
N-[2,6-difluoro-4-(2-phenylethynyl)phenyl]-3-fluoro-2-methyl-benzenesulfonamide;
N-[2,6-difluoro-4-[2-(5-fluoro-3-pyridyl)ethynyl]phenyl]-3-fluoro-2,5-dimethyl-benzenesulfonamide; 2,2,2-trifluoroacetic acid salt;
N-[2,6-difluoro-4-[2-(5-fluoro-3-pyridyl)ethynyl]phenyl]-2-methyl-pyrazole-3-sulfonamide 2,2,2-trifluoroacetic acid salt;
N-[2,6-difluoro-4-(2-phenylethynyl)phenyl]-3-fluoro-2,5-dimethyl-benzenesulfonamide;
N-[2,6-difluoro-4-(2-phenylethynyl)phenyl]-1,3-dimethyl-pyrazole-4-sulfonamide; 2,2,2-trifluoroacetic acid salt;
3-chloro-N-[2,6-difluoro-4-[2-(3-methoxyphenyl)ethynyl]phenyl]-2-methyl-benzenesulfonamide;
3-chloro-N-[2,6-difluoro-4-[2-(3-fluorophenyl)ethynyl] phenyl]-2-methyl-benzenesulfonamide;
3-chloro-N-[4-[2-(3-chlorophenyl)ethynyl]-2,6-difluoro-phenyl]-2-methyl-benzenesulfonamide;
N-[2,6-difluoro-4-[2-(3-fluorophenyl)ethynyl]phenyl]-3-fluoro-2,5-dimethyl-benzenesulfonamide;
N-[2,6-difluoro-4-(2-phenylethynyl)phenyl]-3-fluoro-2-methoxy-benzenesulfonamide;
N-[2,6-difluoro-4-[2-(3-methoxyphenyl)ethynyl]phenyl]-3-fluoro-2,5-dimethyl-benzenesulfonamide;
N-[4-[2-(3-chlorophenyl)ethynyl]-2,6-difluoro-phenyl]-3-fluoro-2,5-dimethyl-benzenesulfonamide;
N-[4-[2-(3,5-difluorophenyl)ethynyl]-2,6-difluoro-phenyl]-3-fluoro-2,5-dimethyl-benzenesulfonamide;
N-[2,6-difluoro-4-[2-(3-pyridyl)ethynyl]phenyl]-3-fluoro-2,5-dimethyl-benzenesulfonamide;

N-[2,6-difluoro-4-[2-(m-tolyl)ethynyl]phenyl]-3-fluoro-2,5-dimethyl-benzenesulfonamide;
3-chloro-N-[2,6-difluoro-4-[2-(5-fluoro-3-pyridyl)ethynyl]phenyl]-2-methyl-benzenesulfonamide;
3-chloro-N-[2,6-difluoro-4-[2-(5-fluoro-3-pyridyl)ethynyl]phenyl]-5-fluoro-2-methyl-benzenesulfonamide;
3-chloro-N-(2,6-difluoro-4-((5-fluoropyridin-3-yl)ethynyl)phenyl)-2,5-dimethylbenzenesulfonamide 2,2,2-trifluoroacetate;
3-chloro-N-(4-((5-chloropyridin-3-yl)ethynyl)-2,6-difluorophenyl)-2-methylbenzenesulfonamide;
3-chloro-N-[2,6-difluoro-4-[2-(5-methyl-3-pyridyl)ethynyl]phenyl]-2-methyl-benzenesulfonamide; 2,2,2-trifluoroacetic acid;
N-[2,6-difluoro-4-[2-(5-fluoro-3-pyridyl)ethynyl]phenyl]-3-fluoro-2-methyl-benzenesulfonamide; 2,2,2-trifluoroacetic acid;
N-[4-(4-tert-butylpyrazol-1-yl)-2,6-difluoro-phenyl]-2-chloro-benzenesulfonamide;
N-[4-(4-tert-butylpyrazol-1-yl)-2,6-difluoro-phenyl]-2,3-dichloro-benzenesulfonamide;
N-[4-(4-tert-butylpyrazol-1-yl)-2,6-difluoro-phenyl]-3,5-dichloro-benzenesulfonamide; and
N-[2,6-difluoro-4-[2-(3-hydroxyphenyl)ethynyl]phenyl]-3-fluoro-2,5-dimethyl-benzenesulfonamide.

14. The compound of formula (I) according to claim 1, or a pharmaceutically acceptable salt thereof, wherein the compound is selected from the group consisting of:
2,3-dichloro-N-[2,6-difluoro-4-[2-(5-fluoro-3-pyridyl)ethynyl]phenyl]benzenesulfonamide;
3-chloro-N-[2,6-difluoro-4-[2-(5-fluoro-3-pyridyl)ethynyl]phenyl]benzenesulfonamide;
3-chloro-N-[2,6-difluoro-4-[2-(5-fluoro-3-pyridyl)ethynyl]phenyl]-2-methoxy-benzenesulfonamide;
2-chloro-N-[2,6-difluoro-4-(2-phenylethynyl)phenyl]-3-fluoro-benzenesulfonamide;
2-chloro-N-[2,6-difluoro-4-(2-phenylethynyl)phenyl]-5-methyl-benzenesulfonamide;
3-chloro-N-[2,6-difluoro-4-(2-phenylethynyl)phenyl]-2-methyl-benzenesulfonamide;
N-[2,6-difluoro-4-(2-phenylethynyl)phenyl]-1-methyl-1H-pyrazole-5-sulfonamide;
N-[2,6-difluoro-4-(2-phenylethynyl)phenyl]-3-fluoro-2-methyl-benzenesulfonamide;
N-[2,6-difluoro-4-[2-(5-fluoro-3-pyridyl)ethynyl]phenyl]-3-fluoro-2,5-dimethyl-benzenesulfonamide; 2,2,2-trifluoroacetic acid salt;
N-[2,6-difluoro-4-(2-phenylethynyl)phenyl]-3-fluoro-2,5-dimethyl-benzenesulfonamide;
3-chloro-N-[2,6-difluoro-4-[2-(3-fluorophenyl)ethynyl]phenyl]-2-methyl-benzenesulfonamide;
N-[2,6-difluoro-4-[2-(3-fluorophenyl)ethynyl]phenyl]-3-fluoro-2,5-dimethyl-benzenesulfonamide;
N-[2,6-difluoro-4-[2-(3-methoxyphenyl)ethynyl]phenyl]-3-fluoro-2,5-dimethyl-benzenesulfonamide;
N-[4-[2-(3-chlorophenyl)ethynyl]-2,6-difluoro-phenyl]-3-fluoro-2,5-dimethyl-benzenesulfonamide;
N-[4-[2-(3,5-difluorophenyl)ethynyl]-2,6-difluoro-phenyl]-3-fluoro-2,5-dimethyl-benzenesulfonamide;
N-[2,6-difluoro-4-[2-(3-pyridyl)ethynyl]phenyl]-3-fluoro-2,5-dimethyl-benzenesulfonamide;
3-chloro-N-[2,6-difluoro-4-[2-(5-fluoro-3-pyridyl)ethynyl]phenyl]-2-methyl-benzenesulfonamide;
3-chloro-N-[2,6-difluoro-4-[2-(5-fluoro-3-pyridyl)ethynyl]phenyl]-5-fluoro-2-methyl-benzenesulfonamide;
3-chloro-N-(2,6-difluoro-4-((5-fluoropyridin-3-yl)ethynyl)phenyl)-2,5-dimethylbenzenesulfonamide 2,2,2-trifluoroacetate;
N-[2,6-difluoro-4-[2-(5-fluoro-3-pyridyl)ethynyl]phenyl]-3-fluoro-2-methyl-benzenesulfonamide; 2,2,2-trifluoroacetic acid; and
N-[2,6-difluoro-4-[2-(3-hydroxyphenyl)ethynyl]phenyl]-3-fluoro-2,5-dimethyl-benzenesulfonamide.

15. A process for the preparation of a compound according to any one of claims 1 and 2 to 14, or a pharmaceutically acceptable salt thereof, comprising reacting an amine 1:

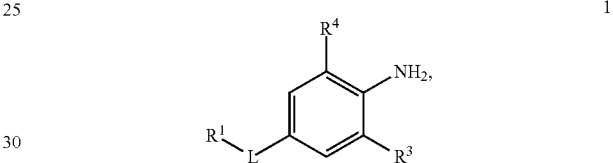

with a sulfonyl chloride 2

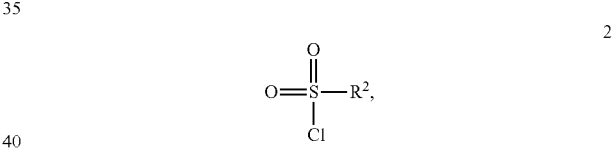

wherein $R^1$, $R^2$, $R^3$ and $R^4$ are as defined in any one of claims 1 and 2 to 14, to form said compound of formula (I), and if desired, converting the compounds obtained into a pharmaceutically acceptable salt thereof.

16. A pharmaceutical composition comprising a compound according to claim 1, or a pharmaceutically acceptable salt thereof, and a pharmaceutically acceptable excipient.

17. A method for the treatment of anxiety, wherein the method comprises administering to a subject in need thereof an effective amount of a compound according to claim 1, or a pharmaceutically acceptable salt thereof.

* * * * *